United States Patent
Burns et al.

(10) Patent No.: US 7,598,272 B2
(45) Date of Patent: Oct. 6, 2009

(54) KINASE INHIBITORS

(75) Inventors: Christopher John Burns, Seddon (AU); Xianyong Bu, Viewbank (AU); Andrew Frederick Wilks, South Yarra (AU)

(73) Assignee: Cytopia Research Pty Ltd, Melbourne (AU)

(*) Notice: Subject to any disclaimer, the term of this patent is extended or adjusted under 35 U.S.C. 154(b) by 0 days.

(21) Appl. No.: 11/397,973

(22) Filed: Apr. 4, 2006

(65) Prior Publication Data

US 2006/0241112 A1 Oct. 26, 2006

Related U.S. Application Data

(62) Division of application No. 10/472,156, filed as application No. PCT/AU03/00628 on May 23, 2003, now Pat. No. 7,259,179.

(60) Provisional application No. 60/398,998, filed on Jul. 26, 2002.

(30) Foreign Application Priority Data

May 23, 2002 (AU) .................................... PS2514

(51) Int. Cl.
C07D 209/04 (2006.01)
C07D 237/02 (2006.01)
A61K 31/497 (2006.01)

(52) U.S. Cl. .................. 514/336; 544/224; 544/336

(58) Field of Classification Search ................ 514/396, 514/359, 360, 252.1; 544/224, 336; 548/100, 548/125, 452, 469, 517
See application file for complete search history.

(56) References Cited

FOREIGN PATENT DOCUMENTS

| WO | WO-00/62778 | 10/2000 |
|---|---|---|
| WO | WO-02/060492 | 8/2002 |
| WO | WO-04/004730 | 1/2004 |
| WO | WO-04/085388 | 10/2004 |

OTHER PUBLICATIONS

Harpur et al., Oncogene (1992) 7:1347-1353.
International Search Report for PCT/AU03/00628, mailed on Aug. 5, 2003, 3 pages.
Kozma et al.,EMBO Journal (1986) 7(1):147-154.
Sadowski et al., Molecular and Cellular Biology (1986) 6(12):4396-4408.

(Continued)

*Primary Examiner*—James O. Wilson
*Assistant Examiner*—Paul V. Ward
(74) *Attorney, Agent, or Firm*—Morrison & Foerster LLP

(57) ABSTRACT

A compound of the general formula:

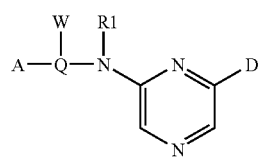

or pharmaceutically acceptable salts, hydrates, solvates, crystal forms or diastereomers thereof is described. A method of treating protein kinase-associated disease states using the compound of formula I is also described.

11 Claims, 2 Drawing Sheets

Dose-response curves for representative pyrazines possessing inhibitory activity in Tel-Jak2 transformed cell line

OTHER PUBLICATIONS

Spiotto and Chung, The Prostate (2000) 42:88-98.
Wilks and Kurban, Oncogene (1988) 3:289-294.
Wilks et al., Molecular and Cellular Biology (1991) 11(4):2057-2065.
Supplementary European Search Report for EP 03722065.4; mailed on Jun. 6, 2006, 3 pages.
Duhe et al., Cell Biochemistry and Biophysics (2001) 34(1):17-59.
Gavezzotti, Accounts of Chemical Research (1994) 27:309-314.
Vippagunta et al., Advanced Drug Delivery Reviews (2001) 48:3-26.

Figure 1: Dose-response curves for representative pyrazines possessing inhibitory activity in Tel-Jak2 transformed cell line
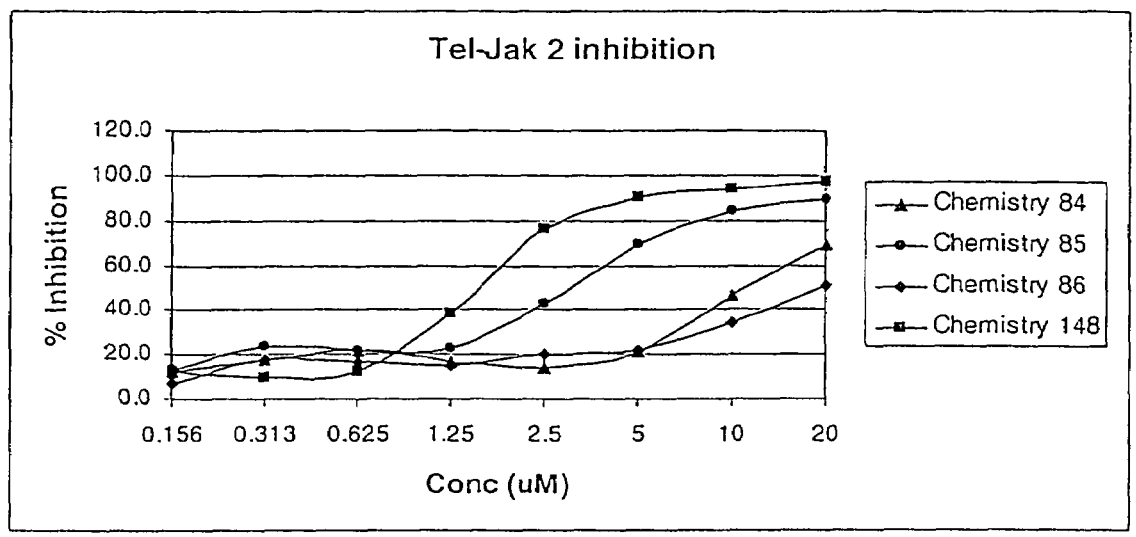
Figure 2: Dose-response curves for representative pyrazines possessing inhibitory activity in Tel-Jak3 transformed cell line
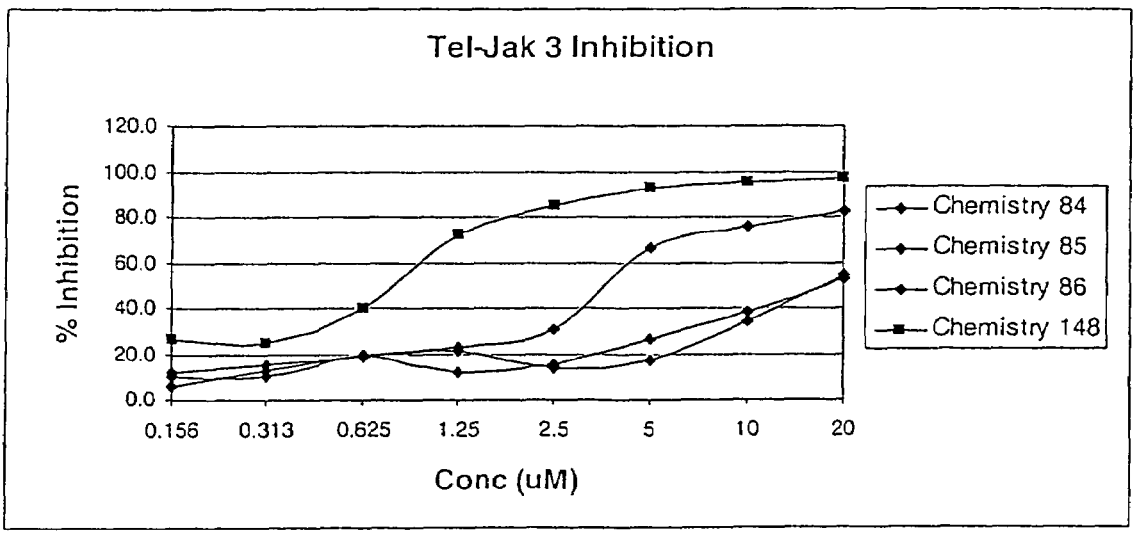

Figure 3: Dose-response curves for R and S enantiomers of representative 2-(α-methyl benzylamino)-pyrazine possessing inhibitory activity in Tel-Jak2 transformed cell line
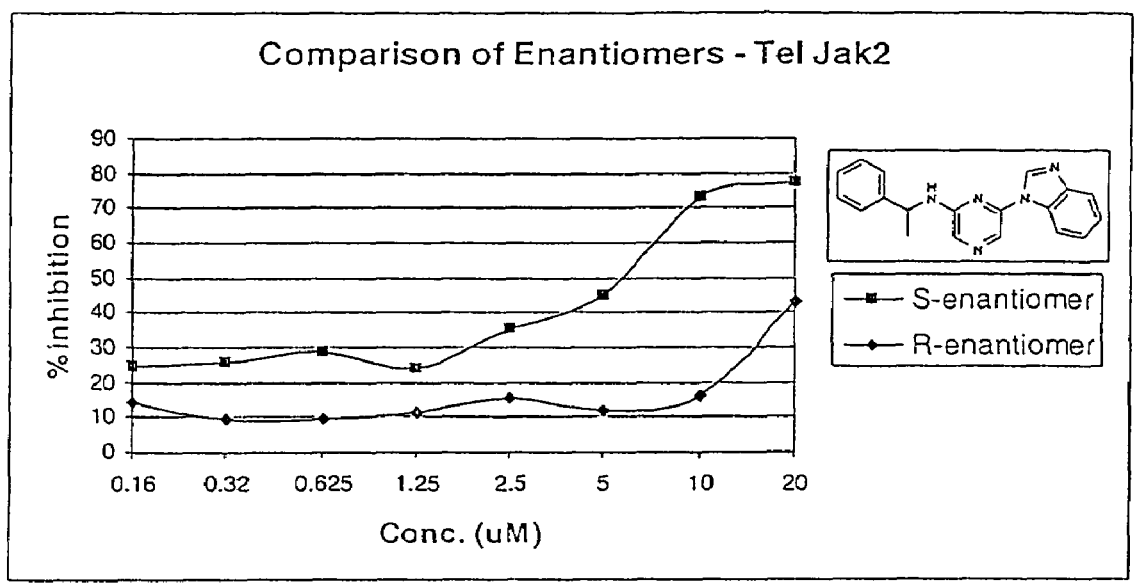

SEQUENCE LISTING

<160> NUMBER OF SEQ ID NOS: 15

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ccgctcgaga ctgaagtgga ccccacacat                                30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
cggggtacct tattttaaaa gtgcttcaaa                                30

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
acgcgtcgac ggtgcctttg aagaccggga t                              31

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
atagtttagc ggccgctcag aatgaaggtc attt                           34

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
ccgctcgagt atgcctgcca agaccccacg                                30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cggggtaccc tatgaaaagg acagggagtg                                30

<210> SEQ ID NO 7
<211> LENGTH: 33

```
<212> TYPE: DNA
<213> ORGANISM: Artificial Sequence
<220> FEATURE:
<223> OTHER INFORMATION: Primer

<400> SEQUENCE: 7
ggagcactcg agatggtagc acacaaccag gtg                              33

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
ggagcaggaa ttccggcgct gccggtcaaa tctgg                            35

<210> SEQ ID NO 9
<211> LENGTH: 17
<212> TYPE: PRT
<213> ORGANISM: Artificial Sequence
<220> FEATURE:
<223> OTHER INFORMATION: Peptide substrate

<400> SEQUENCE: 9

Glu Gly Pro Trp Leu Glu Glu Glu Glu Ala Tyr Gly Trp Met Asp
  1               5                  10                  15

Phe

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
ggaggatcct gatctctctc gctgtgagac                                  30

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
aggcgtcgac ttcttcttca tggttctg                                    28

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
acgcgtcgac ggtgcctttg aagaccggga t                                31

<210> SEQ ID NO 13
<211> LENGTH: 34
<212> TYPE: DNA
<213> ORGANISM: Artificial Sequence
<220> FEATURE:
<223> OTHER INFORMATION: Primer
```

```
<400> SEQUENCE: 13
atagtttagc ggccgctcag aatgaaggtc attt                               34

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
gaagtcgact atgcctgcca agaccccacg atctt                              35

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
ggatctagac tatgaaaagg acagggagtg gtgttt                             36
```

KINASE INHIBITORS

CROSS-REFERENCE TO RELATED APPLICATION

This application is a divisional of U.S. application Ser. No. 10/472,156 filed Sep. 19, 2003, which is the national phase of PCT application PCT/AU03/00628 having an international filing date of May 23, 2003, which claims benefit of U.S. provisional application No. 60/398,998 filed Jul. 26, 2002 and Australian application No. PS2514 filed May 23, 2002. Each of these documents is incorporated herein by reference in their entirety.

FIELD OF THE INVENTION

The present invention relates to the field of inhibitors of protein kinases.

BACKGROUND OF THE INVENTION

Protein kinases are a family of enzymes that catalyse the phosphorylation of specific residues in proteins. In general protein kinases fall into several groups; those which preferentially phosphorylate serine and/or threonine residues, those which preferentially phosphorylate tyrosine residues and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis.

Protein kinases include, for example, but are not limited to, members of the Protein Tyrosine Kinase family (PTKs), which in turn can be divided into the cytoplasmic PTKs and the receptor PTKs (RTKs). The cytoplasmic PTKS include the SRC family, (including: BLK; FGR; FYN; HCK; LCK; LYN; SRC; YES and YRK); the BRK Family (including: BRK; FRK, SAD; and SRM); the CSK family (including: CSK and CTK); the BTK family, (including BTK; ITK; TEC; MKK2 and TXK), the Janus kinase family, (including: JAKI, JAK2, JAK3 and Tyk2), the FAK family (including, FAK and PYK2); the Fes family (including FES and FER), the ZAP70 family (including ZAP70 and SYK); the ACK family (including ACK1 and ACK2); and the Abl family (including ABL and ARG). The RTK family includes the EGF-Receptor family (including, EGFR, HER2, HER3 and HER4); the Insulin Receptor family (including INS-R and IGF1-R); the PDGF-Receptor family (including PDGFRα, PDGFRβ, CSF1R, KIT, FLK2); the VEGF-Receptor family (including; FLT1, FLK1 and FLT4); the FGF-Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYR010); the ROS family (including ROS); the RET family (including RET); the LTK family (including LTK and ALK); the ROR family (including ROR1 and ROR2); The Musk family (including Musk); the LMR family including LMR1, LMR2 and LMR3); and the SuRTK106 family (including SuRTK106).

Similarly, the serine/threonine specific kinases comprise a number of distinct sub-families, including; the extracellular signal regulated kinases, (p42/ERK2 and p44/ERKI); c-Jun NH2-terminal kinase (JNK); cAMP-responsive element-binding protein kinases (CREBK); cAMP-dependent kinase (CAPK); mitogen-activated protein kinase-activated protein kinase (MAPK and its relatives); stress-activated protein kinase p38/SAPK2; mitogen-and stress-activated kinase (MSK); protein kinases, PKA, PKB and PKC inter alia.

Additionally, the genomes of a number of pathogenic organisms possess genes encoding protein kinases. For example, the malarial parasite Plasmodium falciparum and viruses such as HPV and Hepatitis viruses appear to bear kinase related genes.

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream off the kinase. In all se instances, selective inhibition of the action of the kinase might be expected to have a beneficial effect. Diseases where aberrant kinase activity has been implicated include: diabetes; restenosis; atherosclerosis; fibrosis of the liver and kidney; ocular diseases; myelo- and lymphoproliferative disorders; cancer-such as prostate cancer, colon cancer, breast cancer, head and neck cancer, leukemia and lymphoma; and, auto-immune diseases such as Atopic Dermatitis, Asthma, rheumatoid arthritis, Crohn's disease, psoriasis, Crouzon syndrome, achondroplasia, and thanatophoric dysplasia.

The JAK family of protein tyrosine kinases (PTKs) play a central role in the cytokine dependent regulation of the proliferation and end function of several important cell types of the immune system.

A direct comparison of the four currently known mammalian JAK family members reveals the presence of seven highly conserved domains (Harpur et al. 1992). In seeking a nomenclature for the highly conserved domains characteristic of this family of PTKs, the classification used was guided by the approach of Pawson and co-workers (Sadovski et al, 1986) in their treatment of the SRC homology (SH) domains. The domains have been enumerated accordingly with most C-terminal homology domain designated JAK Homology domain 1 (JH1). The next domain N-terminal to JH1 is the kinase-related domain, designated here as the JH2 domain. Each domain is then enumerated up to the JH7 located at the N-terminus. The high degree of conservation of these JAK homology (JH) domains suggests that they are each likely to play an important role in the cellular processes in which these proteins operate. However, the boundaries of the JAK homology domains are arbitrary, and may or may not define functional domains. Nonetheless, their delineation is a useful device to aid the consideration of the overall structural similarity of this class of proteins.

The feature most characteristic of the JAK family of PTKs is the possession of two kinase-related domains (JH1 and JH2) (Wilks et al, 1991). The putative PTK domain of JAK1 (JH1) contains highly conserved motifs typical of PTK domains, including the presence of a tyrosine residue at position 1022 located 11 residues C-terminal to sub-domain VII that is considered diagnostic of membership of the tyrosine-specific class of protein kinases. Alignment of the human JAK1 PTK domain (255 amino adds), with other members of the PTK class of proteins revealed homology with other functional PTKs (for example, 28% identity with c-fes (Wilks and Kurban, 1988) and 37% homology to TRK (Kozma et al, 1988). The JH1 domains of each of the JAK family members possess a interesting idiosyncrasy within the highly conserved sub-domain VIII motif (residues 1015 to 1027 in JAK2) that is believed to lie close to the active site, and define substrate specificity. The phenylalanine and tyrosine residues flanking the conserved tryptophan in this motif are unique to the JAK family of PTKs. Aside from this element, the JH1 domains of each of the members of the JAK family are typical PTK domains.

The central role played by the JAK family of protein tyrosine kinases in the cytokine dependent regulation of the proliferation and end function of several important cell types means that agents which inhibit JAK are useful in the prevention and chemotherapy of disease states dependent on these enzymes. Potent and specific inhibitors of each of the currently known four JAK family members will provide a means of inhibiting the action of those cytokines that drive immune pathologies, such as asthma (e.g. IL-13; JAK1, JAK2), and leukemia/lymphoma (e.g. IL-2: JAK1 and JAK3).

Furthermore, certain types of cancer such as prostate cancer develop autocrine production of certain cytokines as a selectable mechanism of developing growth and/or metastatic potential. An example of this is cancer of the prostate, where IL-6 is produced by and stimulates the growth of prostate cancer cell lines such as TSU and TC3 (Spiotto MT, and Chung TD, 2000). Interestingly, levels of IL-6 are elevated in sera of patients with metastatic prostate cancer.

A great deal of literature covets the area of cytokine signalling. The present inventors have focussed on the JAK/STAT pathway that is involved in the direct connection of cytokine receptor to target genes (such as cell cycle regulators (e.g. p21) and anti-apoptosis genes (such as ($Bcl-X_L$)).

The JAK/STAT Pathway

The delineation of a particularly elegant signal transduction pathway downstream of the non-protein tyrosine kinase cytokine receptors has recently been achieved. In this pathway the key components are: (i) A cytokine receptor chain (or chains) such as the Interleukin-4 receptor or the Interferon γ receptor; (ii) a member (or members) of the JAK family of PTKs; (iii) a member(s) of the STAT family of transcription factors, and (iv) a sequence specific DNA element to which the activated STAT will bind.

A review of the JAK/STAT literature offers strong support to the notion that this pathway is important for the recruitment and marshalling of the host immune response to environmental insults, such as viral and bacterial infection. This is well exemplified in Table 1 and Table 2. Information accumulated from gene knock-out experiments have underlined the importance of members of the JAK family to the intracellular signalling triggered by a number of important immune regulatory cytokines. The therapeutic possibilities stemming from inhibiting (or enhancing) the JAK/STAT pathway are thus largely in the sphere of immune modulation, and as such are likely to be promising drugs for the treatment of a range of pathologies in this area. In addition to the diseases listed in Tables 1 and 2, inhibitors of JAKs could be used as immunosuppresive agents for organ transplants and autoimmune diseases such as lupus, multiple sclerosis, rheumatoid arthritis, Type I diabetes, autoimmune thyroid disorders, Alzheimer's disease and other autoimmune diseases. Additionally, treatment of cancers such as prostate-cancer by JAK inhibitors is indicated.

TABLE 1

| Disease Type | Cell Types Involved | Characteristics |
|---|---|---|
| Atopy | | |
| Allergic Asthma | (Mast Cells | T-cell activation of |
| Atopic Dermatitis (Eczema) | (Eosinophils | B-cells followed by IgE |
| Allergic Rhinitis | (T-Cells | mediated activation of |
|  | (B-Cells | resident Mast cells and Eosinophils |
| Cell Mediated Hypersensitivity | | |
| Allergic Contact Dermatitis | (T-cells | |
| Hypersensitivity Pneumonitis | (B-cells | T-cell hypersensitivity |
| Rheumatic Diseases | | |
| Systemic Lupus Erythematosus (SLE) | (Monocytes | Cytokine Production (e.g.TNF, IL-1, CSF-1, |
| Rheumatoid Arthritis | (Macrophages | GM-CSF) |
| Juvenile Arthritis | (Neutrophils | T-cell Activation |
| Sjögren's Syndrome | (Mast Cells | JAK/STAT activation |
| Scleroderma | (Eosinophils | |
| Polymyositis | (T-Cells | |
| Ankylosing Spondylitis | (B-Cells | |
| Psoriatic Arthritis | | |
| Viral Diseases | | |
| Epstein Barr Virus (EBV) | Lymphocytes | JAK/STAT Activation |
| Hepatitis B | Hepatocytes | JAK/STAT Activation |
| Hepatitis C | Hepatocytes | JAK/STAT Inhibition |
| HIV | Lymphocytes | JAK/STAT Activation |
| HTLV 1 | Lymphocytes | JAK/STAT Activation |
| Varicella-Zoster Virus (VZV) | Fibroblasts | JAK/STAT Inhibition |
| Human Papilloma Virus (HPV) | Epithelial cells | JAK/STAT Inhibition |
| Cancer | | |
| Leukemia | Leucocytes | (Cytokine production |
| Lymphoma | Lymphocytes | (JAK/STAT Activation |

TABLE 2

Diseases Potentially Treatable By JAK-Based Drug Therapies

| Target Disease | Cytokine | JAK family member | Strength of Association |
|---|---|---|---|
| Asthma | IL-4 & IL-9 | JAK1 &JAK3 | +++ |
|  | IL-13 | JAK1 & JAK2 | +++ |
|  | IL-5 | JAK2 | +++ |
| Eczema | IL-4 | JAK1 & JAK3 | +++ |
|  | IFN-α | JAK1 & JAK2 | +++ |
| Food Allergy | IL-4 | JAK1 & JAK3 | +++ |
| Inflammatory Bowel Disease & Crohn's Disease | IL-4 | JAK1 & JAK3 | +++ |
| Leukaemia And Lymphoma | (IL-2) | JAK3, JAK1 & JAK2 | +++ |
| Cutaneous Inflammation | GM-CSF & IL-6 | JAK1 & JAK2 | +++ |
| Immune Suppression By Solid Tumour | IL-10 | JAK1 & TYK2 | +++ |
| Prostate Cancer | IL-6 | JAK1, JAK2 &Tyk2 | +++ |

BRIEF DESCRIPTION OF THE FIGURES

FIGS. 1 and 2 show the inhibitory activity of representative pyrazines in Tel-Jak2 and Tel-Jak3 transformed cell lines, respectively. FIG. 3 shows the inhibitory activity of 2-(α-methyl benzylamino)-pyrazine in Tel-Jak2 transformed cell line.

SUMMARY OF THE INVENTION

The present inventors have found that a group of compounds based upon the disubstituted pyrazine scaffold I, are inhibitors of protein kinases.

Accordingly, in a first aspect the present invention consists in a compound of the general formula:

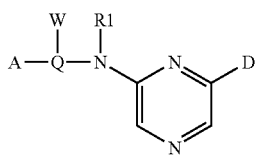

I or pharmaceutically acceptable salts, hydrates, solvates, crystal forms or diastereomers thereof, wherein:

D is a heterocyclic ring selected from:

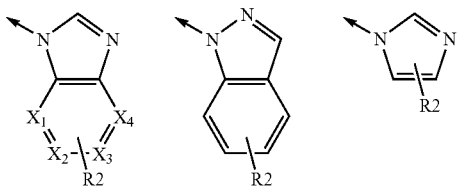

where $X_1, X_2, X_3, X_4$ are optionally substituted carbon, or one of $X_1, X_2, X_3, X_4$ is N; R2 is 0-4 substituents independently chosen from H, halogen, $C_{1-4}$ alkyl, $CH_2F$, $CHF_2$, $CF_3$, $OCF_3$, aryl, hetaryl, $C_{1-4}$alkyl$OC_{1-4}$ alkyl, $C_{1-4}$alkylOaryl, $C_{1-4}$alkylNR3R4, $CO_2R3$, CONR3R4, CONR3SO$_2$R4, NR3R4, $C_{1-4}$, alkylNR3R4, nitro; NR3COR4, NR5CONR3R4, NR3SO$_2$R4, $C_{1-4}$alkylNR3COR4, $C_{1-4}$alkylNR5CONR3R4, $C_{1-4}$alkylNR3SO$_2$R4; and R3, R4 are each independently H, halogen, $CH_2F$, $CHF_2$, $CF_3$, $C_{1-4}$, alkyl, $C_{1-4}$alkyl cycloalkyl, $C_{1-4}$ cyclohetalkyl, aryl, $C_{1-4}$ alkyl aryl, hetaryl, $C_{1-4}$ alkyl hetaryl, or may be joined to form an optionally substituted 3-8 membered (saturated or unsaturated) ring optionally containing an atom selected from O, S, NR6; and R5 is selected from H, $C_{1-4}$alkyl, halogen, $CH_2F$, $CHF_2$, $CF_3$, aryl or hetaryl; and R6 is selected from H, $C_{1-4}$, alkyl, aryl, hetaryl, $C_{1-4}$ alkyl aryl, $C_{1-4}$ alkyl hetaryl.

R1 is H, $C_{1-4}$ alkyl, $C_{1-6}$ cycloalkyl.

Q is a bond, $CH_2$, $C_{1-4}$ alkyl

A is aryl, hetaryl optionally substituted with 0-3 substituents independently chosen from halogen, $C_{1-4}$ alkyl, $CH_2F$, $CHF_2$, $CF_3$, $OCF_3$, CN, NR8R9, aryl, hetaryl, $C_{1-4}$aryl, $C_{1-4}$hetaryl, $C_{1-4}$ alkylNR8R9, $OC_{1-4}$ alkylNR8R9, nitro, $NR10C_{1-4}NR8R9$, NR8COR9, NR10CONR8R9, NR8SO$_2$R9, CONR8R9, $CO_2R8$ where R8 and R9 are each independently H, $C_{1-4}$ alkyl, aryl or which together form an optionally substituted 4-8 membered ring which may contain a heteroatom selected from O, S, NR11, where R11 is $C_{1-4}$ alkyl, and R10 is selected from H, $C_{1-4}$ alkyl.

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR12R13; and R12, and R13 are each independently H, $C_{1-4}$alkyl, or may be joined to form an optionally substituted 3-8 membered ring optionally containing an atom selected from O, S, NR14 and R14 is selected from H, $C_{1-4}$ alkyl.

In a second aspect the present invention consists in a composition comprising a carrier and at least one compound of the first aspect of the invention.

In a third aspect the present invention consists in a method of treating a protein kinase-associated disease state, the method comprising administering a therapeutically effective amount of at least one compound of the first aspect of the invention or a therapeutically effective amount of a composition of the second aspect of the invention.

In further aspects the present invention provides the use of the compounds described in the preparation of medicaments for the treatment of protein kinase-associated disease states.

DETAILED DESCRIPTION

In a first aspect the present invention consists in a compound of the general formula:

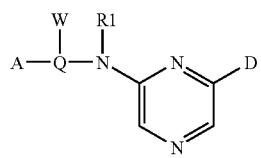

I or pharmaceutically acceptable salts, hydrates; solvates; crystal forms or diastereomers thereof, wherein:

D is a heterocyclic ring selected from:

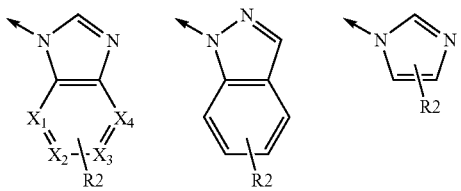

where $X_1, X_2, X_3, X_4$ are optionally substituted carbon, or one of $X_1, X_2, X_3, X_4$ is N; R2 is 0-4 substituents independently chosen from H, halogen, $C_{1-4}$ alkyl, $CH_2F$, $CHF_2$, $CF_3$, $OCF_3$, aryl, hetaryl, $C_{1-4}$alkyl$OC_{1-4}$ alkyl, $C_{1-4}$alkylOaryl, $C_{1-4}$alkylNR3R4, $CO_2R3$, CONR3R4, CONR3SO$_2$R4, NR3R4, $C_{1-4}$alkylNR3R4, nitro, NR3COR4, NR5CONR3R4, NR3SO$_2$R4, $C_{1-4}$alkylNR3COR4, $C_{1-4}$alkylNR5CONR3R4, $C_{1-4}$alkylNR3SO2R4; and R3, R4 are each independently H, halogen, $CH_2F$, $CHF_2$, $CF_3$, $C_{1-4}$alkyl, $C_{1-4}$alkyl cycloalkyl, $C_{1-4}$cyclohetalkyl, aryl, $C_{1-4}$ alkyl aryl, hetaryl, $C_{1-4}$ alkyl hetaryl, or may be joined to form an optionally substituted 3-8 membered (saturated or unsaturated) ring optionally containing an atom selected from O, S, NR6; and R5 is selected from H, $C_{1-4}$ alkyl, halogen, $CH_2F$, $CHF_2$, $CF_3$, aryl or hetaryl; and R6 is selected from H, $C_{1-4}$ alkyl aryl, hetaryl, $C_{1-4}$ alkyl aryl, $C_{1-4}$ alkyl hetaryl.

R1 is H, $C_{1-4}$alkyl, $C_{1-4}$ cycloalkyl.

Q is a bond, $CH_2$, $C_{1-4}$alkyl

A is aryl, hetaryl optionally substituted with 0-3 substituents independently chosen from halogen, $C_{1-4}$ alkyl, $CH_2F$, $CHF_2$, $CF_3$, $OCF_3$, CN, NR8R9, aryl, hetaryl, $C_{1-4}$aryl, $C_{1-4}$hetaryl, $C_{1-4}$ alkylNR8R9, $OC_{1-4}$ alkylNR8R9, nitro, $NR10C_{1-4}NR8R9$, R8COR9, NR10CONR8R9, $NR8SO_2R9$, CONR8R9, $CO_2R8$ where R8 and R9 are each independently H, $C_{1-4}$ alkyl aryl or which together form an optionally substituted 4-8 membered ring which may contain a heteroatom selected from O, S, NR11, where R11 is $C_{1-4}$ alkyl, and R10 is selected from H, $C_{1-4}$alkyl.

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR12R13; and R12, and R13 are each independently H, $C_{1-4}$alkyl, or may be joined to form an optionally substituted 3-8 membered ring optionally containing an atom selected from O, S, NR14 and R14 is selected from H, $C_{1-4}$ alkyl.

In the above description it will be appreciated that:

$C_{1-4}$ alkyl means a straight or branched alkyl chain

Aryl means unsubstituted or optionally substituted phenyl or naphthyl.

Hetaryl means a unsubstituted or optionally substituted 5- or 6-membered heteroaromatic ring containing one or more heteroatoms selected from O, N, S.

Cycloalkyl means a 3-8 membered saturated ring

Cyclohetalkyl means a 3-8 membered saturated ring containing 1-3 heteroatoms selected from O, S, NR13, where R13 is H, $C_{1-4}$ alkyl, aryl, hetaryl.

In a further preferred embodiment the compound is selected from compounds of the general formula II.

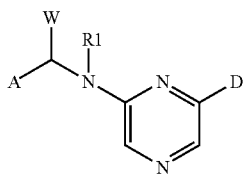

or pharmaceutically acceptable salts, hydrates, solvates, crystal forms or diastereomers thereof, wherein:

D is a heterocyclic ring selected from:

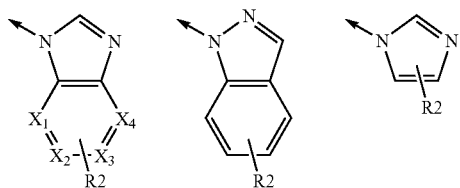

where $X_1$, $X_2$, $X_3$, $X_4$ are optionally substituted carbon, or one of $X_1$, $X_2$, $X_3$, $X_4$ is N; R2 is 0-4 substituents independently chosen from H, halogen, $C_{1-4}$ alkyl, $CH_2F$, $CHF_2$, $CF_3$, $OCF_3$, aryl, hetaryl, $C_{1-4}$alkyl$OC_{1-4}$alkyl, $C_{1-4}$alkylOaryl, $C_{1-4}$alkylNR3R-4, $CO_2R3$, CONR3R4, $CONR3SO_2R4$, nitro, NR3R4, $C_{1-4}$ alkylNR3R4, NR3COR4, NR5CONR3R4, $NR3SO_2R4$, $C_{1-4}$alkylNR3COR4, $C_{1-4}$alkylNR5CONR3R4, $C_{1-4}$alkylNR3SO_2R4$; and R3, R4 are each independently H, halogen, $CH_2F$, $CHF_2$, $CF_3$, $C_{1-4}$ alkyl, $C_{1-4}$ alkyl cycloalkyl, $C_{1-4}$ cyclohetalkyl, aryl, $C_{1-4}$ alkyl aryl, hetaryl, or may be joined to form an optionally substituted 3-8 membered (saturated or unsaturated) ring optionally containing an atom selected from O, S, NR6; and R5 is selected from H, $C_{1-4}$ alkyl, halogen, $CH_2F$, $CHF_2$, $CF_3$, aryl or hetaryl; and R6 is selected from H, $C_{1-4}$ alkyl, aryl, hetaryl, $C_{1-4}$, alkyl aryl, $C_{1-4}$ alkyl hetaryl.

R1 is H, $C_{1-4}$ alkyl, $C_{1-6}$ cycloalkyl.

W is H, $C_{1-4}$ alkyl

A is aryl, hetaryl optionally substituted with 0-3 substituents independently chosen from halogen, $C_{1-4}$ alkyl, $CH_2F$, $CHF_2$, $CF_3$, $OCF_3$, CN, nitro, NR8R9, aryl, hetaryl, $C_{1-4}$aryl, $C_{1-4}$hetaryl, $C_{1-4}$ alkylNR8R9, $OC_{1-4}$ alkylNR8R9, $NR10C_{1-4}NR8R9$, NR8COR9, NR10CONR8R9, $NR8SO_2R9$, CONR8R9, $CO_2R8$ where R8 and R9 are each independently H, $C_{1-4}$ alkyl, aryl or which together form an optionally substituted 4-8 membered ring which may contain a heteroatom selected from O, S, NR11, where R11 is $C_{1-4}$ alkyl, and R10 is selected from H, $C_{1-4}$ alkyl.

In the above description it will be appreciated that:

$C_{1-4}$ alkyl means a straight or branched alkyl chain

Aryl means unsubstituted or optionally substituted phenyl or naphthyl.

Hetaryl means a unsubstituted or optionally substituted 5- or 6-membered heteroaromatic ring containing one or more heteroatoms selected from O, N, S.

Cycloalkyl means a 3-8 membered saturated ring

Cyclohetalkyl means a 3-8 membered saturated ring containing 1-3 heteroatoms selected from O, S, NR13, where R13 is H, $C_{1-4}$ alkyl, aryl, hetaryl.

The compounds of this invention include all conformational isomers (eg. cis and transisomers). The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders that can be treated or prevented by the inhibition of protein kinases, such as JAK comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

In a still further preferred embodiment the compound possesses S chirality at the chiral carbon bearing W, where W is C$_{1-4}$ alkyl. The compound can be used as a purified isomer or as a mixture of any ratio of isomers. It is however preferred that the mixture comprises at least 70%, 80%, 90%, 95%, or 99% of the preferred isomer.

In a still further preferred embodiment the compound is selected from the group consisting of 6-(1H-benzimidazol-1-yl)-N-[(1R)-1-phenylethyl]pyrazin-2-amine, N-benzyl-6-(1H-imidazol-1-yl)pyrazin-2-amine, 6-(1H-benzimidazol-1-yl)-N-[(1S)-1-(4-methoxyphenyl)ethyl]pyrazin-2-amine, N-(4-Fluorobenzyl)-6-(1H-imidazol-1-yl)pyrazin-2-amine, 6-(1H-benzimidazol-1-yl)-N-[(1S)-1-(4-bromophenyl)ethyl]pyrazin-2-amine, 6-(1H-Imidazol-1-yl)-N-[(1R)-1-phenylethyl]pyrazin-2-amine, 1-(6-{[(1S)-1-phenylethyl]amino}pyrazin-2-yl)-1H-benzimidazole-6-carboxamide, 6-(1H-Benzimidazol-1-yl)-N-benzylpyrazin-2-amine, 1-(6-{[(1S)-1-phenylethyl]amino}pyrazin-2-yl)-1H-benzimidazole-5-carboxamide, 6-(1H-Benzimidazol-1-yl)-N-(4-fluorobenzyl)pyrazin-2-amine, 6-{5-[(Morpholino-1-yl)carbonyl]-1H-benzimidazol-1-yl}-N-[(1S)-1-phenylethyl]pyrazin-2-amine, 6-(1H-imidazo[4,5-b]pyridin-1-yl)-N-[(1R)-1-phenylethyl]pyrazin-2-amine, 6-{6-[(Morpholino-1-yl)carbonyl]-1H-benzimidazol-1-yl}-N-[(1S)-1-phenylethyl]pyrazin-2-amine, 6-(1H-imidazol-1-yl)-N-(4-morpholin-4-ylphenyl)pyrazin-2-amine, N-[1-(6-{[(1S)-1-Phenylethyl]amino}pyrazin-2-yl)-1H-benzimidazol-6-yl]cyclopropanecarboxamide, N-[1-(6-{[(1S)-1-phenylethyl]amino}pyrazin-2-yl)-1H-benzimidazol-5-yl]nicotinamide, N-[1-(6-{[(1S)-1-Phenylethyl]amino}pyrazin-2-yl)-1H-benzimidazol-5-yl]cyclopropanecarboxamide, 6-(1H-Benzimidazol-1-yl)-N-[(1R)-1-phenylethyl]pyrazin-2-amine, 6-[6-(4,5-dihydro-1,3-oxazol-2-yl)-1H-benzimidazol-1-yl]-N-[(1S)-1-phenylethyl]pyrazin-2-amine, N-[(1R)-1-Phenylethyl]-6-(4-phenyl-1H-imidazol-1-yl)pyrazin-2-amine, 1-[6-{[(1S)-1-phenylethyl]amino}pyrazin-2-yl]-N-(2-hydroxyethyl)-1H-benzimidazole-6-carboxamide, N-[1-(6-{[(1S)-1-phenylethyl]amino}pyrazin-2-yl)-1H-benzimidazol-6-yl]methanesulfonamide, N-[1-(6-{[(1S)-1-phenylethyl]amino}pyrazin-2-yl)-1H-benzimidazol-5-yl]methanesulfonamide, N-[1-(6-{[(1S)-1-phenylethyl]amino}pyrazin-2-yl)-1H-benzimidazol-5-yl]isonicotinamide, 6-(1H-Imidazol-1-yl)-N-[(1S)-1-phenylethyl]pyrazin-2-amine, N-[1-(6-{[(1S)-1-phenylethyl]amino}pyrazin-2-yl)-1H-benzimidazol-6-yl]isonicotinamide, 6-(1H-Benzimidazol-1-yl)-N-[(1S)-1-phenylethyl]pyrazin-2-amine, 6-[5-(4,5-dihydro-1,3-oxazol-2-yl)-1H-benzimidazol-1-yl]-N-[(1S)-1-phenylethyl]pyrazin-2-amine, 1-[6-{[(1S)-1-phenylethyl]amino}pyrazin-2-yl]-N-(2-hydroxyethyl)-1H-benzimidazole-5-carboxamide, 6-(5-Methyl-1H-benzimidazol-1-yl)-N-[(1S)-1-phenylethyl]pyrazin-2-amine, N-[1-(6-{[(1S)-1-phenylethyl]amino}pyrazin-2-yl)-1H-benzimidazol-6-yl]nicotinamide, N-methyl-1-(6-{[(1S)-1-phenylethyl]amino}pyrazin-2-yl)-1H-benzimidazole-5-carboxamide, N-[1-(6-{[(1S)-1-phenylethyl]amino}pyrazin-2-yl)-1H-benzimidazol-6-yl]2,2-dimethylpropanamide, N-methyl-1-(6-{[(1S)-1-phenylethyl]amino}pyrazin-2-yl)-1H-benzimidazole-6-carboxamide, N-[1-(6-{[(1S)-1-phenylethyl]amino}pyrazin-2-yl)-1H-benzimidazol-5-yl]-2,2-dimethylpropanamide, 1-(6-{[(1S)-1-Phenylethyl]amino}pyrazin-2-yl)-1H-benzimidazol-5-amine, 2-Methoxy-N-[1-(6-{[(1S)-1-phenylethyl]amino}pyrazin-2-yl)-1H-benzimidazol-5-yl]acetamide, 1-(6-{[(1S)-1-phenylethyl]amino}pyrazin-2-yl)-1H-benzimidazol-6-amine, 2-Methoxy-N-[1-(6-{[(1S)-1-phenylethyl]amino}pyrazin-2-yl)-1H-benzimidazol-6-yl]acetamide, N-Benzyl-1-[6-([(1S)-1-phenylethyl]amino)pyrazin-2-yl]-1H-benzimidazole-5-carboxamide, N-[1-(6-{[(1S)-1-phenylethyl]amino}pyrazin-2-yl)-1H-benzimindazol-5-yl]pyrazine-2-carboxamide, 1-(6-{[(1S)-1-Phenylethyl]amino}pyrazin-2-yl)-N-phenyl-1H-benzimidazole-5-carboxamide, N-[1-(6-{[(1S)-1-phenylethyl]amino}pyrazin-2-yl)-1H-benzimidazol-6-yl]pyrazine-2-carboxamide, N-[1-(6-{[(1S)-1-phenylethyl]amino}pyrazin-2-yl)-1H-benzimidazol-6-yl]acetamide, 6-{5-[(4-Methylpiperazin-1-yl)methyl]-1H-benzimidazol-1-yl}-N-[(1S)-1-phenylethyl]pyrazin-2-amine, N-[1-(6-{[(1S)-1-Phenylethyl]amino}pyrazin-2-yl)-1H-benzimidazol-5-yl]acetamide, [1-(6-{[(1S)-1-Phenylethyl]amino}pyrazin-2-yl)-1H-benzimidazol-5-yl]methanol, N-[1-(6-{[(1S)-1-phenylethyl]amino}pyrazin-2-yl)-1H-benzimidazol-6-yl]benzamide, [1-(6-{[(1S)-1-phenylethyl]amino}pyrazin-2-yl)-1H-benzimidazol-6-yl]methanol, N-[1-(6-{[(1S)-1-phenylethyl]amino}pyrazin-2-yl)-1H-benzimidazol-5-yl]benzamide, 1-(6-{[(1S)-1-phenylethyl]amino}pyrazin-2-yl)-N-[2-(dimethylamino)ethyl]-1H-benzimidazole-5-carboxamide, 1-[6-{[(1S)-1-Phenylethyl]amino}pyrazin-2-yl]-N-(pyridin-3-ylmethyl)-1H-benzimidazol-5-amine, tert-butyl(2S)-2-({[1-(6-{[(1S)-1-phenylethyl]amino}pyrazin-2-yl)-1H-benzimidazol-5-yl]amino}carbonyl)pyrrolidine-1-carboxylate, 6-(3H-imidazo[4,5-c]pyridin-3-yl)-N-[(1S)-1-phenylethyl]pyrazin-2-amine, 6-(1H-benzimidazol-1-yl)-N-[1-(4-fluorophenyl)ethyl]pyrazin-2-amine, 6-(1H-imidazo[4,5-c]pyridin-1-yl)-N-[(1S)-1-phenylethyl]pyrazin-2-amine, 6-(1H-benzimidazol-1-yl)-N-[(1S)-1-(4-pyridin-3-ylphenyl)ethyl]pyrazin-2-amine, (2S)-N-[1-(6-{[(1S)-1-phenylethyl]amino}pyrazin-2-yl)-1H-benzimidazol-5-yl]pyrrolidine-2-carboxamide, N-[(1S)-1-phenylethyl]-6-(5-pyridin-4-yl-1H-benzimidazol-1-yl)pyrazin-2-amine, N-[(1S)-1-phenylethyl]-6-(5-pyridin-3-yl-1H-benzimidazol-1-yl)pyrazin-2-amine, 6-(5-bromo-1H-benzimidazol-1-yl)-N-[(1S)-1-phenylethyl]pyrazin-2-amine, N-[3-(1H-imidazol-1-yl)propyl]-1-[6-([(1S)-1-phenylethyl]amino)pyrazin-2-yl]-1H-benzimidazole-6-carboxamide, N-1H-benzimidazole-6-carboxamide, N-(3-morpholin-4-ylpropyl)-1-[6-([(1S)-1-phenylethyl]amino)pyrazin-2-yl]-1H-benzimidazole-6-carboxamide, N-(3-morpholin-4-ylpropyl)-1-[6-([(1S)-1-phenylethyl]amino)pyrazin-2-yl]-1H-benzimidazole-5-carboxamide, N-[1-(6-{[(1S)-1-phenylethyl]amino}pyrazin-2-yl)-1H-benzimidazol-5-yl]piperidine-3-carboxamide, 6-(1H-benzimidazol-1-yl)-N-[(1S)-1-pyridin-3-ylethyl]pyrazin-2-amine, 6-(1H-benzimidazol-1-yl)-N-[(1S)-1-(1,1'-biphenyl-4-yl)ethyl]pyrazin-2-amine N-[1-(6-{[(1S)-1-phenylethyl]amino}pyrazin-2-yl)-1H-benzimidazol-5-yl]benzenesulfonamide and 6-(1H-benzimidazol-1-yl)-N-[(1S)-1-(1,1'-biphenyl-4-yl)ethyl]pyrazin-2-amine.

In a second aspect the present invention consists in a composition comprising a carrier and at least one compound of the first aspect of the invention.

In a third aspect the present invention consists in a method of treating a protein kinase-associated disease state, the method comprising administering a therapeutically effective amount of at least one compound of the first aspect of the invention or a therapeutically effective amount of a composition of the second aspect of the invention.

In a preferred embodiment, the disease state involves a receptor tyrosine kinase selected from the group consisting of EGF, HER2, HER3, HER4, IR, IGF-1R, IRR, PDGFR.alpha., PDGFR.beta., CSFIR, C-Kit, C-fms,Flk-1R, Flk4, KDR/Flk-1, Flt-1, FGFR-1R, FGFR-2R, FGFR-3R and FGFR-4R.

In another preferred embodiment, the disease state involves a cellular tyrosine kinase selected from the group consisting of Src, Frk, Btk, Csk, Abl, ZAP70, Fes/Fps, Fak, Ack, Yes, Fyn, Lyn, Lck, Blk, Hck, Fgr and Yrk.

In a further preferred embodiment, the disease state involves a tyrosine kinase selected from the group consisting of JAK1, JAK2, JAK3 and TYK2.

In a yet further preferred embodiment, the disease state involves a serine/threonine kinase selected from the group consisting of ERK2, c-Jun, p38 MAPK, PKA, PKB, PKC, a cyclin-dependent kinase, CDK1, CDK2, CDK3, CDK4, CDK5, CDK6, CDK7, CDK8, CDK9, CDK10, and CDK11.

In a preferred embodiment of the present invention the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV 1, Varicella-Zoster Virus (VZV), Human Papilloma Virus (HPV), Cancer, such as Leukemia, Lymphoma and Prostate Cancer.

As used herein the term "protein kinase-associated disease state" refers to those disorders which result from aberrant protein kinase activity, in particular JAK activity and/or which are alleviated by inhibition of one or more of these enzymes. In further aspects the present invention provides the use of the compounds described in the preparation of medicaments for the treatment of protein kinase-associated disease states.

As used herein the term "JAK", "JAK kinase" or "JAK family" refers to protein tyrosine kinases which possess the characterizing features of JAK1, JAK2, JAK3 and TYK as described herein.

The present invention provides pharmaceutical compositions comprising at least one of the compounds of the present invention capable of treating a protein kinase-associated disorder, such as a JAK associated disorder, in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The compounds may also administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which JAK inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatibles with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In additions sterile, fixed oils are conventionally employed as a solvent or suspending medium. For this propose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD401 g and CD8gp39), inhibitors, such as nuclear translocation inhibitors, of NF-kappa B function, such as deoxyspergualin (DSG), cholesterol biosynthesis inhibitors such as HMC CoA reductase inhibitors (lovastatin and simvastatin), non-steroidal antiinflammatory drugs (NSAIDs) such as ibuprofen, aspirin, acetaminophen and cyclooxygenase inhibitors such as rofecoxib, steroids such as prednisolone or dexamethasone, gold compounds, antiproliferative agents such as methotrexate, FK506 (tacrolimus, Prograf), mycophenolate mofetil, cytotoxic drugs such as azathioprine, VP-16, etoposide, fludarabine, cisplatin and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex; diet mode and time of administration, rate of excretion, drug combination, the severity of the particular condition, and the host undergoing therapy.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will now be described by reference to the following non-limiting Examples.

Materials and Methods:

Compound Synthesis

Compounds are generally prepared in a 2-step process starting from 2,6-dichloropyrazine.

The first step is a nucleophilic aromatic substitution to generate a monoamino-monohalo intermediate. (Scheme 1).

Scheme 1

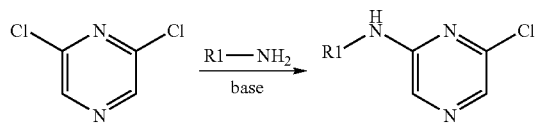

The nucleophilic aromatic substitution is typically carried out by addition of a primary amine to the di-halogenated heterocycle in a solvent such as ethanol, isopropanol, tert-butanol, dioxane, THF, DMF, toluene or xylene. The reaction is typically performed at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalysed amination reaction. Typical catalysts for such transformations include $Pd(OAc)_2/P(t-Bu)_3$, $Pd_2(dba)_3/BINAP$ and $Pd(OAc)_2/BINAP$.

The amines employed in the first step of the synthesis of these compounds are obtained commercially or are prepared using methods well known to those skilled in the art. Of particular interest are α-methylbenzylamines which are obtained commercially or may be prepared through reduction of oximes (Scheme 2). Typical reductants include lithium aluminium hydride, hydrogen gas in the presence of catalytic palladium on charcoal, Zn in the presence of hydrochloric acid, sodium borohydride in the presence of a Lewis acid such as $TiCl_3$, $ZrCl_4$, $NiCl_2$ and $MoO_3$, or sodium borohydride in conjunction with Amberlyst H15 ion exchange resin and LiCl. The oximes are obtained in one-step from the corresponding ketones through condensation with hydroxylamine. This reaction is generally performed in a protic solvent such as water or ethanol, at temperatures from 0° C. to reflux. The hydroxylamine is generally used in the form of its hydrochloride salt, and therefore the reaction is performed in the presence of a base such as sodium hydroxide. The ketones employed as starting materials are generally obtained commercially or via procedures well known to those skilled in the art.

Scheme 2

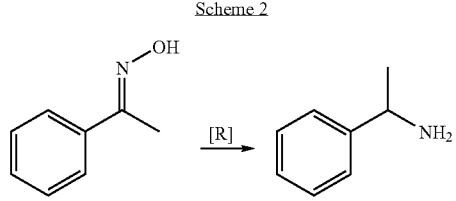

α-Methyl benzylamines of high optical purity may be prepared from chiral α-methyl benzyl alcohols using methods well known to those skilled in the art. Such methods include derivatisation of the hydroxyl as a mesylate or tosylate and displacement with a nitrogen nucleophile, such as phthalimide or azide which can then converted to the primary amine using conventional synthetic methods; or, displacement of the hydroxyl with a suitable nitrogen nucleophile under Mitsunobu conditions. The chiral α-methyl benzyl alcohols may be obtained through chiral reduction of the corresponding ketones. Chiral reducing methods are now well known in organic chemistry and include enzymatic processes, asymmetric hydrogenation procedures and chiral oxazaborolidines.

The second step of the synthesis involves a nucleophilic aromatic substitution reaction of the monochloro- mono-amino pyrazine with imidazole, benzimidazole or indazole. The reaction is typically performed using a salt of the imidazole, benzimidazole or indazole in solvents such as tetrahydrofuran, dimethylformamide, toluene, or xylene from room temperature toe reflux. The imidazole, benzimidazole or indazole salt is prepared by reaction with a metal hydride such as sodium or potassium hydride or by reaction with caesium carbonate. Alternatively, a metal-catalysed coupling reaction can be used to introduce the imidazole, benzimidazole or indazole ring. The reaction is typically performed using a base such as caesium carbonate, rubidium carbonate, potassium carbonate, sodium tert-butoxide or potassium phosphate in a solvent such as xylene, toluene, and DMF from room temperature to reflux. Auxiliary reagents such as phase transfer agents (e.g. cetrimonium bromide) or copper complexing agents (e.g. phenanthroline) may also be employed in the reaction.

The imidazole, benzimidazole or indazole components used in this reaction are obtained commercially or are prepared from commercially available imidazoles, benzimidazoles or indazoles via techniques well known to those skilled in the art.

Alternatively, an imidazole, benzimidazole or indazole derivative may be reacted with the mono-amino mono-chloro pyrazine and the subsequent product further derivatised using methods well known to those skilled in the art.

Representative syntheses are reported below.

EXAMPLE 1

6-Chloro-N-[(1R)-1-phenylethyl]pyrazin-2-amine

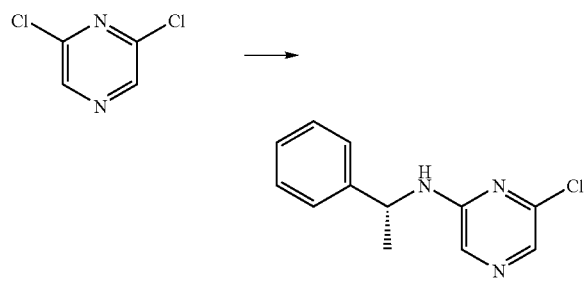

A solution of R-α-methylbenzylamine (3.64 g, 30.0 mmol) and 2,6-dichloropyrazine (1.50 g, 10.0 mmol) in dioxane (5 mL) was heated at reflux under $N_2$ for 48 hours. The solvent was removed and the product crystallised from toluene-hexane.

$^1$H-n.m.r. (CDCl$_3$) δ1.59 (d, 3H, J=6.9 Hz, CH$_3$), 4.88 (q, 1H, J=6.6 Hz, CH), 5.13 (br s, 1H, NH), 7.27-7.36 (m, 5H, ArH), 7.64 (s, 1H, pyraz-H), 7.79 (s, 1H, pyraz-H).

EXAMPLE 2

6-(1H-Imidazol-1-yl)-N-[(1R)-1-phenylethyl]pyrazin-2-amine

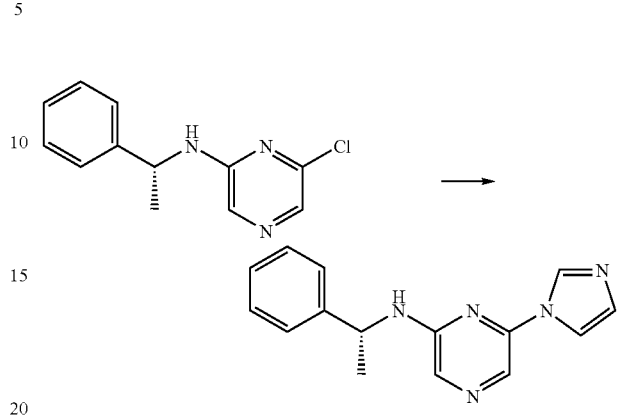

To a stirred solution of imidazole (82 mg 1.2 mmol) in anhydrous DMF (5 mL) at 0° C. under $N_2$ was added sodium hydride (58 mg, 60 dispersion in oil, 1.45 mmol). The mixture was stirred at 0° C. for 10 min and at RT for 30 min. To this mixture was added a solution of 6-chloro-N-[(1R)-1-phenylethyl]pyrazin-2-amine (280 mg, 1.2 mmol) in DMF (5 mL). The mixture was then stirred at RT for 62 h followed by heating at reflux for 18 h. The DMF was removed under reduced pressure and the residue diluted with chloroform. The organic layer was washed with water, dried (Na$_2$SO$_4$) and the solvent removed under reduced pressure to furnish the crude product. Column chromatography using dichloromethane-methanol (19:1→10.1) as eluant separated recovered starting material from product (177 mg, 56%).

$^1$H-n.m.r. (CDCl$_3$) δ1.62 (d, 3H, J=6.9 Hz, CH$_3$), 4.97 (m, 1H, CH), 5.46 (d, 1H, J=6.0 Hz, NH), 7.17 (s, 1H, imid-H), 7.23-7.40 (m, 5H, Ph-H), 7.47 (s, 1H, imid-H), 7.76 (s, 1H, pyraz-H), 7.91 (s, 1H, pyraz-H), 8.20 (s, 1H, imid-H).

m/z (ES) 266 (M$^+$+H), 162, 105.

EXAMPLE 3

6-Chloro-N-(4-morpholin-4-ylphenyl)pyrazin-2-amine

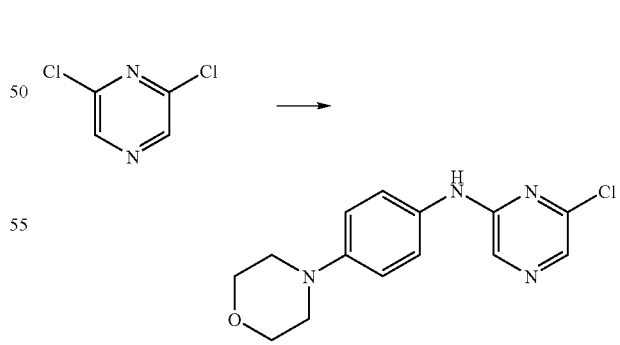

In a procedure analogous to example 1, reaction of 4-morpholinoaniline (2.15 g, 12.1 mmol) and 2,6-dichloropyrazine (0.756 g, 5.03 mmol) furnished the product (0.54 g, 37%).

$^1$H-n.m.r. (CDCl$_3$) δ3.25 (br s, 4H, CH$_2$), 3.99 (br s, 4H, CH$_2$), 7.05-7.17 (m, 2H, ArH), 7.42-7.54 (m, 2H, ArH), 7.94 (s, 1H, pyraz-H), 8.04 (s, 1H, pyraz-H), 8.06 (s, 1H, NH).

EXAMPLE 4

6-Chloro-N-(4-fluorobenzyl)pyrazin-2-amine

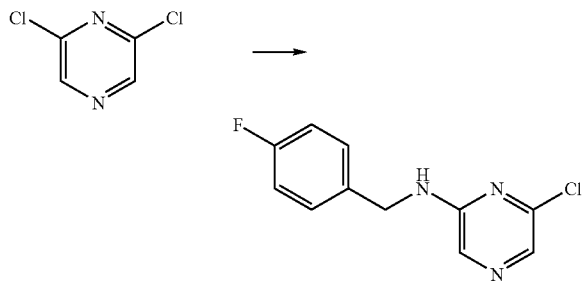

In a procedure analogous to example 1, reaction of 4-fluorobenzylamine (3.75 g, 30.0 mmol) and 2,6-dichloropyrazine (1.49 g, 10.0 mmol) furnished the product (2.35 g, 99%).

$^1$H-n.m.r. (CDCl$_3$) δ 4.53(s, 2H, CH$_2$), 5.08(br s, 1H, NH), 7.01-7.07(m, 2H, ArH), 7.30-7.34(m, 2H, ArH), 7.77(s, 1H, pyraz-H), 7.83(s, 1H, pyraz-H)

EXAMPLE 5

6-(1H-Imidazol-1-yl)-N-(4-morpholin-4-ylphenyl)pyrazin-2-amine

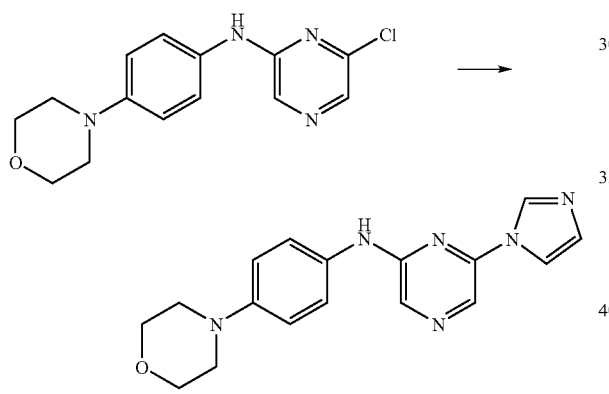

In a procedure analogous to example 2, reaction of 6-chloro-N-(4-morpholin-4-ylphenyl)pyrazin-2-amine (100 mg, 0.34 mmol) and imidazole (126 mg, 0.38 mmol) furnished the product (37 mg, 34%).

$^1$H-n.m.r. (CDCl$_3$) δ3.18 (br s, 4H, 2CH$_2$), 3.87-3.91 (m, 4H, 2CH$_2$), 6.77 (s, 1H, imid-H), 6.94-6.98 (m, 2H, ArH), 7.36 (d, 2H, J=8.7 Hz, ArH), 7.62 (br s, 1H, imid-H), 8.03 (s, 1H, pyraz-H), 8.08 (s, 1H, pyraz-H), 8.39 (br s, 1H, imid-H).

m/z (ES) 323 (M$^+$+H).

EXAMPLE 6

N-(4-Fluorobenzyl)-6-(H-imidazol-1-yl)pyrazin-2-amine

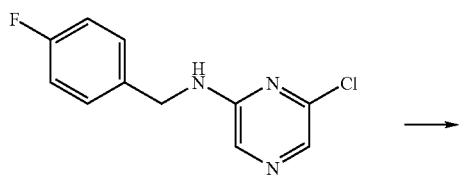

-continued

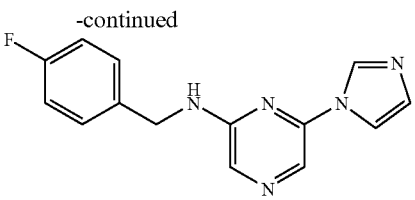

In a procedure analogous to example 2, reaction of 6-chloro-N-(4-fluorobenzyl)pyrazin-2-amine (240 mg, 1.01 mmol) and imidazole (76 mg, 1.11 mmol) furnished the product (210 mg, 65%).

$^1$H-n.m.r. (CDCl$_3$) δ 4.59 (d, 2H, J=5.7 Hz, CH$_2$), 5.23 (t-like, 1H, NH), 7.03-7.08 (m, 2H, ArH), 7.20 (s, 1H, imid-H), 7.32-7.37 (m, 2H, ArH), 7.55 (s, 1H, imid-H), 7.85 (s, 1H, pyraz-H), 8.00 (s, 1H, pyraz-H), 8.29 (s, 1H, imid-H).

m/z (ES)270 (M$^+$+H).

EXAMPLE 7

6-(2-Methyl-1H-imidazol-1-yl)-N-[(1R)-1-phenylethyl]pyrazin-2-amine

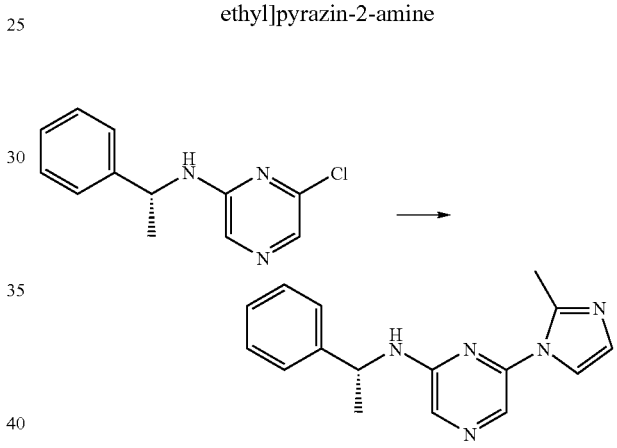

In a procedure analogous to example 2, reaction of 6-chloro-N-[(1R)-1-phenylethyl]pyrazin-2-amine (150 mg, 0.64 mmol) and 2-methylimidazole (58 mg, 0.71 mmol) furnished the product (172 mg, 40%).

$^1$H-n.m.r. (CDCl$_3$) δ1.59 (d, 3H, J=6.8 Hz, CH$_3$), 2.43 (s, 3H, CH$_3$), 4.98 (m, 1H, CH), 5.45 (br s, 1H, NH), 6.98 (d, 1H, J=1.3 Hz, imid-H), 7.17 (d, 1H, J=1.3 Hz, imid-H), 7.22-7.35 (m, 5H, ArH), 7.82 (s, 1H, pyraz-H), 7.84 (s, 1H, pyraz-H).

m/z (ES) 280 (M$^+$+H).

EXAMPLE 8

N-(4-Fluorobenzyl)-6-(2-methyl-1H-imidazol-1-yl)pyrazin-2-amine

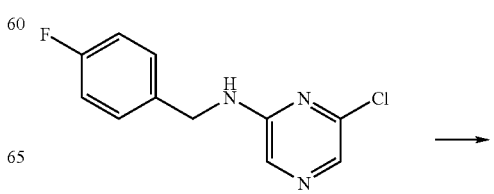

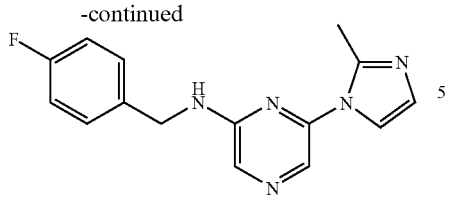

In a procedure-analogous to example 2 reaction of 6-chloro-N-(4-fluorobenzyl)pyrazin-2-amine (150 mg, 0.63 mmol) and 2-methylimidazole (57 mg, 0.69 mmol) furnished the product (42 mg, 23%).

$^1$H-n.m.r. (CDCl$_3$) δ 2.56 (s, 3H, CH$_3$), 4.57 (d, J=5.7 Hz, 1H, CH$_2$), 5.34 (br s, 1H, NH), 7.01-7.07 (m, 3H, Ar—H), 7.26 (s, 1H, imid-H), 7.29-7.34 (m, 2H, ArH), 7.92 (s, 2H, pyraz-H).

m/z (ES) 284 (M$^+$+H).

EXAMPLE 9

N-(4-Fluorobenzyl)-6-(4-methyl-1H-imidazol-1-yl)pyrazin-2-amine and N-(4-Fluorobenzyl)-6-(5-methyl-1H-imidazol-1-yl)pyrazin-2-amine

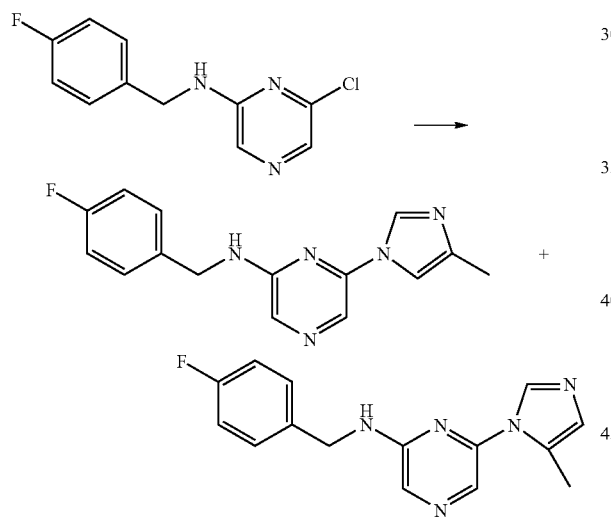

In a procedure analogous to example 2, reaction of 2-(4-fluorobenzylamino)-6-chloro-pyrazine (190 mg, 0.80 mmol) and 4-methylimidazole (72 mg, 0.88 mmol) furnished the following products: 4-methyl derivative (100 mg, 44%); 5-methyl derivative (19 mg, 8%).

(4-methyl derivative) $^1$H-n.m.r. (CDCl$_3$) δ 2.31 (s, 3H, CH$_3$), 4.58 (d, 2H, J=5.7 Hz, CH$_2$), 5.40 (br s, 1H, NH), 6.92 (s, 1H, imid-H), 7.00-7.08 (m, 2H, ArH), 7.25 (s, 1H, imid-H5), 7.31-7.36 (m, 2H, ArH), 7.84 (s, 1H, pyraz-H5), 7.93 (s, 1H, pyraz-H3), 8.24 (br s, 1H, imid-H2).

m/z (ES) 284 (M$^+$+H).

(5-methyl derivative) $^1$H-n.m.r. (CDCl$_3$) δ 2.34 (s, 3H, CH$_3$), 4.57 (d, 2H, J=5.7 Hz, CH$_2$), 5.44 (br s, 1H, NH), 6.92 (s, 1H, imid-H), 7.00-7.07 (m, 2H, ArH), 7.28-7.34 (m, 2H, ArH), 7.93 (s, 1H, pyraz-H), 7.95 (s, 1H, pyraz-H), 7.98 (br s, 1H, imid-H).

m/z (ES) 284 (M$^+$+H).

EXAMPLE 10

N-[(1R)-1-Phenylethyl]-6-(4-phenyl-1H-imidazol-1-yl)pyrazin-2-amine

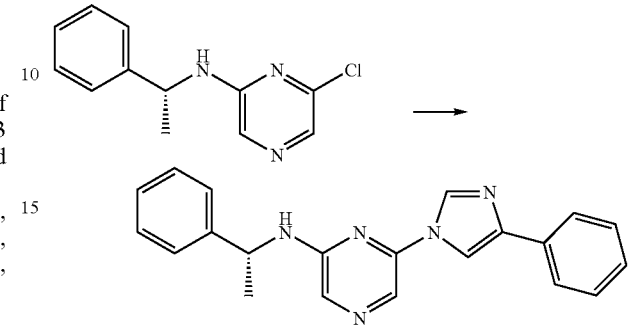

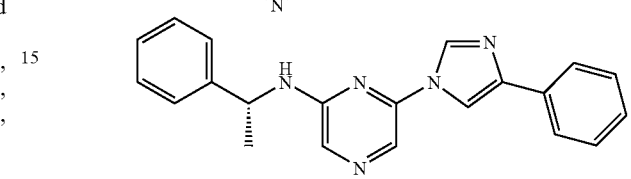

In a procedure analogous to example 2, reaction of 6-chloro-N-[(1R)-1-phenylethyl]pyrazin-2-amine (180 mg, 0.77 mmol) and 4-phenylimidazole (122 mg, 0.85 mmol) furnished the product (176 mg, 67%).

$^1$H-n.m.r. (CDCl$_3$) δ 1.63 (d, 3H, J=6.9 Hz, CH$_3$), 4.93-5.02 (m, 1H, CH), 5.26 (d, 1H, J=6.0 Hz, NH), 7.25-7.44 (m, 8H, ArH), 7.72 (d, 1H, J=1.2 Hz, imid-H), 7.77 (s, 1H, pyraz-H), 7.82-7.86 (m, 2H, ArH), 7.92 (s, 1H, pyraz-H), 8.22 (s, 1H, imid-H).

m/z (ES) 342 (M$^+$+H).

EXAMPLE 11

N-Benzyl-6-chloropyrazin-2-amine

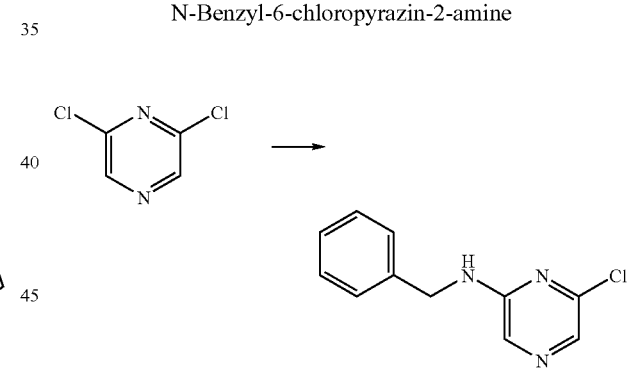

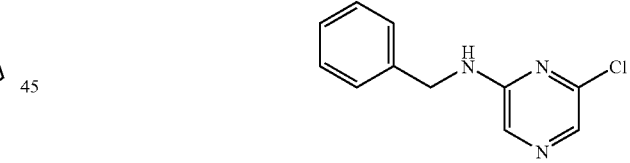

In a procedure analogous to example 1, reaction of benzylamine (3.21 g, 30.0 mmol) and 2,6-dichloropyrazine (1.49 g, 10.0 mmol) furnished the product (2.15 g, 98%).

$^1$H-n.m.r. (CDCl$_3$) δ 4.55 (d, 2H, J=5.7 Hz, CH$_2$), 7.28-7.40 (m, 5H, ArH), 7.76 (s, 1H, pyraz-H), 7.83 (s, 1H, pyraz-H).

EXAMPLE 12

6-(1H-Benzimidazol-1-yl)-N-benzylpyrazin-2-amine

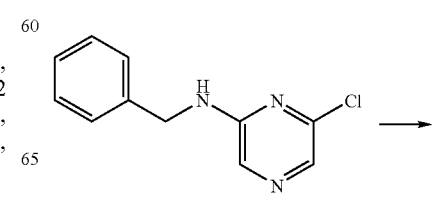

-continued

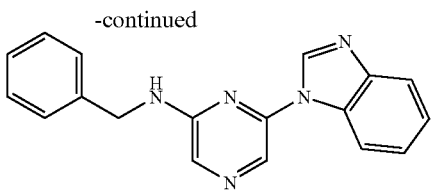

To a stirred solution of benzimidazole (130 mg, 1.1 mmol) in anhydrous DMF (5 mL) at 0° C. under N₂ was added sodium hydride (56 mg, 60% dispersion in oil, 1.45 mmol) in portions over 2 min. The mixture was stirred at 0° C. for 15 min and at RT for 60 min. To this was added a solution of (6-chloro-pyrazin-2-yl)-(1-benzyl)-amine (220 mg) in DMF (5 mL) and the resulting mixture was then heated at reflux for 18 h. The DMF was removed under reduced pressure and the residue diluted with choroform. The organic layer was washed with water, dried (Na₂SO₄) and the solvent removed under reduced pressure to furnish the crude product. Column chromatography using dichloromethane-methanol (20:1→10:1) as eluant separated the product (100 mg).

¹H-n.m.r. (CDCl₃) δ 4.66 (d, 2H, J=5.7 Hz, CH₂), 5.56 (m, 1H, NH), 7.29-7.39 (m, 7H, Ar—H), 7.78-7.89 (m, 2H, Ar—H), 7.92 (s, 1H, pyraz-H), 8.16 (s, 1H, pyraz-H), 8.48 (s, 1H, benzimid-H2).

m/z (ES) 302 (M⁺+H).

EXAMPLE 13

6-(1H-Benzimidazol-1-yl)-N-[(1R)-1-phenylethyl]pyrazin-2-amine

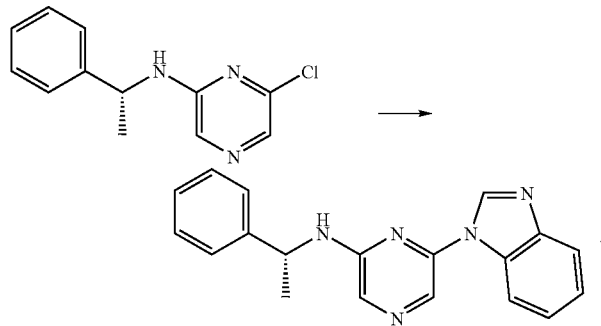

In a procedure analogous to example 12, reaction of 6-chloro-N-[(1R)-1-phenylethyl]pyrazin-2-amine (240 mg, 1.03 mmol) and benzimidazole (130 mg; 1.10 mmol) furnished the product (187 mg, 59%).

¹H-n.m.r. (CDCl₃) δ1.63 (d, 3H, J=6.6 Hz, CH₃), 4.98-5.20 (m, 1H, CH), 5.58 (d, 1H, J=6.0 Hz, NH), 7.25-7.42 (m, 6H, Ph-H, benzimid-H), 7.70 (dd, 1H, J=7.2, 1.0 Hz, benzimid-H), 7.82 (dd, 1H, J=8.0, 1.2 Hz, benzimid-H), 7.87 (s, 1H, pyraz-H), 8.11 (s, 1H, pyraz-H), 8.38 (s, 1H, benzimid-H).

m/z (ES) 315 (M⁺+H), 212, 105.

EXAMPLE 14

6-(1H-Benzimidazol-1-yl)-N-[(1S)-1-phenylethyl]pyrazin-2-amine

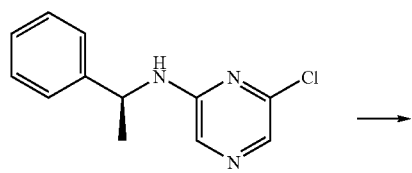

In a procedure analogous to example 12, reaction of 6-chloro-N-[(1S)-1-phenylethyl]pyrazin-2-amine (140 mg, 0.60 mmol) and benzimidazole (78 mg, 0.66 mmol) furnished the product (71 mg, 38%).

¹H-n.m.r. (CDCl₃) δ1.57 (d, 3H, J=6.9 Hz, CH₃), 4.95 (m, 1H, CH), 5.29 (d, 1H, J=6.0 Hz, NH), 7.19-7.35 (m, 7H, Ph-H, benzimid-H), 7.63-7.66 (m, 1H, benzimid-H), 7.74-7.77 (m, 1H, benzimid-H), 7.78 (s, 1H, pyraz-H), 8.06 (s, 1H, pyraz-H), 8.31 (s, 1H, benzimid-H).

m/z (ES) 316 (M⁺+H), 212, 105

EXAMPLE 15

6-(1H-Benzimidazol-1-yl)-N-(4-morpholin-4-ylphenyl)pyrazin-2-amine

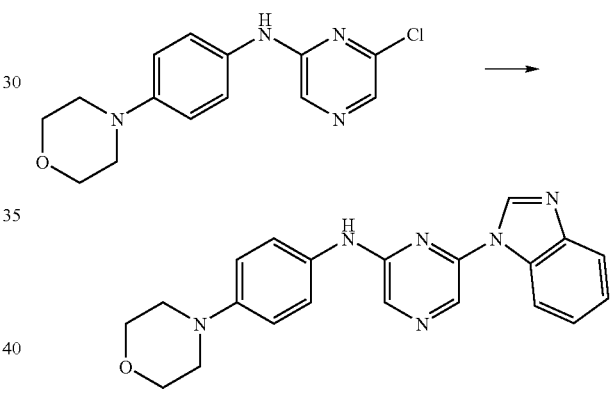

In a procedure analogous to example 12, reaction of 6-chloro-N-(4-morpholin-4-ylphenyl)pyrazin-2-amine (150 mg, 0.52 mmol) and benzimidazole (67 mg, 0.57 mmol) furnished the product (60 mg, 31%).

¹H-n.m.r. (CDCl₃) δ 3.19 (br s, 4H, 2CH₂), 3.90 (t, 4H, J=4.6 Hz, 2CH₂), 6.69 (s, 1H, NH), 6.98 (d, 2H, J=8.4 Hz, ArH), 7.37-7.41 (m, 4H, ArH), 7.87-7.90 (m, 1H, ArH), 8.00-8.03 (m, 1H, ArH), 8.08 (s, 1H, pyraz-H), 8.31 (s, 1H, pyraz-H), 8.59 (s, 1H, benzimid-H2).

m/z-(ES) 373 (M⁺+H).

EXAMPLE 16

6-(1H-Benzimidazol-1-yl)-N-(4-fluorobenzyl)pyrazin-2-amine

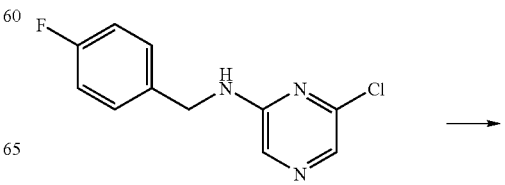

-continued

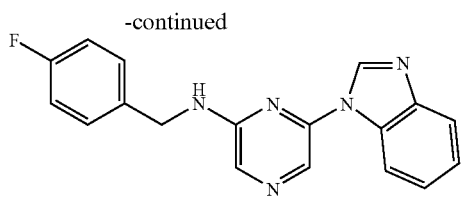

In a procedure analogous to example 12, reaction of 6-chloro-N-(4-fluorobenzyl)pyrazin-2-amine (240 mg, 1.01 mmol) and benzimidazole (130 mg, 1.1 mmol) furnished the product (170 mg, 53%).

$^1$H-n.m.r. (CDCl$_3$) δ4.64 (d, 2H, J=5.7 Hz, CH$_2$), 5.46 (br s, 1H, NH), 7.06 (m, 2H, ArH), 7.30-7.38 (m, 4H, ArH), 7.82-7.88 (m, 2H, ArH), 7.93 (s, 1H, pyraz-H), 8.20 (s, 1H, benzimid-H), 8.49 (s, 1H, pyraz-H).

m/z (ES) 320 (M$^+$+H).

EXAMPLE 17

6-(1H-imidazo[4,5-b]pyridin-1-yl)-N-[(1S)-1-phenylethyl]pyrazin-2-amine and 6-(3H-imidazo[4,5-b]pyridin 3-yl)-N-[(1S)-1-phenylethyl]pyrazin-2-amine

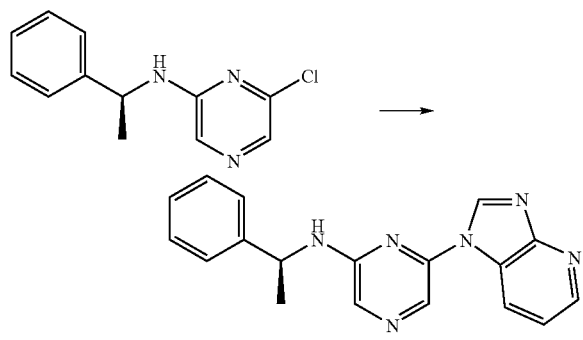

In a procedure analogous to example 12, reaction of 6-chloro-N-[(1S)-1-phenylethyl]pyrazin-2-amine (240 mg, 1.03 mmol) and 4-azabenzimidazole (130 mg, 1.09 mmol) furnished the product (7 mg, 2%) as a 1:1 mixture of regioisomers.

$^1$H-n.m.r. (as 1:1 mixture) (CDCl$_3$) δ1.54 (d, 3H, CH$_3$), 1.63 (d, 3H, CH$_3$), 4.63 (br s, 1H, NH), 4.82-4.91 (m, 1H, CH), 4.95-5.04 (m, 1H, NH), 5.16 (m, 1H, NH), 7.07 (s, 1H, ArH), 7.22-7.43 (m, 16H, ArH), 7.87 (s, 1H, ArH), 8.11 (dd, 1H, J=8.1, 1.5 Hz, ArH), 8.48 (dd, 1H, J=4.8, 1.2 Hz, ArH), 8.80 (s, 1H, ArH).

m/z (ES) 317 (M$^+$+H).

EXAMPLE 18

6-(5-Methyl-1H-benzimidazol-1-yl)-N-[(1S)-1-phenylethyl]pyrazin-2-amine and 6-(6-methyl-1H-benzimidazol-1-yl)-N-[(1S)-phenylethyl]pyrazin-2-amine

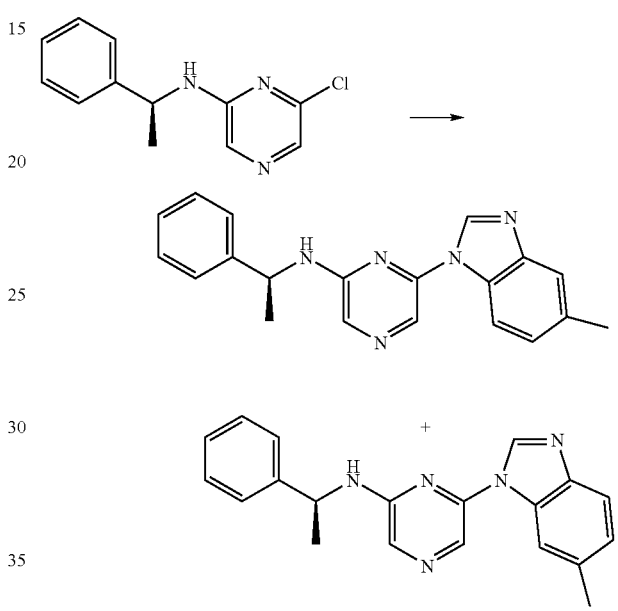

In a procedure analogous, to example 12, reaction of 6-chloro-N-[(1S)-1-phenylethyl]pyrazin-2-amine (91 mg, 0.39 mmol) and 5-methylbenzimidazole (57 mg, 0.43 mmol) furnished the product (61 mg, 148%) as a 1:1 mixture.

$^1$H-n.m.r. (as 1:1 mixture) (CDCl$_3$) δ1.65 (d, 3H, CH$_3$), 1.66 (d, 3H, CH$_3$), 2.49 (s, 3H, CH$_3$), 2.50 (s, 3H, CH$_3$), 5.01 (m, 1H, CH), 5.04 (m, 1H, CH), 5.56 (d, 1H, NH), 5.62 (d, 1H, NH), 7.27-7.45 (m, 10H, Ph-H), 7.56-7.85 (m, 4H, benzimid-H), 7.94 (s, 1H, pyraz-H), 7.97 (s, 1H, pyraz-H), 8.02 (s, 2H, benzimid-H), 8.16 (s, 1H, pyraz-H), 8.17 (s, 1H, pyraz-H), 8.59 (s, 1H, benzimid-H), 8.70 (s, 1H, benzimid-H).

m/z (ES) 330 (M$^+$+H).

EXAMPLE 19

6-(2-Methyl-1H-benzimidazol-1-yl)-N-[(1S)-1-phenylethyl]pyrazin-2-amine

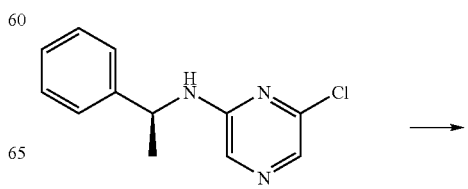

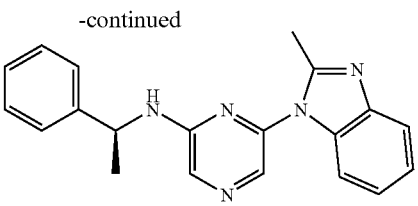

In a procedure analogous to example 12, reaction of 6-chloro-N-[(1S)-1-phenylethyl]pyrazin-2-amine (120 mg, 0.51 mmol) and 2-methyl-benzimidazole (75 mg, 0.57 mmol) furnished the product (18 mg, 11%).

$^1$H-n.m.r. (CDCl$_3$) δ1.63 (d, 3H, J=6.9 Hz, CH$_3$), 2.59 (s, 3H, CH$_3$), 4.93 (m, 1H, CH), 5.89 (br s, 1H, NH), 7.16-7.49 (m, 7H, ArH), 7.93 (d, 2H, J=8.1 Hz, Ar—H), 8.00 (br s, 1H, pyraz-H), 8.23 (br s, 1H, pyraz-H).

m/z (ES) 330 (M$^+$+H).

EXAMPLE 20

N-(2-Hydroxyethyl)-1H-benzimidazole-5-carboxamide

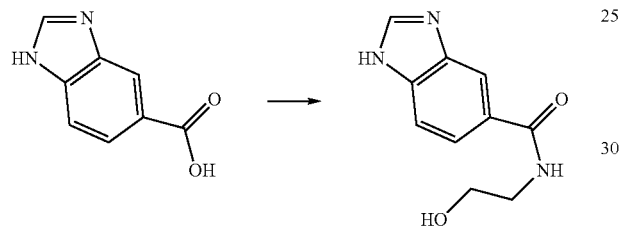

To a stirred suspension of benzimidazole-5-carboxylic acid (0.40 g, 2.50 mmol) in benzene (8 mL) was added thionyl chloride (2 mL) dropwise at room temperature. The whole mixture was then heated under reflux for 5 h. Benzene and thionyl chloride was evaporated off under reduced pressure, and the obtained acid chloride was suspended in tetrohydrofuran. To this was the added 2-hydroxyethyl amine dropwise at 0° C., and the resultant mixture was then stirred at room temperature overnight. The solvent was then decanted, and the residue was washed with diethyl ether (40 mL). The residue oil was then treated with cold water (5 mL), and the aqueous solution was carefully decanted. This step was repeated, and now the amide was obtained as a pale brown solid, 0.19 g (37%).

$^1$H-n.m.r. (CDCl$_3$) δ 3.30-3.37 (m, 2H, CH$_2$), 3.51-3.55 (m, 2H, CH$_2$), 4.69 (s, 1H, OH), 7.59 (d, 1H, J=8.1 Hz, ArH), 7.73 (d, 1H, J=8.4 Hz, ArH), 8.13 (br s, 1H, NH), 8.30 (s, 1H, H-4), 8.35 (br s, 1H, H-2), 12.47 (br s, 1H, CONH).

EXAMPLE 21

1-[6-{[(1S)-1-phenylethyl]amino}pyrazin-2-yl]-N-(2-hydroxyethyl)-1H-benzimidazole-5-carboxamide

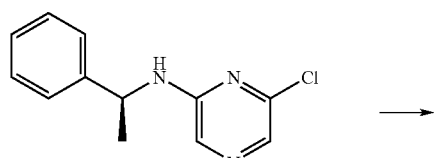

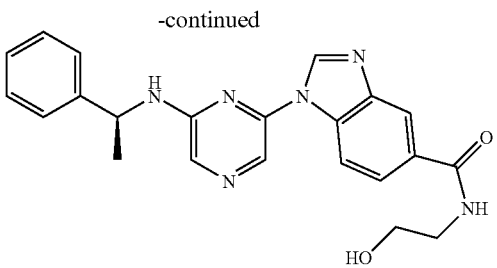

In a procedure analogous to example 12, reaction of 6-chloro-N-[(1S)-1-phenylethyl]pyrazin-2-amine (91 mg, 0.39 mmol) and benzimidazole 5-carboxylic acid (2-hydroxyethyl)amide (88 mg, 0.43 mmol) furnished the product which was purified by column chromatography (22 mg, 14%).

$^1$H-n.m.r. (CDCl$_3$) δ1.63 (d, 3H, J=6.9 Hz, CH$_3$), 3.68 (2H, dt, J=5.1 Hz, CH$_2$NH), 3.91 (2H, t, J=5.1 Hz, CH$_2$OH), 4.98 (m, 1H, CH), 5.50 (d, 1H, J=6.0 Hz, NH), 7.15 (1H, t, J=5.1 Hz, CONH), 7.28-7.41 (m, 5H, Ar—H), 7.60 (d, 1H, J=8.4 Hz, benzimid-H), 7.73 (d, 1H, J=8.4 Hz, benzimid-H), 7.88 (s, 1H, pyraz-H), 8.05 (s, 1H, pyraz-H), 8.20 (s, 1H, benzimid-H), 8.40 (s, 1H, benzimid-H). m/z (ES) 403 (M$^+$+H).

EXAMPLE 22

[1-(6-{[1S)-1-Phenylethyl]amino}pyrazin-2-yl)-1H-benzimidazol-5-yl]methanol and [1-(6{[(1S)-1-phenylethyl]amino}pyrazin-2-yl)-1H-benzimidazol-6-yl]methanol

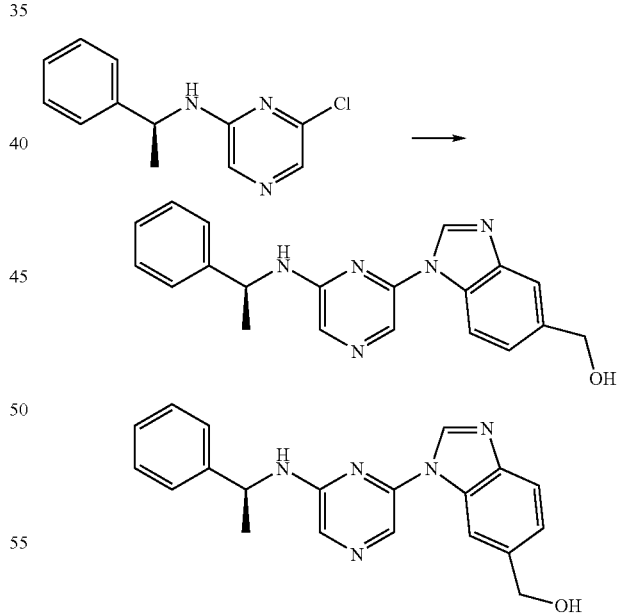

In a procedure analogous to example 12, reaction of 6-chloro-N-[(1S)-1-phenylethyl]pyrazin-2-amine (1.07 g, 4.6 mmol) and 5-hyroxymethyl benzimidazole (0.68 g, Y 4.60 mmol) furnished the two products separated by column chromatography: 5-hyroxymethyl isomer (34 mg, 2%); 6-hydroxymethyl isomer (36 mg, 2%).

(5-hydroxymethyl isomer) $^1$H-n.m.r. (CDCl$_3$) δ1.65 (d, 3H, J=6.9 Hz, CH$_3$), 4.82 (s, 2H, CH$_2$OH), 5.03 (m, 1H, CH), 5.26 (d, 1H, J=6.0 Hz, NH), 7.25-7.40 (m, 6H, Ar—H), 7.68 (d, 1H, J=8.4 Hz, benzimid-H), 7.81 (s, 1H, benzimid-H), 7.85 (s, 1H, pyraz-H), 8.12 (s, 1H, pyraz-H), 8.39 (s, 1H, benzimid-H). m/z (ES) 346 (M$^+$+H).

(6-hydroxymethyl isomer) $^1$H-n.m.r. (CDCl$_3$) δ1.63 (d, 3H, J=609 Hz, CH$_3$), 4.79 (s, 2H, CH$_2$OH), 5.03 (m, 1H, CH), 5.42 (d, 1H, J=6.3 Hz, NH), 7.25-7.42 (m, 6H, Ar—H), 7.78 (d, 1H, J=8.4 Hz, benzimid-H), 7.81 (s, 1H, pyraz-H), 7.90 (s, 1H, benzimid-H), 8.10 (s, 1H, pyraz-H), 8.35 (s, 1H, benzimid-H). m/z (ES) 346 (M$^+$+H).

EXAMPLE 23

N-Methyl-1H-benzimidazole-5-carboxamide

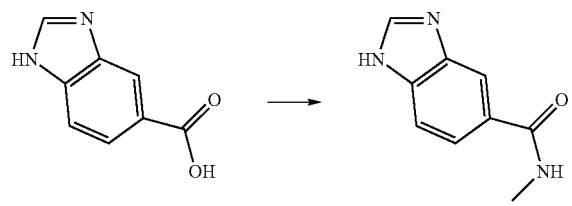

In a procedure analogous to example 20, reaction of benzimidazole-5-carboxylic acid and aqueous methylamine furnished the product in 67% yield.

$^1$H-n.m.r. (CDCl$_3$) δ 2.79 (s, 3H, CH$_3$), 7.59 (d, 1H, J=8.4 Hz, H-6), 7.71 (dd, 1H, J=8.4, 1.2 Hz, H-7), 8.10 (s, 1H, H-4), 8.29 (s, 1H, H-2), 8.36 (br s, 1H, NH), 12.56 (br s, 1H, CONH).

EXAMPLE 24

N-Methyl-1-(6-{[(1S)-1-phenylethyl]amino}pyrazin-2-yl)-1H-benzimidazole-5-carboxamide and 1-N-Methyl-1-(6-{[(1S)-1-phenylethyl]amino}pyrazin-2-yl)-1H-benzimidazole-6-carboxamide

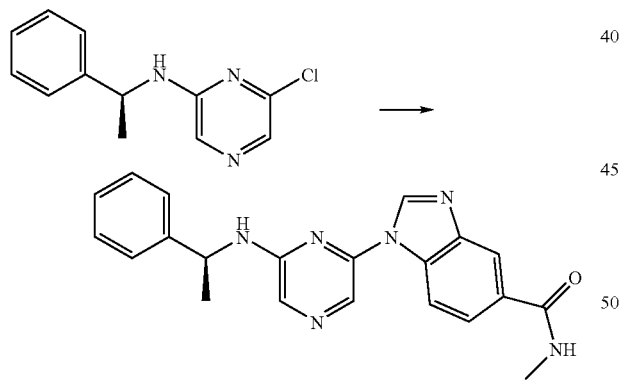

In a procedure analogous to example 12, reaction of 6-chloro-N-[(1S)-1-phenylethyl]pyrazin-2-amine (91 mg, 0.39 mmol) and 5-carboxybenzimidazole N-methyl amide (75 mg, 0.43 mmol) furnished the two products separated by column chromatography: 5-isomer (23 mg, 16%); 6-isomer (38 mg 26%).

(5-isomer) $^1$H-n.m.r. (CDCl$_3$) δ1.67 (d, 3H, J=6.9 Hz, CH$_3$), 3.06 (d, 3H, J=4.5 Hz, NCH$_3$), 5.01 (m, 1H, CH), 5.58 (br s, 1H, NH), 6.43 (br s, 1H, CONH), 7.30-7.43 (m, 5H, Ph-H), 7.71 (d, 1H, J=8.4 Hz, benzimid-H), 7.84-7.88 (m, 2H, benzimid-H, pyraz-H), 8.19 (s, 1H, pyraz-H), 8.53 (s, 1H, benzimid-H), 8.57 (s, 1H, benzimid-H).

m/z (ES) 373 (M$^+$+H).

(6-isomer). $^1$H-n.m.r. (CDCl$_3$) δ1.65 (d, 3H, J=6.9 Hz, CH$_3$), 3.07 (d, 3H, J=4.5 Hz, NCH$_3$), 5.02 (m, 1H, CH), 5.31 (d, 1H, J=4.8 Hz, NH), 6.30 (br s, 1H, CONH), 7.31-7.41 (m, 5H, Ph-H), 7.68 (d, 1H, J=8.4 Hz, benzimid-H), 7.81 (d, 1H, J=8.4 Hz, benzimid-H), 7.92 (s, 1H, pyraz-H), 8.13 (s, 1H, pyraz-H), 8.18 (s, 1H, benzimid-H), 8.49 (s, 1H, benzimid-H).

m/z (ES) 373 (M$^+$+H).

EXAMPLE 25

1-(6-{[(1S)-1-Phenylethyl]amino}pyrazin-2-yl)-1H-benzimidazol-5-amine and 1-(6-{[(1S)-1-phenylethyl]amino}pyrazin-2-yl)-1H-benzimidazol-6-amine

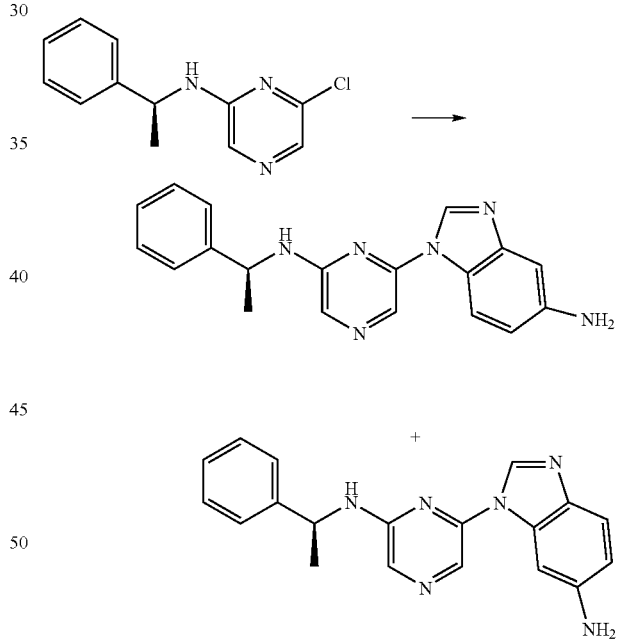

To a stirred solution of 5-amino-benzimidazole (290 mg, 2.2 mmol) in anhydrous DMF (10 mL) under N$_2$ was added caesium carbonate (980 mg). The resulting mixture was stirred at 70 for 60 min. To this was added a solution of 6-chloro-N-[(1S)-1-phenylethyl]pyrazin-2-amine (470 mg) in DMF (5 mL) and the resulting mixture was then heated at reflux for 48 h. The DMF was removed under reduced pressure and the residue diluted with chloroform. The organic layer was washed with aqueous Na$_2$CO$_3$, dried (Na$_2$SO$_4$) and the solvent removed under reduced pressure to furnish the crude product. Column chromatography using dichloromethane-methanol (95:5→92:8) as eluant separated two fractions from unreacted starting material. The higher Rf fraction was assigned as the 6-isomer (276 mg, 42%). ¹H-n.m.r. (CDCl₃) δ1.64 (d, 3H, J 6.9 Hz, CH₃), 2.90 (br s, 2H, NH₂), 5.05 (m, 1H, CH), 5.21 (d, 1H, NH), 6.70 (dd, 1H, J=8.7, 2.1 Hz, benzimid-H), 6.97 (d, 1H, J=1.8 Hz, benzimid-H), 7.28-7.43 (m, 5H, Ph-H), 7.58 (d, 1H, J=8.4 Hz, benzimid-H), 7.84 (s, 1H, pyraz-H), 8.08 (s, H, pyraz-H), 8.21 (s, 1H, benzimid-H). m/z (ES) 331 (M⁺+H). The lower fraction was assigned as the 5-isomer (170 mg, 26%), ¹H-n.m.r. (CDCl₃) δ1.64 (d, 3H, J=6.9 Hz, CH₃), 2.85 (br s, 2H, NH₂), 5.01 (m, 1H, CH), 5.19 (d, 1H, NH), 6.70 (dd, 1H, 8.7, 2.1 Hz, benzimid-H), 7.11 (d, 1H, J=1.8 Hz, benzimid-H), 7.29-7.40 (m, 5H, Ph-H), 7.51 (d, 1H, J=8.7 Hz, benzimid-H), 7.81 (s, 1H, pyraz-H), 8.10 (s, 1H, pyraz-H), 8.32 (s, 1H, benzimid-H).

m/z (ES) 331 (M⁺+H).

EXAMPLE 26

N-Benzyl-1H-benzimidazole-5-carboxamide

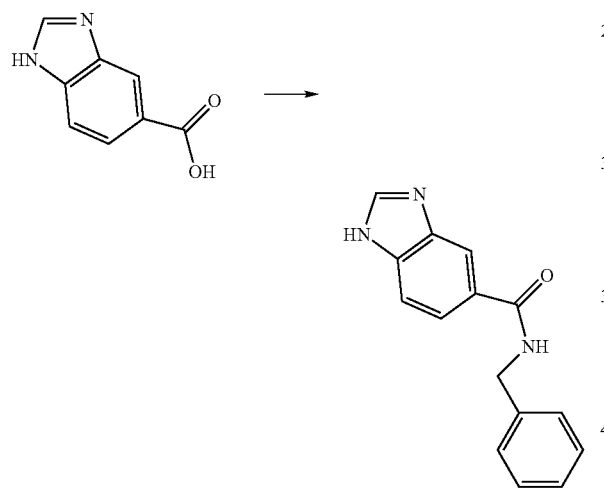

In a procedure analogous to example 20, reaction of benzimidazole-5-carboxylic acid (400 mg, 2.50 mmol) and benzylamine furnished the product (410 mg, 66%).

¹H-n.m.r. (CDCl₃) δ 4.56 (d, 2H, J=5.8 Hz, CH₂), 7.13-7.31 (m, 5H, Ph-H), 7.59 (d, 1H, J=8.5 Hz, H-6), 7.79 (dd, 1H, J=8.5 Hz, H-7), 7.96 (br s, 1H, CONH), 8.21 (s, 1H, H-4), 8.29 (s, 1H, H-2).

EXAMPLE 27

N-Benzyl-1-[6-([(1S)-1-phenylethyl]amino)pyrazin-2-yl]-1H-benzimidazole-5-carboxamide and N-Benzyl-1-[6-([(1S)-1-phenylethyl]amino)pyrazin-2-yl-1H-benzimidazole-6-carboxamide

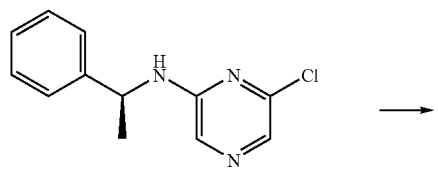

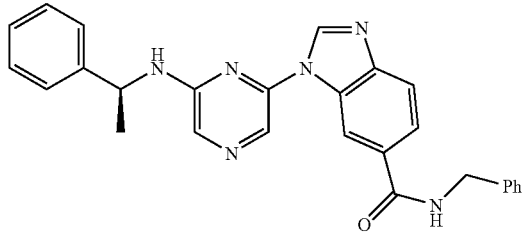

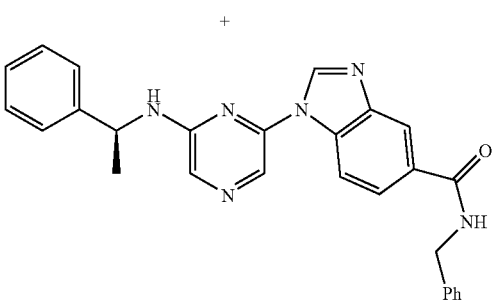

In a procedure analogous to example 25, reaction of 6-chloro-N-[(1S)-1-phenylethyl]pyrazin-2-amine (91 mg, 0.39 mmol) and N-benzyl-1H-benzimidazole-5-carboxamide (108 mg, 0.43 mmol) furnished the product (132 mg, 75%) as a 3:1 mixture of regioisomers.

¹H-n.m.r. (as 3:1 mixture) (CDCl₃) δ1.62 (d, 3H, J=6.9 Hz, CH₃), 1.63 (d, 3H, J=CH), 5.55 (d, 1H, NH), 5.61 (d, 1H, NH), 6.80 (t-like, 1H, (CONH), 6.92 (t-like, 1H, CONH), 7.22-7.40 (m, Ph-H, Ph-H), 7.66 (d, 1H, J=8.4 Hz, benzimid-H), 7.71 (d, 1H, J=8.4 Hz, benzimid-H), 7.80-7.85 (m, benzimid-H) 7.91 (s, 1H, benzimid-H), 8.05 (s, 1H, pyraz-H), 8.13 (s, 1H, pyraz-H), 8.25 (s, 1H, benzimid-H), 8.38 (s, 1H, pyraz-H), 8.46 (s, 1H, benzimid-H), 8.59 (s, 1H, pyraz-H).
m/z (ES) 449 (M⁺+H).

EXAMPLE 28

N-Phenyl-1H-benzimidazole-5-carboxamide

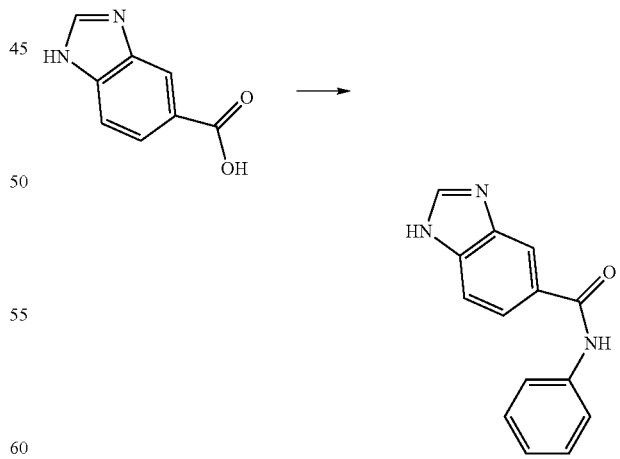

In a procedure analogous to example 20, reaction of benzimidazole-5-carboxylic acid (400 mg, 5.50 mmol) and aniline (510 mg, 5.50 mmol) furnished the product (370 mg, 63%).

¹H-n.m.r. (CDCl₃) δ6.83 (m, 1H, Ar—H), 7.08 (m, 2H, Ar—H), 7.53-7.74 (m, 4H, Ar—H), 8.13-8.31 (m, 2H, Ar—H+CONH), 9.57 (s, 1H, H-2).

EXAMPLE 29

1-(6-{[(1S)-1-Phenylethyl]amino}pyrazin-2-yl)-N-phenyl-1H-benzimidazole-5-carboxamide and 1-(6-{[(1S)-1-phenylethyl]amino}pyrazin-2-yl)-N-phenyl-1H-benzimidazole-6-carboxamide

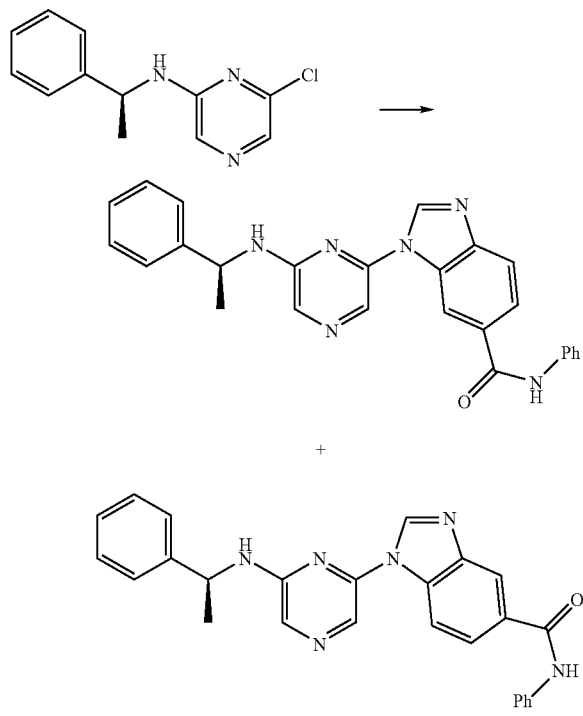

In a procedure analogous to example 25, reaction of 6-chloro-N-[(1S)-1-phenylethyl]pyrazin-2-amine (91 mg, 0.39 mmol) and N-phenyl-1H-benzimidazole-5-carboxamide, (102 mg, 0.43 mmol) furnished the product (100 mg, 59%) as a 2:1 mixture of regioisomers.

$^1$H-n.m.r. (as 2:1 mixture) (CDCl$_3$) δ1.61 (d, 3H, J=6.9 Hz, CH$_3$), 1.62 (d, 3H, J=6.9 Hz, CH$_3$), 4.94-5.03 (m, CH, CH), 5.55 (d, 1H, NH), 5.62 (d, 1H, NH), 7.18-7.45 (m, Ph-H, Ph-H), 7.61-7.83 (m, benzimid-H and Ph-H)), 7.85 (s, 1H, pyraz-H), 7.90 (s, 1H, pyraz-H), 8.06 (s, 1H, pyraz-H), 8.12 (s, 1H, pyraz-H), 8.33 (s, 1H, benzimid-H), 8.36 (s, 1H, benzimid-H), 8.46 (s, 1H, benzimid-H), 8.49 (s, 1H, CONH), 8.52 (s, 1H, CONH), 8.57 (s, 1H, benzimid-H).

m/z (ES) 435 (M$^+$+H).

EXAMPLE 30

5-[(4-Methylpiperazin-1-yl)carbonyl]-1H-benzimidazole

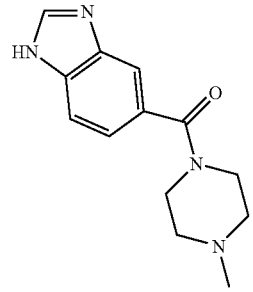

In a procedure analogous to example 20, reaction of benzimidazole-5-carboxylic acid (400 mg, 2.50 mmol) and N-methylpiperazine (550 mg, 5.0 mmol) furnished the product (380 mg, 63%).

$^1$H-n.m.r. (CDCl$_3$) δ2.33 (s, 3H, CH$_3$), 2.44(br s, 4H, CH$_2$), 3.70 (br s, 4H, CH$_2$), 7.25 (s, 1H, ArH), 7.66 (br s, 1H, ArH), 7.87 (s, 1H, ArH), 11.88 (s, 1H, H-2).

m/z (ES) 245 (M$^+$+H).

EXAMPLE 31

6-{5-[(4-Methylpiperazin-1-yl)carbonyl]-1H-benzimidazol-1-yl}-N-[(1S)-1-phenylethyl]pyrazin-2-amine and 6-{6-[(4-Methylpiperazin-1-yl)carbonyl]-1H-benzimidazol-1-yl}-N-[(1S)-1-phenylethyl]pyrazin-2-amine

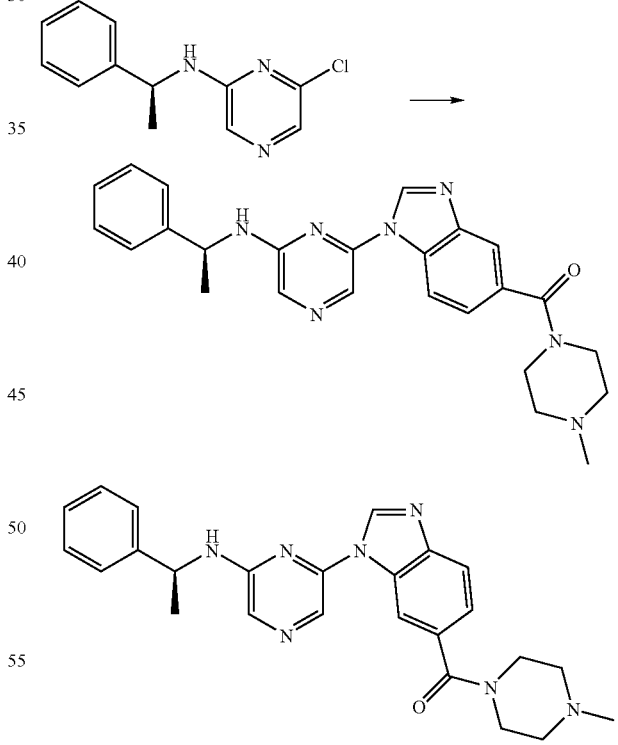

In a procedure analogous to example 25, reaction of 6-chloro-N-[(1S)-1-phenylethyl]pyrazin-2-amine (91 mg, 0.39 mmol) and 5-[(4-methylpiperazin-1-yl)carbonyl]-1H-benzimidazole (105 mg, 0.43 mmol) furnished the product as a mixture of regioisomers which were separated by column chromatography: 6-isomer (58 mg, 34%); 5-isomer (68 mg, 40%).

(5 isomer) $^1$H-n.m.r. (CDCl$_3$) δ1.63 (d, 3H, J=6.9 Hz, CH$_3$), 2.33 (s, 3H, NCH$_3$), 2.44 (br s, 4H, CH$_2$), 3.67 (br s, 4H, CH$_2$), 5.01 (m, 1H, CH), 5.48 (d, 1H, =6.0 Hz, NH), 7.26-7.38 (m, 6H, Ar—H), 7.65 (d, 1H, J=8.4 Hz, benzimid-H), 7.85 (s, 1H, benzimid-H), 7.89 (s, 1H, pyraz-H), 8.09 (s, 1H, pyraz-H), 8.41 (s, 1H, benzimid-H).

m/z (ES) 442 (M$^+$+H).

(6 isomer) $^1$H-n.m.r. (CDCl$_3$) δ1.63 (d, 3H, J=6.9 Hz, CH$_3$), 2.31 (s, 3H, NCH$_3$), 2.43 (br s, 4H, CH$_2$), 3.4-3.9 (br m, 4H, CH$_2$), 4.99 (m, 1H, CH), 5.54 (d, 1H, J=6.0 Hz, NH), 7.23-7.39 (m, 6H, Ar—H), 7.83-7.85 (m, 2H, Ar—H, pyraz-H), 8.07 (s, 1H, benzimid-H), 8.12 (s, 1H, pyraz-H), 8.44 (s, 1H, benzimid-H). m/z (ES) 442 (M$^+$+H).

EXAMPLE 32

N-[1-(6-{[(1S)-1-Phenylethyl]amino}pyrazin-2-yl)-1H-benzimidazol-5-yl]acetamide

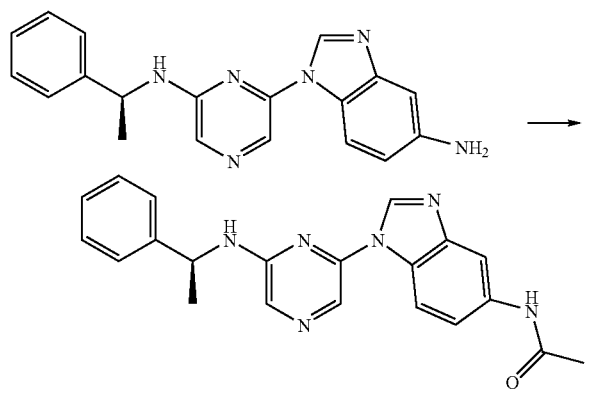

To a stirred solution of 2-(S-α-methylbenzylamino)-6-(5-amino-benzimidazo-1-yl)-pyrazine (66 mg, 0.2 mmol) in anhydrous THF (2 mL) under N$_2$ was added triethylamine (41 mg, 0.4 mmol). The solution was cooled at 0° C. and to this was added acetyl chloride (17 mg, 0.22 mmol) and the resulting mixture then stirred at RT. After 18 h the solution was poured into water (30 mL) and the product extracted into chloroform (2×20 mL). The combined organic layers were dried (Na$_2$SO$_4$) and the solvent removed under reduced pressure to furnish the crude product as a pale yellow solid. Column chromatography using dichloromethane-methanol (200:15) as eluant separated the product as a pale yellow solid (38 mg).

$^1$H-n.m.r. (CDCl$_3$) δ1.63 (d, 3H, J=6.6 Hz, CH$_3$), 2.21 (s, 3H, CH$_3$), 5.00 (m, 1H, CH), 5.43 (d, 1H, J=5.7 Hz, NH), 7.27-7.38 (m, 5H, ArH), 7.49 (d, 1H, J=9.0 Hz, benzimid-H), 7.61 (d, 1H, J=9.0 Hz, benzimid-H), 7.74 (br s, 1H, CONH), 7.84 (s, 1H, pyraz-H), 7.90 (s, 1H, benzimid-H), 8.11 (s, 1H, pyraz-H), 8.36 (s, 1H, benzimid-H).

m/z (ES) 373. (M$^+$+H).

EXAMPLE 33

N-[1-(6-{[(1S)-1-phenylethyl]amino}pyrazin-2-yl)-1H-benzimidazol-6-yl]acetamide

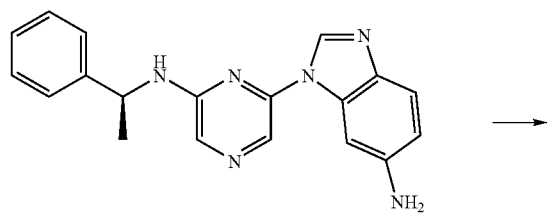

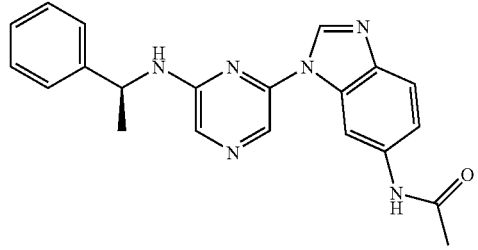

In a procedure analogous to example 32, reaction of 2-(S-α-methylbenzylamino)-6-(6-amino-benzimidazo-1-yl)-pyrazine (66 mg, 0.20 mmol) and acetyl chloride (17 mg, 0.22 mmol) furnished the product (70 mg, 94%) after chromatography.

$^1$H-n.m.r. (CDCl$_3$) δ1.65 (d, 3H, J=6.9 Hz, CH$_3$), 2.22 (s, 3H, CH$_3$), 5.07 (m, 1H, CH), 5.29 (d, 1H, J=6.3 Hz, NH), 7.28-7.43 (m, 6H, ArH, benzimid-H), 7.72 (d, 1H, J=8.7 Hz, benzimid-H), 7.84 (s, 1H, pyraz-H) 8.12 (s, 1H, pyraz-H), 8.27 (s, 1H, benzimid-H), 8.34 (s, 1H, benzimid-H).

m/z (ES) 373 (M$^+$+H).

EXAMPLE 34

N-[1-(6-{[(1S)-1-phenylethyl]amino}pyrazin-2-yl)-1H-benzimidazol-5-yl]benzamide

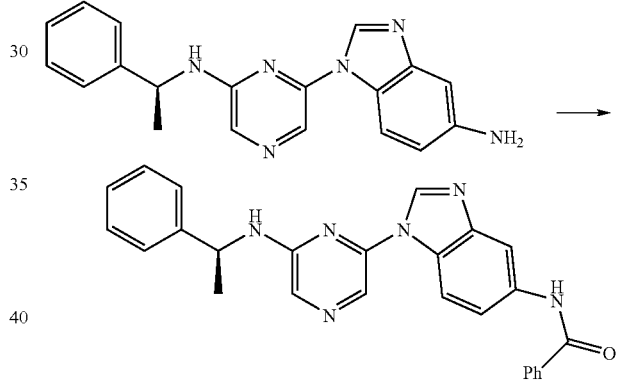

In a procedure analogous to example 32, reaction of 1-(6-{[(1S)-1-phenylethyl]amino}pyrazin-2-yl)-1H-benzimidazol-5-amine (33 mg, 0.10 mmol) and benzoyl chloride (14 mg 0.10 mmol) furnished the product (23 mg, 53%) after chromatography.

$^1$H-n.m.r. (CDCl$_3$) δ 1.64 (d, 3H, J=6.8 Hz, CH$_3$), 5.02 (m, 1H, CH), 5.33 (d, 1H, J=4.5 Hz, NH), 7.27-7.68 (m, 10H, ArH) 7.85 (s, 1H, pyraz-H), 7.90-7.93 (m, 2H, benzimid-H), 8.03 (s, 1H, benzimid-H), 8.06 (s 1H, CONH), 8.10 (s, 1H, pyraz-H), 8.38 (s, 1H, benzimid-H).

m/z (ES) 435 (M$^+$+H).

EXAMPLE 35

N-[1-(6-{[(1S)-1-phenylethyl]amino}pyrazin-2-yl)-1H-benzimidazol-6-yl]benzamide

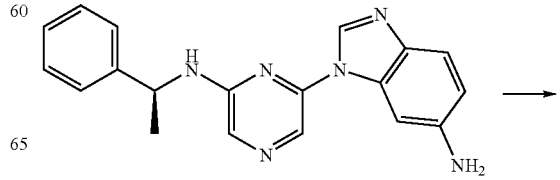

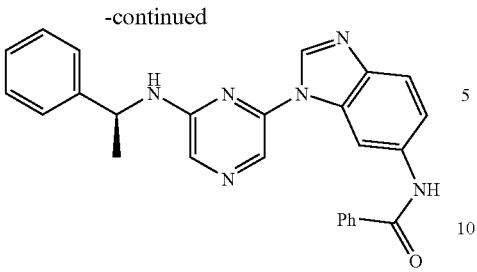

In a procedure analogous to example 32, reaction of 1-(6-{[(1S)-1-phenylethyl]amino}pyrazin-2-yl)-1H-benzimidazol-6-amine (50 mg, 0.15 mmol) and benzoyl chloride (21 mg, 0.15 mmol) furnished the product (50 mg, 76%) after chromatography.

$^1$H-n.m.r. (CDCl$_3$) δ1.64 (d, 3H, J=6.6 Hz, CH$_3$), 5.11 (m, 1H, CH), 5.31 (d, 1H, J=6.6 Hz, NH), 7.16-7.58 (m, 10H, ArH), 7.78 (d, 1H, J=8.4 Hz, benzimid-H), 7.83 (s, 1H, pyraz-H), 8.35 (s, 1H, pyraz-H), 8.51 (s, 1H, benzimid-H).

m/z (ES) 435 (M$^+$+H).

EXAMPLE 36

N-[1-(6-{[(1S)-1-phenylethyl]amino}pyrazin-2-yl)-1H-benzimidazol-5-yl]isonicotinamide

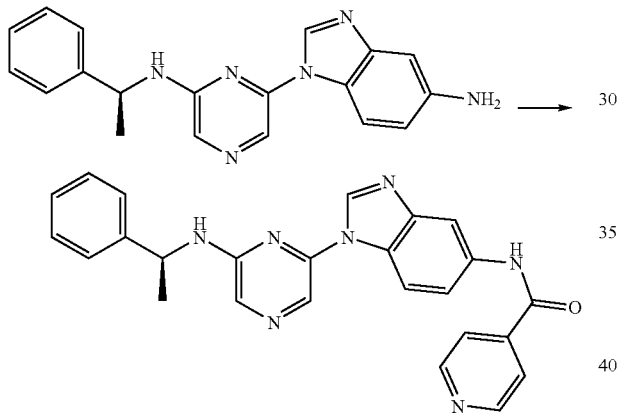

In a procedure analogous to example 32, reaction of 1-(6-{[(1S)-1-phenylethyl]amino}pyrazin-2-yl)-1H-benzimidazol-5-amine (33 mg, 0.10 mmol) and isonicotinoyl chloride hydrochloride (20 mg, 0.11 mmol) furnished the product (10 mg, 23%) after chromatography.

$^1$H-n.m.r. (CDCl$_3$) δ1.56 (d, 3H, J=6.9 Hz, CH$_3$), 4.98 (m, 1H, CH), 6.21 (d, 1H, J=6.0 Hz, NH), 7.11-7.37 (m, 5H, ArH), 7.59 (d, 1H, J=9.0 Hz, benzimid-H), 7.65 (d, 1H, J=8.7 Hz, benzimid-H), 7.81 (d, 2H, J=5.7 Hz, pyrid-H), 7.87 (s, 1H, pyraz-H), 8.01 (s, 1H, pyraz-H), 8.10 (s, 1H, benzimid-H), 8.32 (s, 1H, benzimid-H), 8.72 (d, 2H, J=5.7 Hz, pyrid-H), 9.58 (s, 1H, CONH).

m/z (ES) 436 (M$^+$+H).

EXAMPLE 37

N-[1-(6-{[(1S)-1-phenylethyl]amino}pyrazin-2-yl)-1H-benzimidazol-6-yl]isonicotinamide

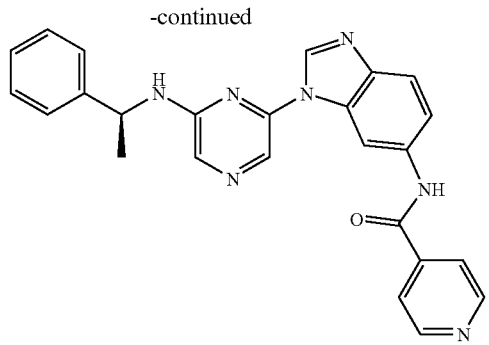

In a procedure analogous to example 32, reaction of 1-(6-{[(1S)-1-phenylethyl]amino}pyrazin-2-yl)-1H-benzimidazol-6-amine (33 mg, 0.10 mmol) and isonicotinoyl chloride hydrochloride (20 mg, 0.11 mmol) furnished the product (10 mg, 23%) after chromatography.

$^1$H-n.m.r. (CDCl$_3$) δ1.63 (d, 3H, J=6.9 Hz, CH$_3$), 5.11 (m, 1H, CH), 5.40 (d, 1H, J=6.3 Hz, NH), 7.18-7.42 (m, 6H, ArH, CONH), 7.73-7.79 (m, 3H, benzimid-H), 7.83 (s, 1H, pyraz-H), 8.10 (s, 1H, pyraz-H), 8.36 (br s, 2H, pyrid-H), 8.48 (s, 1H, benzimid-H), 8.79 (d, 2H, J=5.7 Hz, pyrid-H).

m/z (ES) 436 (M$^+$+H).

EXAMPLE 38

N-[1-(6-{[(1S)-1-phenylethyl]amino}pyrazin-2-yl)-1H-benzimidazol-5yl]nicotinamide

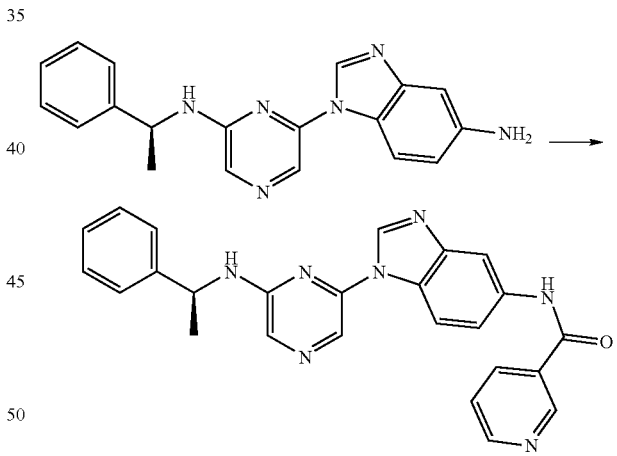

In a procedure analogous to example 32, reaction of 1-(6-{[(1S)-1-phenylethyl]amino}pyrazin-2-yl)-1H-benzimidazol-5-amine (33 mg, 0.10 mmol) and nicotinoyl chloride hydrochloride (20 mg, 0.11 mmol) furnished the product (17 mg, 39%) after chromatography.

$^1$H-n.m.r. (CDCl$_3$) δ1.48 (d, 3H, J=6.9 Hz, CH$_3$), 4.91 (m, 1H, CH), 6.59 (d, 1H, J=5.7 Hz, NH), 7.11-7.32 (m, 6H, ArH, pyrid-H), 7.58 (d, 1H, J=9.0 Hz, benzimid-H), 7.83 (s, 1H, benzimid-H), 7.91 (s, 1H, pyraz-H), 8.07 (s, 1H, benzimid-H), 8.20 (d, 1H, J=8.1 Hz, pyrid-H), 8.24 (s, 1H, pyraz-H), 8.61 (d, 1H, J=4.6 Hz, pyrid-H), 9.12 (s, 1H, pyrid-H), 9.80 (s, 1H, CONH).

m/z (ES) 436 (M$^+$+H).

EXAMPLE 39

N-[1-(6-{[(1S)-1-phenylethyl]amino}pyrazin-2-yl)-1H-benzimidazol-6-yl]nicotinamide

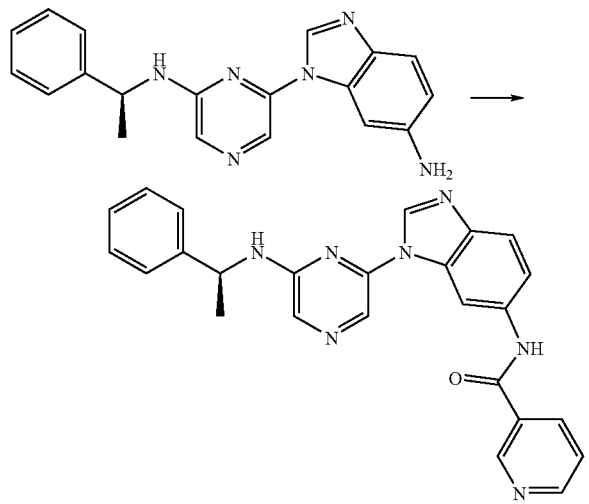

In a procedure analogous to example 32, reaction of 1-(6-{[(1S)-1-phenylethyl]amino}pyrazin-2-yl)-1H-benzimidazol-6-amine (33 mg, 0.10 mmol) and isonicotinoyl chloride hydrochloride (20 mg, 0.11 mmol) furnished the product (27 mg, 62%) after chromatography.

$^1$H-n.m.r. (CDCl$_3$) δ1.62 (d, 3H, J=6.6 Hz, CH$_3$), 5.12 (m, 1H, CH), 5.41 (d, 1H, J=6.0 Hz, NH), 7.17-7.21 (m, 1H, Ar—H), 7.26-7.29 (m, 1H, Ar—H), 7.39-7.45 (m, 4H, ArH, pyrid-H), 7.76 (d, 1H, J=8.7 Hz, benzimid-H), 7.82 (s, 1H, pyraz-H), 8.11 (s, 1H, pyraz-H), 8.21 (d, 1H, J=8.1 Hz, pyrid-H), 8.33 (s, 1H, CONH). 8.35 (s, 1H, Ar—H), 8.47 (3, 1H, pyrid-H), 8.76 (1H, d, J=4.5 Hz, pyrid-H), 9.13 (s, 1H, pyrid.-H).

m/z (E) 436 (M$^+$+H).

EXAMPLE 40

N-[1-(6-{[(1S)-1-phenylethyl]amino}pyrazin-2-yl)-1H-benzimidazol-5-yl]pyrazine-2-carboxamide

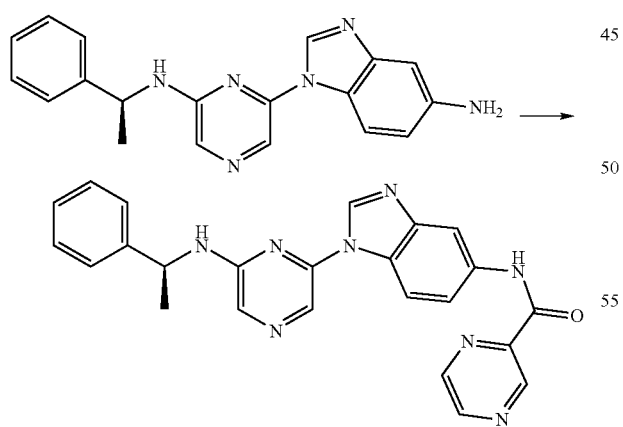

In a procedure analogous to example 32, reaction of 1-(6-{[(1S)-1-phenylethyl]amino}pyrazin-2-yl)-1H-benzimidazol-5-amine (33 mg, 0.10 mmol) and pyrazine-2-carbonyl chloride (0.11 mmol) (prepared by reacting pyrazine-2-carboxylic acid with oxalyl chloride in diclorometane at room temperature) furnished the product (24 mg 55%) after chromatography.

$^1$H-n.m.r. (CDCl$_3$) δ1.65 (d, 3H, J=6.9 Hz, CH$_3$), 5.04 (m, 1H, CH), 5.35 (d, 1H, J=6.0 Hz, NH), 7.28-7.41 (m, 5H, Ar—H, pyrid-H), 7.71 (s, 1H, pyraz-H), 7.87 (s, 1H, pyraz-H), 8.12 (s, 1H, pyraz-H), 8.21 (s, 1H, benzimid-H), 8.40 (s, 1H, pyraz-H), 8.61-8.62 (m, 1H, benzimid-H), 8.81 (d, 1H, J=2.4 Hz, benzimid-H), 9.55 (d, 1H, J=1.2 Hz, benzimid-H), 9.78 (s, 1H, CONH).

m/z (ES) 437 (M$^+$+H).

EXAMPLE 41

N-[1-(6-{[(1S)-1-phenylethyl]amino}pyrazin-2-yl)-1H-benzimidazol-6-yl]pyrazine-2-carboxamide

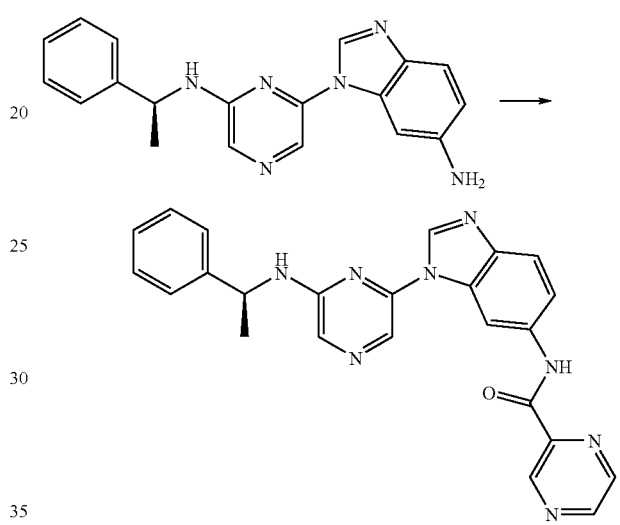

In a procedure analogous to example 32, reaction of 1-(6-{[(1S)-1-phenylethyl]amino}pyrazin-2-yl)-1H-benzimidazol-6-amine (33 mg, 0.10 mmol) and isonicotinoyl chloride hydrochloride (0.11 mmol) (prepared by reacting pyrazine-2-carboxylic acid with oxalyl chloride in diclorometane at room temperature) furnished the product (28 mg, 64%) after chromatography.

$^1$H-n.m.r. (CDCl$_3$) δ1.67 (d, 3H, J=6.9 Hz, CH$_3$), 5.18 (m, 1H, CH), 5.39 (d, 1H, J=6.3 Hz, NH), 7.23-7.46 (m, 6H, Ar—H, pyrid-H), 7.82 (d, 1H, J=9.0 Hz, benzimid-H), 7.84 (s, 1H, pyraz-H), 8.18 (s, 1H, pyraz-H), 8.39 (s, 1H, pyraz-H), 8.61-8.62 (m, 1H, pyraz-H), 8.81-8.84 (m, 2H, —Ar—H), 9.52 (d, 1H, J=1.2 Hz, benzimid-H), 9.81 (s, 1H, CONH).

m/z (ES) 437 (M$^+$+H).

EXAMPLE 42

2-Methoxy-N-[1-(6-{[(1S)-1-phenylethyl]amino}pyrazin-2-yl)-1H-benzimidazol-5-yl]acetamide

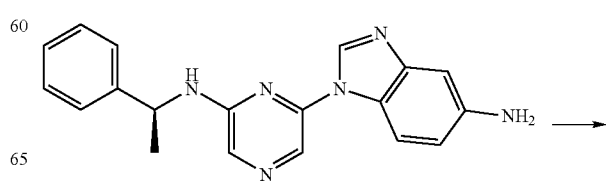

-continued

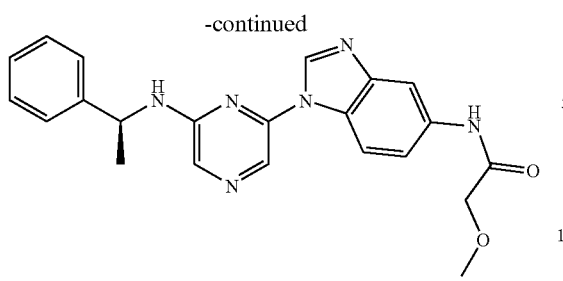

In a procedure analogous to example 32, reaction of 1-(6-{[(1S)-1-phenylethyl]amino}pyrazin-2-yl)-1H-benzimidazol-5-amine (33 mg, 0.10 mmol) and methoxyacetyl chloride (12 mg, 0.11 mmol) furnished the product (20 mg, 50%) after chromatography.

$^1$H-n.m.r. (CDCl$_3$) δ1.64 (d, 3H, J=6.9 Hz, CH$_3$), 3.55 (s, 3H, OCH$_3$), 4.07 (s, 2H, CH$_2$), 5.02 (m, 1H, CH), 5.27 (d, 1H, J=6.3 Hz, NH), 7.30-7.40 (m, 5H, Ar—H), 7.54 (dd, 1H, J=8.7, 1.5 Hz, benzimid-H), 7.66 (d, 1H, J=8.7 Hz, benzimid-H), 7.85 (s, 1H, pyraz-H), 8.01 (s, 1H, benzimid-H), 8.11 (s, 1H, pyraz-H), 8.35 (s, 1H, CONH), 8.38 (s, 1H, benzimid-H).

m/z (ES) 403 (M$^+$+H).

EXAMPLE 43

2-Methoxy-N-[1-(6-{[(1S)-1-phenylethyl]amino}pyrazin-2-yl)-1H-benzimidazol-6-yl]acetamide

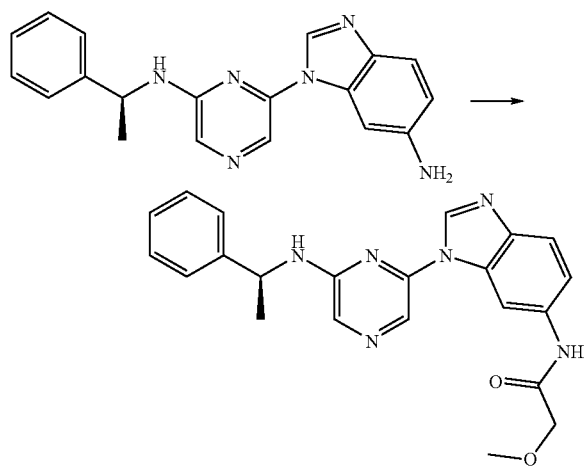

In a procedure analogous to example 32, reaction of 1-(6-{[91S)-1-phenylethyl]amino}pyrazin-2-yl)-1H-benzimidazol-6-amine (33 mg, 0.10 mmol) and methoxyacetyl chloride (20 mg, 0.11 mmol) furnished the product (10 mg, 25%) after chromatography.

$^1$H-n.m.r. (CDCl$_3$) δ1.64 (d, 3H, J=6.9 Hz, CH$_3$), 3.54 (s, 3H, OCH$_3$), 4.06 (s, 2H, CH$_2$), 5.08 (m, 1H, CH), 5.36 (d, 1H, 6.3 Hz, NH), 7.24-7.42 (m, 6H, Ar—H), 7.76 (d, 1H, J=8.7 Hz, benzimid-H), 7.81 (s, 1H, pyraz-H), 8.14 (s, 1H, pyraz-H), 8.35 (s, 1H, benzimid-H), 8.39 (s, 1H, CONH), 8.52 (d, 1H, 1.5 Hz, benzimid-H).

m/z (ES) 403 (M$^+$+H).

EXAMPLE 44

N-[1-(6-{[(1S)-1-phenylethyl]amino}pyrazin-2-yl)-1H-benzimidazol-6-yl]-2,2-dimethylpropanamide

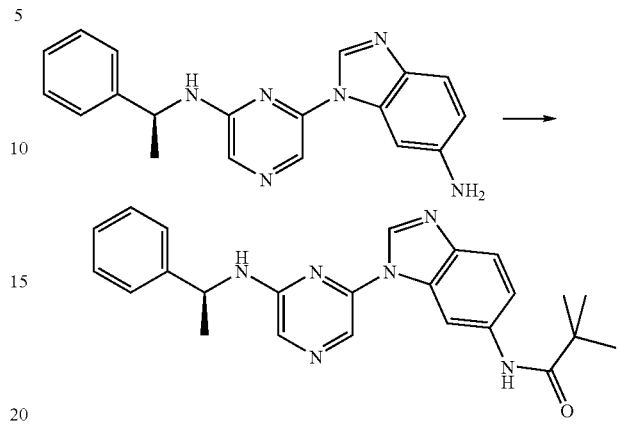

To a stirred solution of 2-(benzylamino)-6-(5-amino-benzimidazo-1-yl)-pyrazine (33 mg, 0.1 mmol) in anhydrous THF (2 mL) under N$_2$ was added triethylamine (38 1, 0.3 mmol). The solution was cooled at 0° C. and to this was added pivalic acid (12 mg, 0.11 mmol) and EDC (23 mg, 0.12 mmol) and the resulting mixture then stirred at RT. After 64 h the solution was diluted with H$_2$O and the mixture extracted with CHCl$_3$ (2×15 mL). The combined organic layers were washed with 10% aqueous Na$_2$CO$_3$, dried (Na$_2$SO$_4$) and the solvent removed in vacuo. The residue was purified by column chromatography using dichloromethane-methanol (100:6) as eluant to separate the pur product (15 mg).

$^1$H-n.m.r. (CDCl$_3$) δ1.35 (s, 9H, 3CH$_3$), 1.65 (d, 3H, J=6:6 Hz, CH$_3$), 5.14 (m, 1H, CH), 5.24 (d, 1H, J=5.7 Hz, NH), 7.13 (d, 1H, J=8.7 Hz, Ar—H), 7.29-7.47 (m, 5H, ArH), 7.75 (d, 1H, J=8.7 Hz, benzimid-H), 7.81 (s, 1H, pyraz-H), 8.17 (s, 1H, pyraz-H), 8.35 (s, 1H, benzimid-H), 8.69 (s, 1H, CONH).

m/z (ES) 415 (M$^+$+H).

EXAMPLE 45

N-[1-(6-{[(1S)-1-phenylethyl]amino}pyrazin-2-yl)-1H-benzimidazol-5-yl]-2,2-dimethylpropanamide

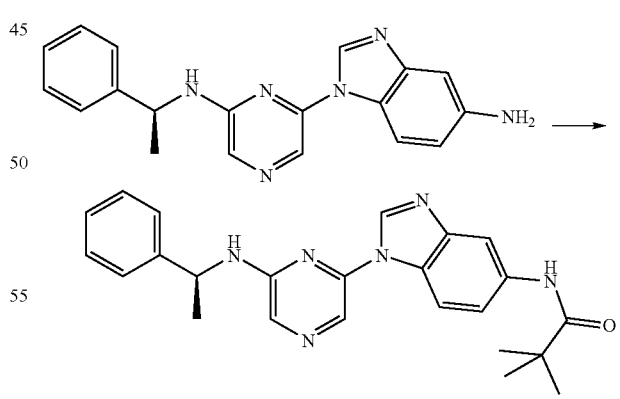

In a procedure analogous to example 44, reaction of 1-(6-{[(1S)-1-phenylethyl]amino}pyrazin-2-yl)-1H-benzimidazol-5-amine (33 mg, 0.10 mmol) and pivalic acid (12 mg, 0.11 mmol) furnished the product (12 mg, 29%) after chromatography.

$^1$H-n.m.r. (CDCl$_3$) δ1-35 (s, 9H, CH$_3$), 1.66 (d, 3H, J=6.9 Hz, CH$_3$), 5.14 (m, 1H, CH), 5.24 (d, 1H, J=6.3 Hz, NH), 7.13 (d, 1H, J=8.7 Hz, Ar—H), 7.29-7.47 (m, 6H, ArH), 7.75 (d,

1H, J=8.7 Hz, benzimid-H), 7.81 (s, 1H, pyraz-H), 8.17 (s, 1H, pyraz-H), 8.35 (s, 1H, benzimid-H), 8.69 (s, 1H, CONH).

m/z (ES) 415 (M$^+$+H).

EXAMPLE 46

6-{5-[(4-Methylpiperazin-1-yl)methyl]-1H-benzimidazol-1-yl}-N-[(1S)-1-phenylethyl]pyrazin-2-amine

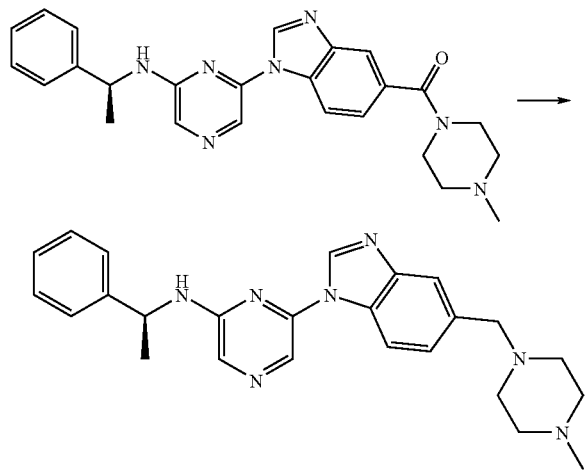

A solution of 6-{5-[(4-methylpiperazin-1-yl)carbonyl]-1H-benzmidazol-1-yl}-N-[(1S)-1-phenylethyl]pyrazin-2-amine (22 mg, 0.05 mmol) in dry THF (1 mL) was added to a suspension of LiAlH$_4$ (4 mg, 0.1 mmol) in THF (1 mL) and the mixture heated at reflux for 4 h. Upon cooling to RT, the solution was treated consecutively with H$_2$O (1 mL), aqueous NaOH (1 mL, 2M) and H$_2$O (5 mL). The resulting mixture was extracted with CHCl$_3$ (2×10 mL) and the combined organic layers dried (Na$_2$SO$_4$). The solvent was removed under reduced pressure and the product purified by flash chromatography using CH$_2$Cl$_2$—MeOH (10:1→1:1) as eluant to afford the product as a yellow solid (11 mg, 52%).

$^1$H-n.m.r. (CDCl$_3$) δ1.65 (d, 3H, J=6.9 Hz, CH$_3$), 2.58 (s, 3H, NCH$_3$), 2.81 (br s, 4H, CH$_2$), 2.90 (br s, 4H, CH$_2$), 3.74 (s, 2H, NCH$_2$), 5.03 (m, 1H, CH), 5.33 (d, 1H, J=6.0 Hz, NH), 7.25-7.42 (m, 6H, Ar—H), 7.67 (d, 1H, J=8.4 Hz, benzimid-H), 7.77 (s, 1H, benzimid-H), 7.87 (s, 1H, pyraz-H), 8.12 (s, 1H, pyraz-H), 8.39 (s, 1H, benzimid-H).

m/z (ES) 428 (M$^+$+H).

EXAMPLE 47

1-[6-{[(1S)-1-Phethylethyl]amino}pyrazin-2-yl]-N-(pyridin-3-ylmethyl)-1H-benzimidazol-5-amine

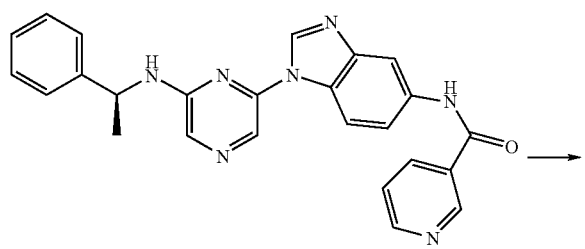

-continued

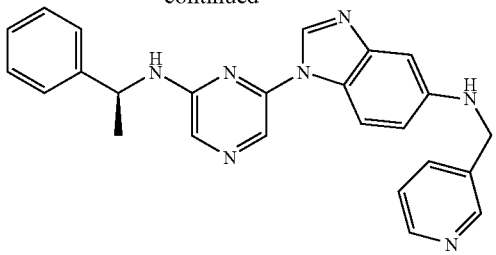

In a procedure analogous to example 46, reaction of N-[1-(6-{[(1S)-1-phenylethyl]amino}pyrazin-2-yl)-1H-benzimidazol-5-yl]nicotinamide (33 mg, 0.10 mmol) with LiAlH$_4$ (5.7 mg, 0.15 mmol) furnished the product (10 mg, 24%) after chromatography.

$^1$H-n.m.r. (CDCl$_3$) δ 1.64 (d, J=6.9 Hz, 3H, CH$_3$), 4.42(s, 2H, CH$_2$), 5.01(m, 1H, CH), 5.20(d, J=6.0 Hz, 1H, NH), 6.66 (dd, J=8.7, 2.1 Hz, 1H, H-7'), 7.01 (d, J=2.1 Hz, 1H, H-4'), 7.25-7.45 (m, 6H, ArH), 7.51 (d, J=8.7 Hz, 1H, H-6'), 7.74 (d, J=7.8 Hz, pyridine-H), 7.80 (s, 1H, pyraz-H), 8.09 (s, 1H, pyraz-H), 8.30 (s, 1H, H-2'), 8.53 (d, J=3.6 Hz, 1H, pyridine-H), 8.68(s, 1H, pyridine-H).

m/z (ES) 422 (M$^+$+H).

EXAMPLE 48

N-[(1S)-1-(4-Bromophenyl)ethyl]-6-chloropyrazin-2-amine

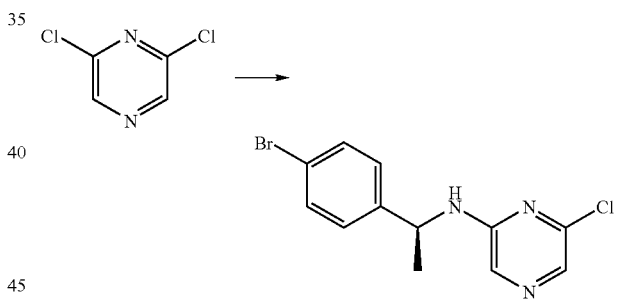

In a procedure analogous to example 1, reaction of 4-bromo-α-S-methyl-benzylamine (877 mg, 4.4 mmol) and 2,6-dichloropyrazine (597 mg, 4.0 mmol) furnished the product (835 mg, 67%).

$^1$H-n.m.r. (CDCl$_3$) δ 1.56 (d, J=6.9 Hz, 3H, CH$_3$), 4.86 (m, 1H, CH), 5.0 (d, 1H, NH), 7.24 (AA'XX', 2H, ArH) 7.60 (s, 1H, pyraz-H), 7.81 (s, 1H, pyraz-H).

EXAMPLE 49

6-Chloro-N-[(1S)-1-(4-methoxyphenyl)ethyl]pyrazin-2-amine

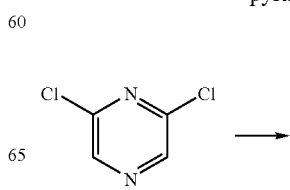

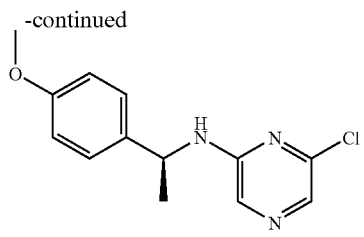

In a procedure analogous to examples 1, reaction of 4-methoxy-α-S-methyl-benzylamine (700 mg, 4.6 mmol) and 2,6-dichloropyrazine (626 mg, 4.2 mmol) furnished the product (873 mg, 79%).

¹H-n.m.r. (CDCl₃) δ1.56 (d, J=6.9 Hz, 3H, CH₃), 3.80 (s, 3H, OCH₃), 4.84 (m, 1H, CH), 5.01 (d, 1H, NH), 6.88 (AA'XX', 2H, Ar—H), 7.28 (AA'XX', 2H, Ar—H), 7.621 (s, 1H, pyraz-H), 7.79 (s, 1H, pyraz-H).

EXAMPLE 50

6-(1H-Benzimidazol-1-yl)-N-[(1S)-1-(4-bromophenyl)ethyl]pyrazin-2-amine

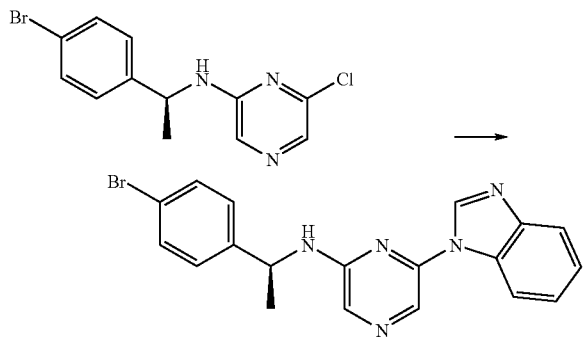

In a procedure analogous to example 25, reaction of N-[(1S)-1-(4-bromophenyl)ethyl]-6-chloropyrazin-2-amine (125 mg, 0.40 mmol) and benzimidazole (52 mg, 0.44 mmol) furnished the product (66 mg, 42%).

¹H-n.m.r. (CDCl₃) δ1.63 (d, 3H, J=6.9 Hz, CH₃), 4.99 (m, 1H, CH), 5.19 (d, 1H, J=5.1 Hz, NH), 7.26-7.37 (m, 3H, Ar—H), 7.51 (AA'XX', 2H, Ar—H), 7.65 (d, 1H, J=8.1 Hz, benzimid-H), 7.83-7.86 (m, 2H, benzimid-H+pyraz-H), 8.17 (s, 1H, pyraz-H), 8.39 (s, 1H, benzimid-H).

m/z (ES) 396, 394 (M⁺+H)

EXAMPLE 51

6-(1H-Benzimidazol-1-yl)-N-[(1S)-1-(4-methoxyphenyl)ethyl]pyrazin-2-amine

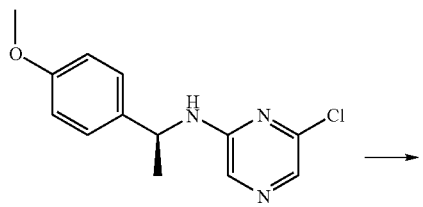

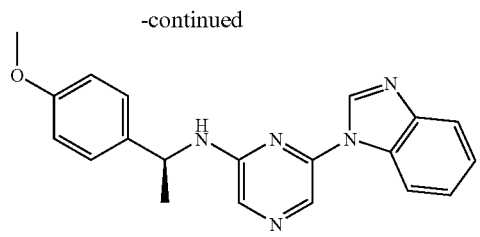

In a procedure analogous to example 25, reaction of 6-chloro-N-[(1S)—1-(4-methoxyphenyl)ethyl]pyrazin-2-amine (105 mg, 0.40 mmol) and benzimidazole (52 mg, 0.44 mmol) furnished the product (57 mg, 41%).

¹H-n.m.r. (CDCl₃) δ1.62 (d, 3H, J=6.8 Hz, CH₃), 3.80 (s, 3H, CH₃), 4.99 (m, 1H, CH), 5.31 (br d, 1H, J=6.2 Hz, NH), 6.91 (AA'XX', 2H, Ar—H), 7.28-7.36 (m, 4H, Ar—H), 7.77 (d, 1H, J=2.0 Hz, Ar—H), 7.78 (s, 2H, benzimid-H+pyraz-H), 8.13 (s, 1H, pyraz-H), 8.44 (s, 1H, benzimid-H).

m/z (ES) 346 (M⁺+H)

EXAMPLE 52

2-(S-α-Methylbenzylamino)-6-(5-(N-methylpiperazin-4-yl-methyl)-benzimidazo-1-yl)-pyrazine

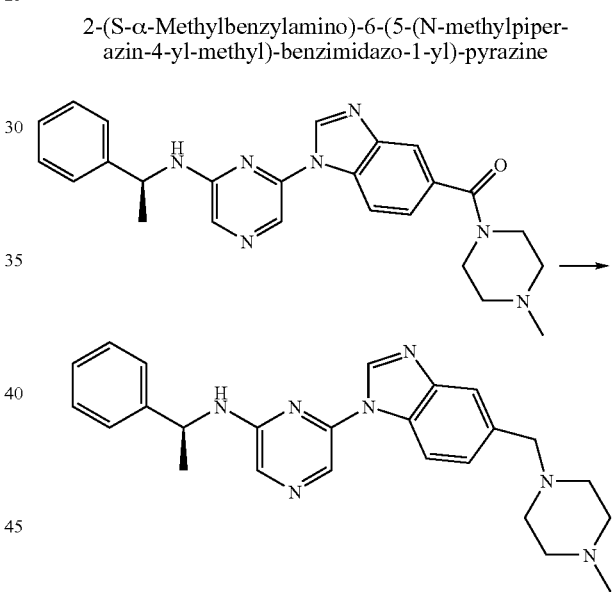

A solution of 3-[6-(S-α-methylbenzylamino)-pyrazin-2-yl]-3H-benzoimidazole-5-carboxylic acid N-methylpiperazinylamide (22 mg, 0.05 mmol) in dry THF (1 mL) was added to a suspension of LiAlH₄ (4 mg, 0.1 mmol) in THF (1 mL) and the mixture heated at reflux for 4 h. Upon cooling to RT, the solution was treated consecutively with H₂O (1 mL), aqueous NaOH (1 mL, 2M) and H₂O (5 mL). The resulting mixture was extracted with CHCl₃ (2×10 mL) and the combined organic layers dried (Na₂SO₄). The solvent was removed under reduced pressure and the product purified by flash chromatography using CH₂Cl₂-MeOH (10:1→1:1) as eluant to afford the product as a yellow solid (11 mg, 52%).

¹H-n.m.r. (CDCl₃) δ1.65 (d, 3H, J=6.9 Hz, CH₃), 2.58 (s, 3H, NCH₃), 2.81 (br s, 4H, CH₂), 2.90 (br s, 4H, CH₂), 3.74 (s, 2H, NCH₂), 5.03 (m, 1H, CH), 5.33 (d, 1H, J=6.0 Hz, NH), 7.25-7.42 (m, 6H, Ar—H), 7.67 (d, 1H, J=8.4 Hz, benzimid-H), 7.77 (s, 1H, benzimid-H), 7.87 (s, 1H, pyraz-H), 8.12 (s, 1H, pyraz-H), 8.39 (s, 1H, benzimid-H).

m/z (ES) 428 (M⁺+H).

EXAMPLE 53

1-{4-[2-(Diethylamino)ethoxy]phenyl}ethanone

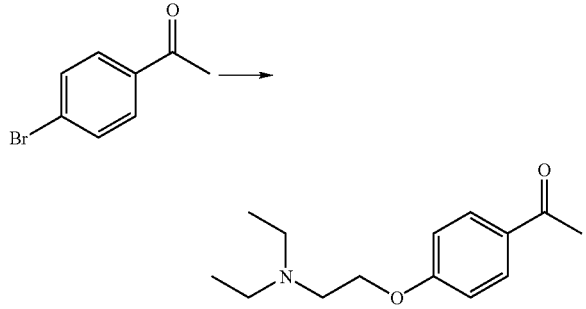

A mixture of 4-bromoacetophenone (5 g, 25 mmol), the diethylaminoethanol (3.5 g, 38 mmol), $K_2CO_3$ (2g), copper powder (0.5 g) and copper(I) iodide (2.5 g) in DMSO (30 ml) was heated at 120° C. until TLC showed consumption of the starting material. After cooling to RT, the mixture was poured onto aqueous $NH_3$ (28%, 100 ml), extracted with $CH_2Cl_2$ (3×100 ml). The combined organic extracts were dried ($Na_2SO_4$), filtered and the $CH_2Cl_2$ distilled in vacuo. The crude product was purified by column chromatography on silica gel, eluting with EtOAc-MeOH (95:5) to furnish the pure compound (4.85 g, 82%).

$^1$H-n.m.r. (CDCl$_3$) δ0.98 (t, J=7.2 Hz, 6H, NCH$_2$CH$_3$), 2.43 (s, 3H, Ar—C—CH$_3$), 2.57-2.50 (m, 4H, NCH$_2$CH$_3$), 2.78 (t, J=6.3 Hz, 2H, ArOCH$_2$CH$_2$N), 4.00 (t, J=6.3 Hz, 2H, ArO-CH$_2$), 6.85 (d, J=9 Hz, 2H, ArH), 7.83 (d, J=9 Hz, 2H, ArH).

EXAMPLE 54

1-[4-(4-Methylpiperazin-1-yl)phenyl]ethanone

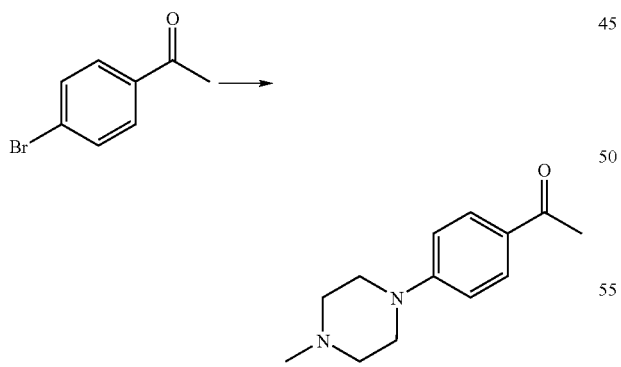

In a procedure identical to Example 53, 4-bromoacetophenone was reacted with N-methylpiperazine in the presence of potassium carbonate, copper and copper iodide to furnish the desired product in 82% yield.

$^1$H-n.m.r. (CDCl$_3$) δ 2.35 (s, 3H, Ar—C—CH$_3$), 2.52 (s, 3H, N—CH$_3$), 2.55 (t, J=5.1 Hz, 4H, CH$_2$—N—CH$_3$), 3.37 (dd, J=5.1, 5.1 Hz, 4H, ArNCH$_2$), 6.89 (AA'XX', 2H, ArH), 7.89 (AA'XX', 2H, ArH).

EXAMPLE 55

1-Pyridin-3-ylethanone oxime

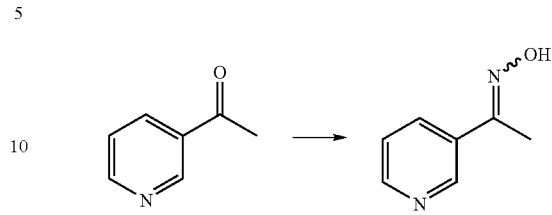

To a solution of hydroxylamine hydrochloride (3.44 g) in water (20 ml) was added NaOH (20%, 30 ml). The ketone (5 g, 41 mmol) was added at once and the resulting mixture was stirred at RT until TLC showed no ketone remained. The solvents were distilled off in vacuo and the residue extracted with $CH_2Cl_2$ (3×100 ml) and dried ($Na_2SO_4$). After filtration and removal of the solvent, the crude ketoxime was recrystallised from $CH_2Cl_2$/n-hexane.

$^1$H-n.m.r. (CDCl$_3$) δ2.31 (s, 3H, CH$_3$), 7.33 (dd, J=4.8, 4.8 Hz, 1H, ArH), 7.97 (ddd, J=8.1, 1.8, 1.8 Hz, 1H, ArH), 8.61 (dd, J=5.1, 1.8 Hz, 1H, ArH), 8.96 (d, J=1.8 Hz, 1H, ArH), 10.62 (s, 1H, OH).

EXAMPLE 56

1-(3-Chlorophenyl)ethanone oxime

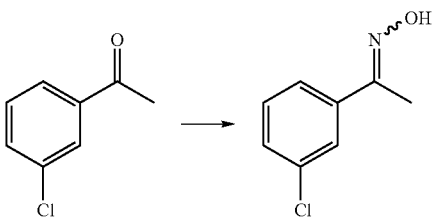

A mixture of the ketone (2.0 g, 13 mmol), hydroxylamine hydrochloride (0.98 g, 14 mmol), NaOH (10%, 4 ml), water (6.2 ml) and EtOH (25 ml) was heated under reflux for 2 hours. Upon cooling in ice, the ketoxime precipitated and was collected by suction filtration. The crude product was recrystallised from CH$_2$C$_2$/n-hexane (1.88 g, 86%).

$^1$H-n.m.r. (CDCl$_3$) δ 2.28 (s, 3H, CH$_3$), 7.51 (s, 4H, ArH), 8.67 (s, 1H, OH).

EXAMPLE 57

1-(3-Chlorophenyl)ethanamine

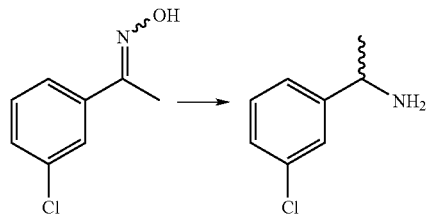

A mixture of the ketoxime (1 g, 6 mmol) and LiAlH$_4$ (0.27 g) in anhydrous THF (100 ml) was heated at reflux under dry N₂ overnight. The reaction mixture was cooled in ice-water and carefully quenched with H₂O (60 mL). The mixture was allowed to stir at RT for half an hour, after which time it was filtered through Celite®. The inorganic salts were washed with EtOAc (3×100 ml). The filtrate was concentrated under reduced pressure, diluted with 2M HCl (50 ml) and the aqueous phase washed with Et₂O (2×70 ml). The aqueous phase was basified with 40% aqueous NaOH and the product extracted with Et₂O (3×50 ml). The combined organic layers were washed with brine (50 ml) and dried (MgSO₄). The solvents were removed in vacuo to afford the pure amine (0.65 g, 71%).

¹H-n.m.r. (CDCl₃) δ1.38 (d, J=6.6 Hz, 3H, CH—CH₃), 1.63 (br s, 2H, NH₂), 4.13-4.06 (m, 1H, CH—CH₃), 7.23-7.18 (m, 3H, ArH), 7.35 (s, 1H, ArH).

EXAMPLE 58

1-Pyridin-3-ylethanamine

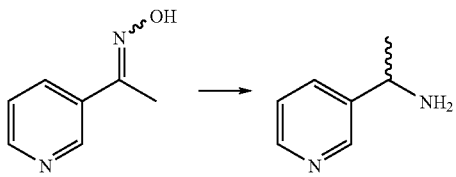

To a mixture of the ketoxime (4.85 g, 36 mmol) and Zn powder (12 g) at 0° C. was slowly added, with vigorous stirring, concentrated HCl (50 ml). When the initial vigorous reaction had subsided, the mixture was heated under reflux until TLC showed all the ketoxime had been consumed. After cooling to RT, the strongly acidic mixture was extracted with CH₂Cl₂ (2×75 ml). The reaction mixture was then made strongly basic with 50% KOH solution. After removal of the solvent, the residue was extracted with boiling MeOH (4×100 ml). The MeOH was distilled off to leave the crude amine which was used in the ensuing reactions without further purification.

¹H-n.m.r. (CDCl₃) δ1.07 (d, J=6.6 Hz, 3H, CH₃), 1.37 (br s, 2H, NH₂), 3.84 (q, J=4.6 Hz, 1H, CH—CH₃), 6.93 (dd, J=7.8, 4.8 Hz, 1H, ArH), 7.38 (ddd, J=7.8, 2.1, 1.5 Hz, 1H, ArH), 8.15 (dd, J=4.8, 1.5 Hz, 1H, ArH), 8.27 (d, J=2.1 Hz, 1H, ArH).

EXAMPLE 59

6-Chloro-N-[(1S)-1-(4-pyridin-3-ylphenyl)ethyl] pyrazin-2-amine

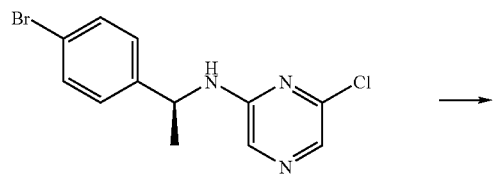

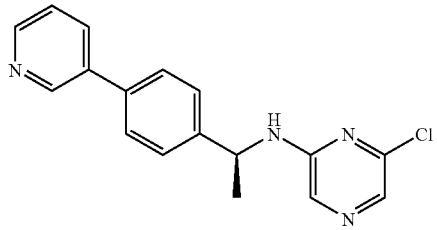

Under a nitrogen atmosphere a mixture of N-[(1S)-1-(4-bromophenyl)ethyl]-6-chloropyrazin-2-amine (0.117 g, 0.37 mmol), pyridine-3-boronic acid 1,3-propanediol cyclic ester (67 mg, 0.41 mmol), tetrakis(triphenylphosphine)palladium (0) (65 mg, 0.06 mmol) and toluene (4 mL) was treated with 2M aqueous sodium carbonate solution (0.2 mL). The resulting mixture was stirred vigorously whilst being heated under reflux for 24 hours. Upon cooling, the solution was diluted with methanol and dichloromethane and the mixture dried (MgSO₄) and filtered. Removal of solvent in vacuo then yielded the crude product which was purified by column chromatography using dichloromethane-diethyl ether (90:10) then dichloromethane-methanol (99:1) as eluent (50 mg).

¹H-n.m.r. (CDCl₃) δ1.61 (d, 3H, J=6.9 Hz, CH₃), 4.97 (m, 1H, CH), 5.42 (d, 1H, J=6.3 Hz, NH), 7.33-7.37 (m, 1H, ArH), 7.42-7.56 (m, 4H, ArH), 7.66 (m, 1H, pyraz-H), 7.78 (s, 1H, pyraz-H), 7.83-7.86 (m, 1H, ArH), 8.58 (br s, 1H, pyrid-H), 8.83 (br s, 1H, pyrid-H).

m/z (ES) 313, 311 (M++H).

EXAMPLE 60

N-[1-(6-{[(1S)-1-Phenylethyl]amino}pyrazin-2-yl)-1H-benzimidazol-5-yl)]methanesulfonamide

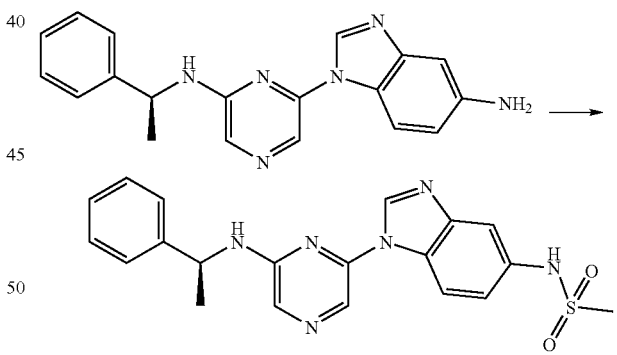

To a stirred solution of 2-(S-α-methylbenzylamino)-6-(5-amino-benzimidazo-1-yl)-pyrazine (33 mg, 0.1 mmol) in anhydrous THF (2 mL) under N₂ was added triethylamine (40 mg, 0.4 mmol). The solution was cooled at 0° C. and to this was added methanesulphonyl chloride (25 mg, 0.2 mmol) and the resulting mixture then stirred at RT. After 16 h the solution was poured into water (30 mL) and the product extracted into chloroform (2×15 mL). The combined organic layers were was washed with 10% Na₂CO₃, dried (Na₂SO₄) and the solvent removed under reduced pressure to furnish the crude product as a pale yellow solid. Column chromatography, using dichloromethane-methanol (100:6) as eluant, separated the product from the most polar fractions as a pale yellow solid (16 mg).

¹H-n.m.r. (CDCl₃) δ1.65 (d, 3H, J=6.9 Hz, CH₃), 3.00 (s, 3H, CH₃), 5.02 (m, 1H, CH), 5.27 (d, H, J=6.0 Hz, NH), 7.21-7.40 (m, 6H, ArH), 7.64 (d, 1H, J=8.7 Hz, benzimid-H), 7.69 (d, 1H, J=1.9 Hz, benzimid-H), 7.88 (s, 1H, pyraz-H), 8.10 (s, 1-H, pyraz-H), 8.41 (s, 1H, benzimid-H).

m/z (ES) 409 (M++H).

EXAMPLE 61

N-[(1S)-1-Phenylethyl]-6-(5-pyridin-4-yl-1H-benzimidazol-1-yl)pyrazin-2-amine and N-[(1S)-1-Phenylethyl]-6-(6-pyridin-4-yl-1H-benzimidazol-1-yl)pyrazin-2-amine

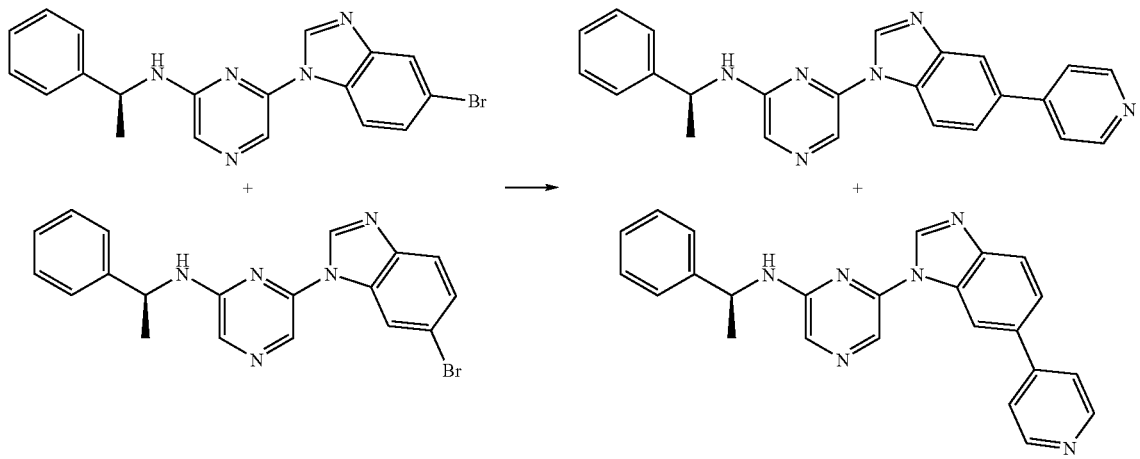

To a stirred solution of a 1:1 mixture of 6-(5-bromo-1H-benzimidazol-1-yl)-N-[(1S)-1-phenylethyl]pyrazin-2-amine and 6-(6-bromo-1H-benzimidazol-1-yl)-N-[(1S)-1-phenylethyl]pyrazin-2-amine (16 mg, 0.4 mmol), pyridine-4-boronic acid pinacol cyclic ester (91 mg, 0.44 mmol) in toluene (5 mL) was added tetrakis(triphenyl-phosphine) palladium (46 mg, 0.04 mmol) followed by aqueous sodium carbonate (0.22 mL, 2M). The solution was then heated under reflux for 24 h. After standard work-up (see example 60) the products were obtained, as a 1:1 mixture by flash chromatography using dichloromethane-methanol (100:6) as eluant.

¹H-n.m.r. (as 1:1 mixture) (CDCl₃) δ 1.66 (d, J=6.9 Hz, 3H, CH₃), 5.07 (m, 1H, CH), 5.25 (d, J=6.0 Hz, 1H, NH), 7.29-7.42 (m, 5H, ArH), 7.52-7.64 (m, 3H), 7.78 (d, J=8.7 Hz), 7.88 and 7.90 (s, 1H, pyraz-H), 7.94 (d, 1H, J=8.4 Hz) 8.12 (s, 1H), 8.16 (s, 1H), 8.19 and 8.20 (s, 1H, pyraz-H), 8.44 and 8.45 (s, 1H, H-2'), 8.68 (d, J=3.6 Hz, 1H, pyridine-H), 8.68 and 8.71 (d, 1H, J=8.7 Hz, pyridine-H).

m/z (ES) 393 (M⁺+H).

Screening

Compound Dilution

For screening purposes, compounds were diluted in 96 well plates at a concentration of 20 μM. Plates were warmed at 37° C. for 30 minutes before assay.

JAK Tyrosine Kinase Domain Production

JAK kinase domains were produced in the following manner:

JAK1

The kinase domain of humanJAK1 was amplified from U937mRNA using the polymerase chain reaction with the following primers:

```
XHOI-J1                             (SEQ ID NO:1)
5'-CCG CTC GAG ACT GAA GTG GAC CCC ACA CAT-3'

J1-KPNI                             (SEQ ID NO:2)
5'-CGG GGT ACC TTA TTT TAA AAG TGC TTC AAA-3'
```

JAK1 PCR products were cloned into the pFastBac HTb expression vector (Gibco) via the Xho I and Kpn I sites. The JAK1 plasmid was then transformed into competent DH10Bac cells (Gibco), and the recombinant baculovirus produced prepared for transfection into Sf9 insect cells.

JAK2

The kinase domain of humanJAK2 was amplified from U937mRNA using the polymerase chain reaction with the following primers:

```
SALI-jk2                            (SEQ ID NO:3)
5'-ACG CGT CGA CGG TGC CTT TGA AGA CCG GGA T-3' jk2-NOTI                            (SEQ ID NO:4)
5'-ATA GTT TAG CGG CCG CTC AGA ATG AAG
GTC ATT T-3'
```

JAK2 PCR products were cloned into the pFastBac HTc expression vector (Gibco) via the Sal I and Not I sites. The JAK2 plasmid was then transformed into competent DH10Bac cells (Gibco), and the recombinant baculovirus produced prepared for transfection into Sf9 insect cells.

JAK3

The kinase domain of humanJAK3 was amplified from U937mRNA using the polymerase chain reaction with the following primers:

```
XHOI-J3                             (SEQ ID NO:5)
5'-CCG CTC GAG TAT GCC TGC AA GAC CCC ACG-3'

J3-KPNI                             (SEQ ID NO:6)
5'-CGG GGT ACC CTA TGA AAA GGA CAG GGA GTG-3'
```

JAK3 PCR products were cloned into the pFastBac HTb expression vector (Gibco) via the Xho I and Kpn I sites. The JAK3 plasmid was then transformed into competent DH10Bac cells (Gibco), and the recombinant baculovirus produced prepared for transfection into Sf9 insect cells.

TYK2

The kinase domain of humanTYK2 was amplified from A549 mRNA using the polymerase chain reaction with the following primers:

```
HT2EK                                       (SEQ ID NO:7)
5'-GGA GCA CTC GAG ATG GTA GCA CAC AAC CAG GTG-3'

ITY2.2R
5'-                                         (SEQ ID NO:8)
GGA GCA GGA ATT CCG GCG CTG CCG GTC AAA TCT GG-3'
```

TYK2 PCR products were cloned into pBlueBacHis2A (Invitrogen) via the EcoRI site. The recombinant TYK2 baculovirus produced was prepared for transfected into Sf9 insect cells.

Large Scale Production Of Kinase Domains

Baculovirus preparations from each of the JAK family members were infected into five litres of High Five cells (Invitrogen) grown in High Five serum free medium (Invitrogen) to a cell density of approximately $1-2 \times 10^6$ cells/ml. Cells are infected with virus at a MOI of 0.8-3.0. Cells were harvested and lysed. JAK kinase domains were purified by affinity chromatography on a Probond (Invitrogen) nickel chelate affinity column.

Assay Protocols

Kinase assays were performed either in a 96 well capture-based ELISA assay or in 384 well Optiplates (Packard) using an Alphascreen Protein Tyrosine Kinase kit. In either case using approximately 1.5 µg of affinity purified PTK domain in the presence of 50 mM HEPES, pH 7.5, 10 mM $MgCl_2$, 150 mM NaCl and 10 µM-1mM ATP. The biotinylated substrate biotin-EGPWLEEEEEAYGWMDF-$NH_2$ (SEQ ID NO:9) (final concentration 5 µM) was used as substrate. In the ELISA assay tyrosine phosphorylation was quantitated following transfer to an avidin coated ELISA plate using peroxidase-linked anti-phospho-tyrosine antibody PY20. In the Alphascreen assay, Alphascreen phosphotyrosine acceptor beads followed by streptavidin donor beads were added under subdued light. The ELISA plates were read on a BMG Fluorostar, the Alphascreen plates were read on a Packard Fusion Alpha. Inhibitors were added to the assays fifteen minutes prior to the addition of ATP. Inhibitors were added in aqueous DMSO, with DMSO concentrations never exceeding 1%.

Establishment of TEL:JAK Cell Lines

The coding region encompassing nucleotides 1-487 of TEL was amplified by PCR using the oligonucleotides 5TEL (5'-GGA GGA TCC TGA TCT CTC TCG CTG TGA GAC-3') (SEQ ID NO:10) and 3TEL (5'-AGGC GTC GAC TTC TTC TTC ATG GTT CTG-3') (SEQ ID NO: 11) and U937 mRNA as template. A BamH I site was present into the 5TEL Primer, a Sal I site was incorporated into the 3TEL primer. The regions encompassing the kinase domains of JAK2 (nucleotides 2994-3914; JAK2F 5'-ACGC GTC GAC GGT GCC TTT GAA GAC CGG GAT-3'(SEQ ID NO:12); JAK2R 5'-ATA GTT TAG CGG CCG CTC AGA ATG AAG GTC ATT T-3') (SEQ ID NO:13) and JAK3 (nucleotides 2520-3469; JAK3F 5'-GAA GTC GAC TAT GCC TGC CAA GAC CCC ACG ATC TT-3' (SEQ ID NO:14); JAK3R 5'-GGA TCT AGA CTA TGA AAA GGA CAG GGA GTG GTG TTT -3') (SEQ ID NO: 15) were generated by PCR using Taq DNA Polymerase (Gibco/BRL) and U937 mRNA as template. A Sal1 site was incorporated into the forward primer of JAK2 and JAK3, a Not I site was incorporated into the JAK2 reverse primer and a Xba I site was added to the reverse primer of JAK3.

A TEL/Jak2 fusion was generated by digestion of the TELPCR product with BamH I/Sal I, digestion of the JAK2 PCR product with Sal I/Not I followed by ligation and subcloning into the mammalian expression Vector pTRE 2 (Clontech) digested with BamH I-Not I (pTELJAK2). For JAK3 Sal I/Not I cleaved kinase domain PCR product was ligated with BamH I/Sal I cleaved TELproduct followed by ligation into BamH I/Not I cleaved pTRE2 (pTELJAK3).

The growth factor dependent myelomonocytic cell line BaF3 bearing the pTET-off plasmid (Clontech) was transfected with either pTELJAK2 or pTELJAK3 and the cells selected for factor independent growth. BaF 3 wild type cells were cultured in DMEM 10% FCS, 10% WEHI 3B conditioned medium. BaF3 TELJAK cells were cultured in DMEM 10% Tet-System Approved FBS (without WEHI 3B conditioned medium).

Cellular Assays were Performed as Follows:

Cell suspensions were prepared by harvesting cells from culture. (Cells used in this test should be in later log phase growth and high viability.) Cells were diluted in correct growth medium to 1.1× final concentration (from 50000 cell/mL to 200,000 cell/mL, depending on cell line).

Compounds to be tested were added (10 µL, 10× final concentration) to a flat bottom 96-well plate. The cellular suspension (90 µL per well) was added, and the plate incubated for 40 hr at 37° C., 5% $CO_2$. MTT (20 µL per well, 5 mg/mL in PBS) was added and the palates were returned to the incubator for a further 6 hours. Lysis buffer (100 µL per well, 10% SDS, 0.01N HCl) was added and the plate stored in the incubator overnight. The plate was then read at 590 nm.

Results

The activity of a range of compounds is shown in Table 3. Compounds that exhibited a capacity to inhibit 50% of JAK activity at a concentration of 50 µM (measured under standard conditions, see Methods), are designated as "+".

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 3
Disubstituted pyrazines possessing JAK inhibitory activity
| CHEMISTRY | Jak2 | Jak3 | abl | ack | kdr |
|---|---|---|---|---|---|
| 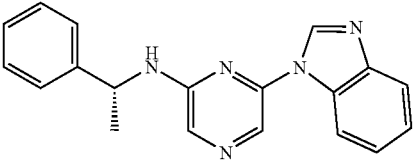<br>Chemistry 7 | + | − | + | + | + |
| 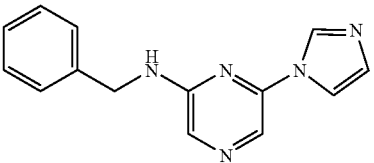<br>Chemistry 8 | − | − | + | + | − |
| 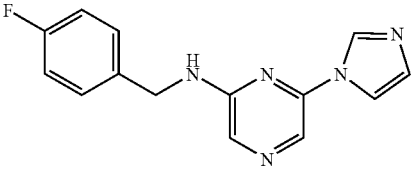<br>Chemistry 9 | − | + | − | + | − |
| 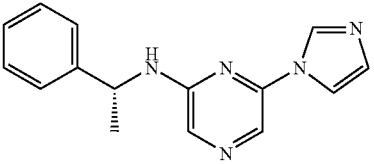<br>Chemistry 17 | − | − | + | + | − |
| 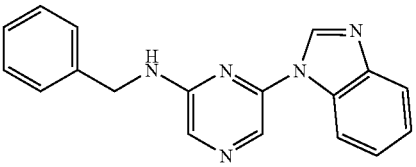<br>Chemistry 18 | + | + | + | + | − |
| 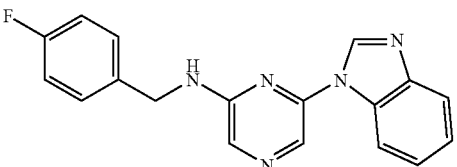<br>Chemistry 19 | + | − | + | + | − |
| 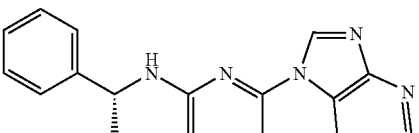<br>Chemistry 48 | − | − | − | − | − |

TABLE 3-continued

Disubstituted pyrazines possessing JAK inhibitory activity

| CHEMISTRY | Jak2 | Jak3 | abl | ack | kdr |
|---|---|---|---|---|---|
| Chemistry 109 | − | + | − | + | − |
| Chemistry 110 | − | − | + | NT | + |
| Chemistry 111 | − | − | + | NT | + |
| Chemistry 112 | + | − | + | + | + |
| Chemistry 113 | + | − | + | + | + |
| Chemistry 114 | − | − | + | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 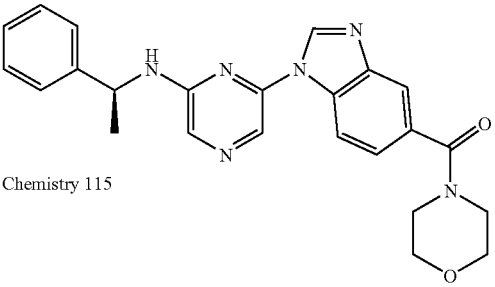  Chemistry 115 | − | − | + | + | + |
| 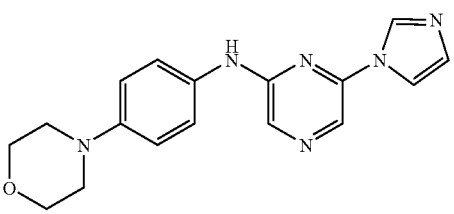  Chemistry 50 | + | − | + | + | − |
| 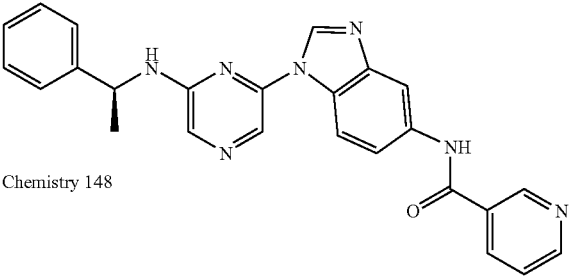  Chemistry 148 | + | − | + | + | + |
| 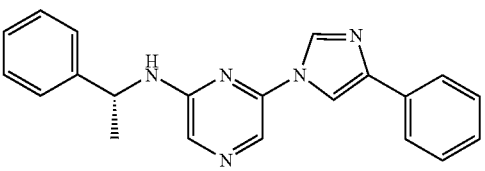  Chemistry 55 | − | − | + | + | + |
| 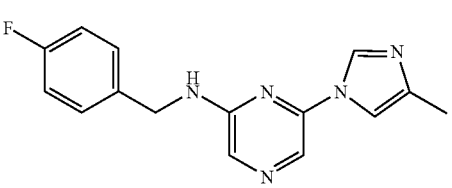  Chemistry 7 | + | − | − | − | − |
| 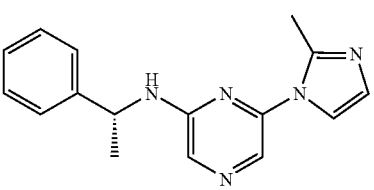  Chemistry 62 | − | − | − | + | − |

TABLE 3-continued
Disubstituted pyrazines possessing JAK inhibitory activity
| CHEMISTRY | Jak2 | Jak3 | abl | ack | kdr |
|---|---|---|---|---|---|
| 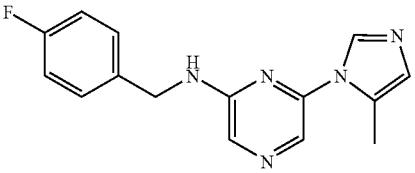 Chemistry 63 | − | − | + | + | − |
| 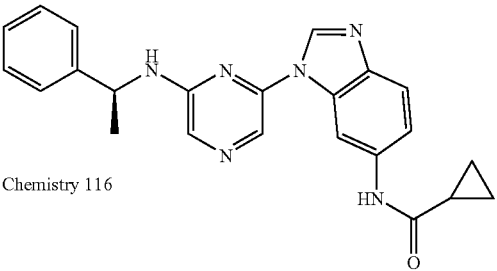 Chemistry 116 | − | − | + | + | + |
| 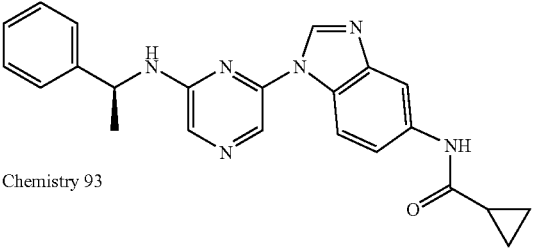 Chemistry 93 | − | − | + | + | + |
| 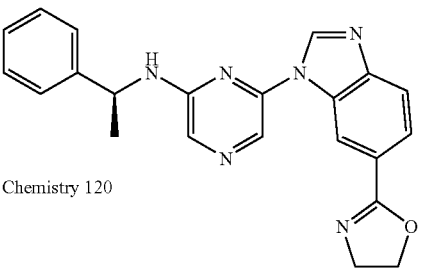 Chemistry 120 | + | − | + | + | + |
| 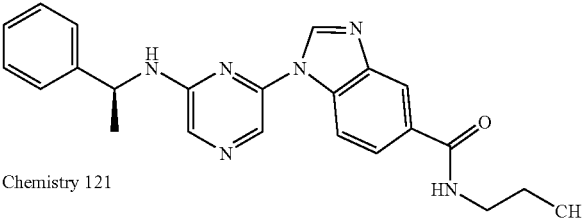 Chemistry 121 | + | + | + | + | + |

TABLE 3-continued

Disubstituted pyrazines possessing JAK inhibitory activity

| CHEMISTRY | Jak2 | Jak3 | abl | ack | kdr |
|---|---|---|---|---|---|
| Chemistry 122 | + | − | + | + | + |
| Chemistry 124 | + | − | + | + | + |
| Chemistry 64 | − | − | − | + | + |
| Chemistry 65 | − | + | − | + | − |
| Chemistry 66 | − | − | + | + | − |
| Chemistry 67 | + | − | + | + | + |

TABLE 3-continued

Disubstituted pyrazines possessing JAK inhibitory activity

| CHEMISTRY | Jak2 | Jak3 | abl | ack | kdr |
|---|---|---|---|---|---|
| Chemistry 82 | − | − | − | − | − |
| Chemistry 84 | + | − | + | + | + |
| Chemistry 125 | − | − | − | + | − |
| Chemistry 126 | − | − | + | + | + |
| Chemistry 127 | − | − | + | + | + |

TABLE 3-continued

Disubstituted pyrazines possessing JAK inhibitory activity

| CHEMISTRY | Jak2 | Jak3 | abl | ack | kdr |
|---|---|---|---|---|---|
| Chemistry 128 | + | − | + | − | + |
| Chemistry 146 | − | − | + | + | + |
| Chemistry 147 | + | + | + | + | + |
| Chemistry 85 | + | − | + | + | + |
| Chemistry 86 | + | + | + | + | + |
| Chemistry 31 | + | − | + | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 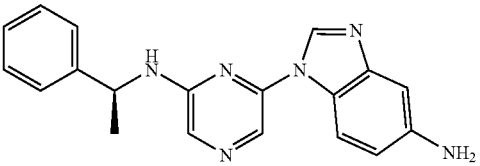<br>Chemistry 92 | + | − | + | + | + |
| 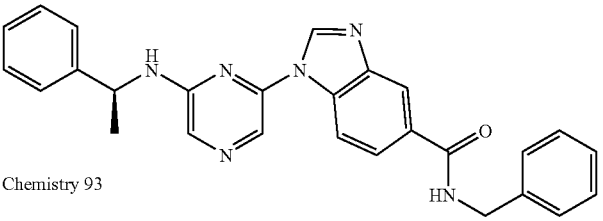<br>Chemistry 93 | − | − | + | + | + |
| 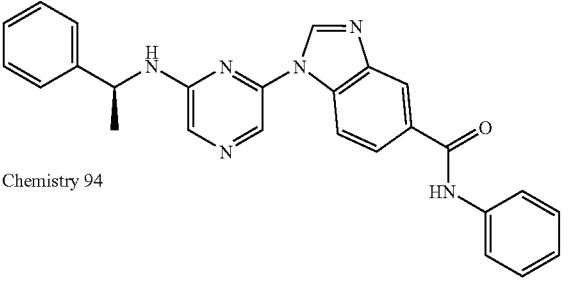<br>Chemistry 94 | − | − | + | + | − |
| 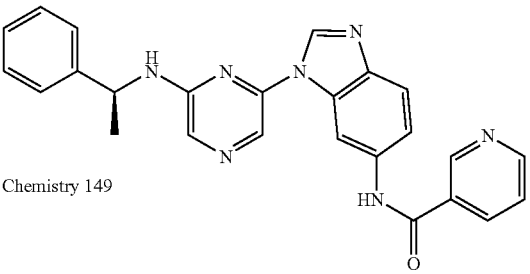<br>Chemistry 149 | + | − | + | + | + |
| 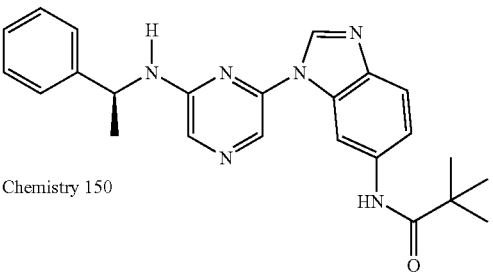<br>Chemistry 150 | + | + | + | + | + |

TABLE 3-continued

Disubstituted pyrazines possessing JAK inhibitory activity

| CHEMISTRY | Jak2 | Jak3 | abl | ack | kdr |
|---|---|---|---|---|---|
| Chemistry 151 | + | + | + | + | + |
| Chemistry 153 | − | − | + | + | + |
| Chemistry 154 | + | − | + | + | + |
| Chemistry 160 | + | − | + | + | + |
| Chemistry 95 | + | − | + | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 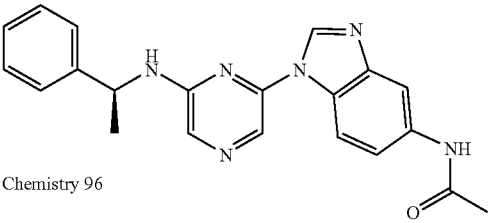<br>Chemistry 96 | − | − | + | + | + |
| 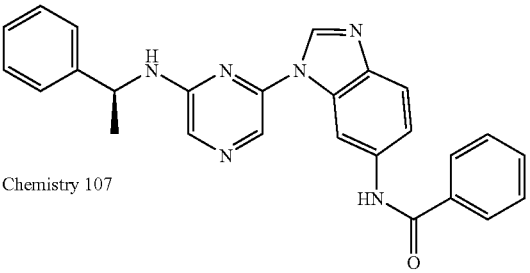<br>Chemistry 107 | − | − | + | + | + |
| 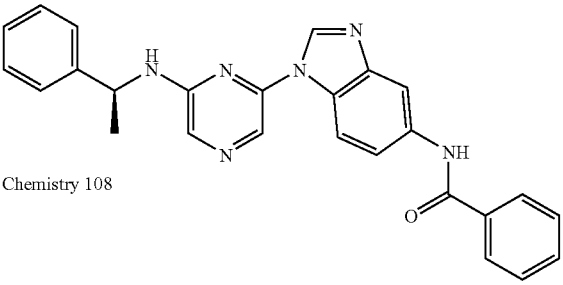<br>Chemistry 108 | − | − | + | + | + |
| 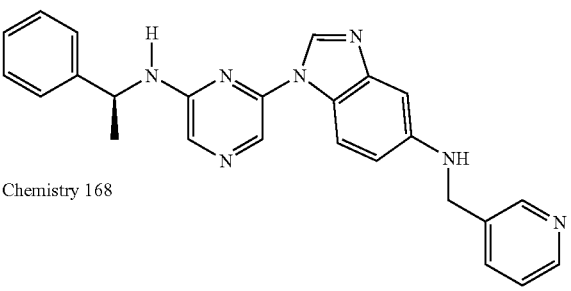<br>Chemistry 168 | + | + | + | + | + |
| 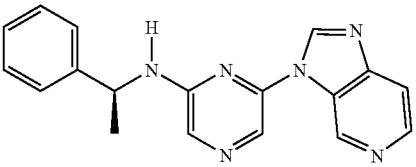<br>Chemistry 169 | + | + | + | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 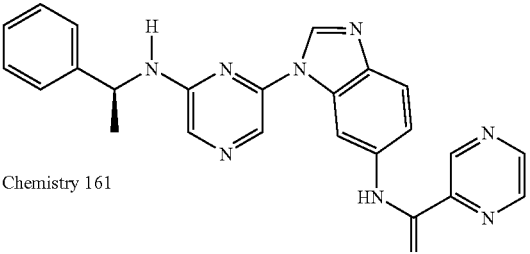<br>Chemistry 161 | + | − | − | + | + |
| 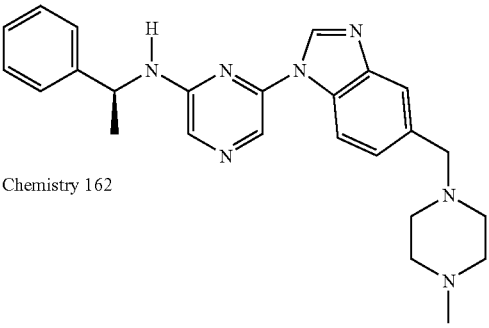<br>Chemistry 162 | − | − | − | + | + |
| 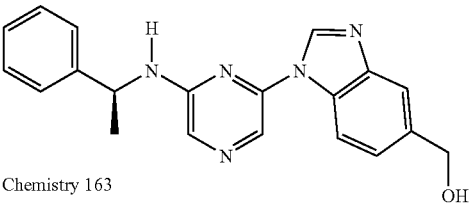<br>Chemistry 163 | + | − | − | + | + |
| 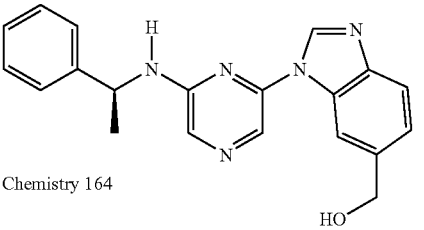<br>Chemistry 164 | + | + | − | + | + |
| 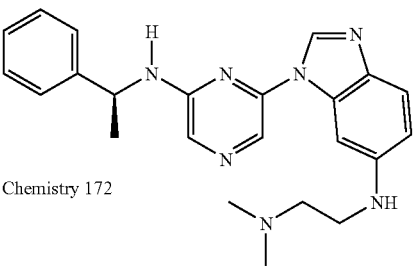<br>Chemistry 172 | + | − | + | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 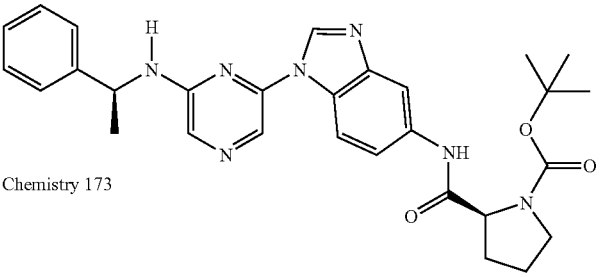 Chemistry 173 | + | − | + | + | + |
| 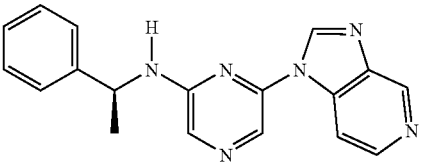 Chemistry 170 | + | + | + | + | + |
| 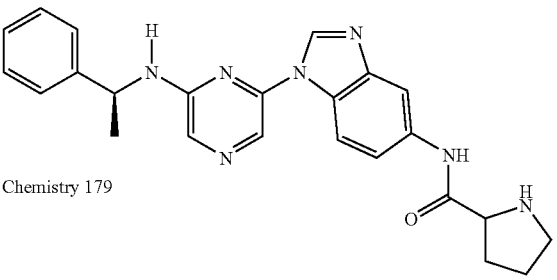 Chemistry 179 | + | + | − | + | + |
| 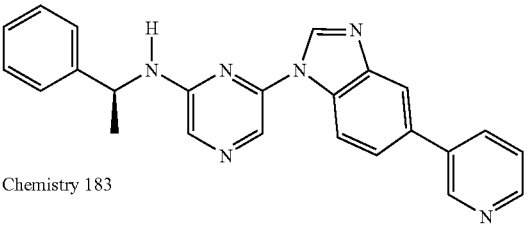 Chemistry 183 | + | + | + | + | + |
| 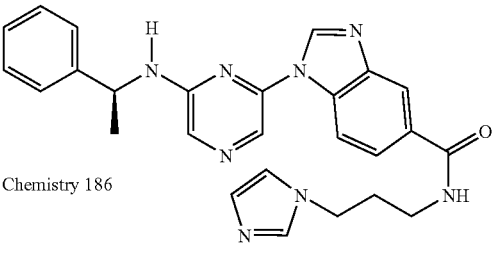 Chemistry 186 | + | − | + | + | + |
| 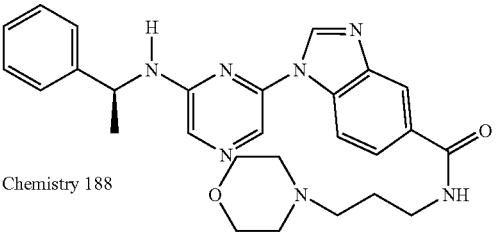 Chemistry 188 | + | + | + | + | + |

TABLE 3-continued

Disubstituted pyrazines possessing JAK inhibitory activity

| CHEMISTRY | Jak2 | Jak3 | abl | ack | kdr |
|---|---|---|---|---|---|
| Chemistry 93 | + | + | + | + | + |
| Chemistry 175 | + | − | + | + | + |
| Chemistry 177 | + | + | − | − | + |
| Chemistry 182 | + | − | + | + | + |
| Chemistry 184 | + | + | + | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 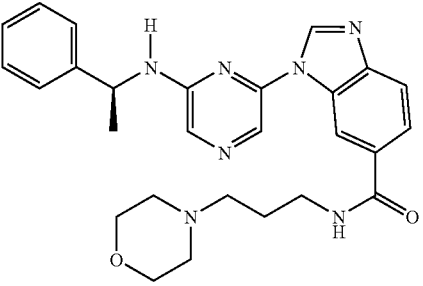<br>Chemistry 187 | + | − | + | + | + |
| 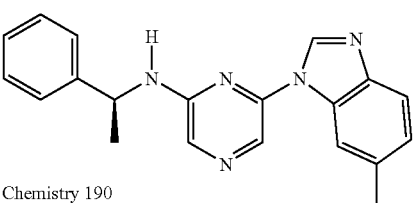<br>Chemistry 190 | + | + | + | + | + |
| 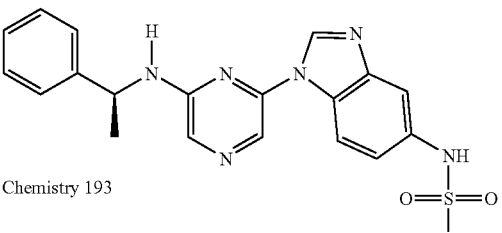<br>Chemistry 193 | + | + | − | − | + |
| 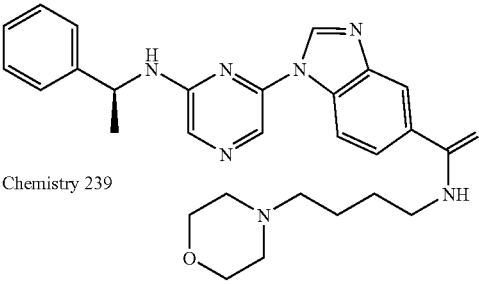<br>Chemistry 239 | + | + | + | + | + |
| 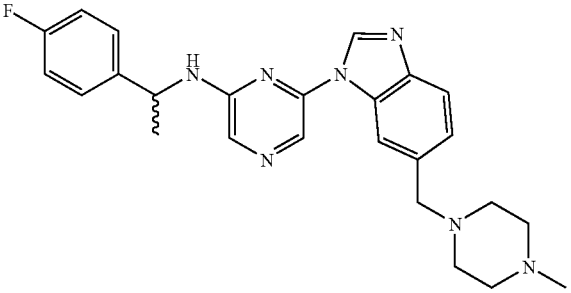<br>Chemistry 499 | − | − | − | + | + |

TABLE 3-continued
Disubstituted pyrazines possessing JAK inhibitory activity
| CHEMISTRY | Jak2 | Jak3 | abl | ack | kdr |
|---|---|---|---|---|---|
| 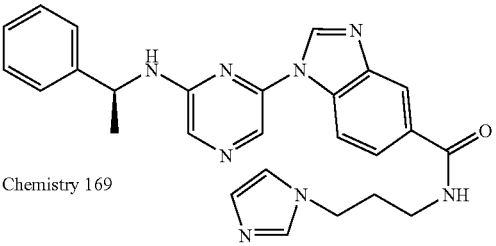 Chemistry 169 | + | − | + | + | + |
| 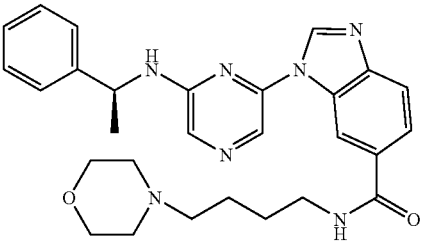 Chemistry 194 | + | + | + | + | + |
| 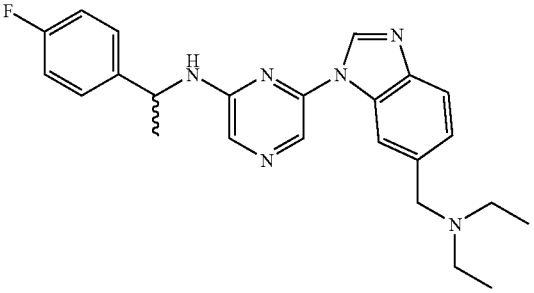 Chemistry 500 | + | − | − | + | + |
| 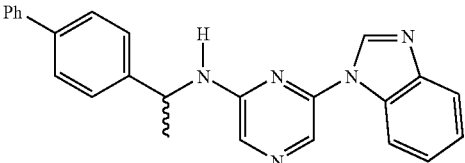 Chemistry 93 | − | − | + | + | − |
| 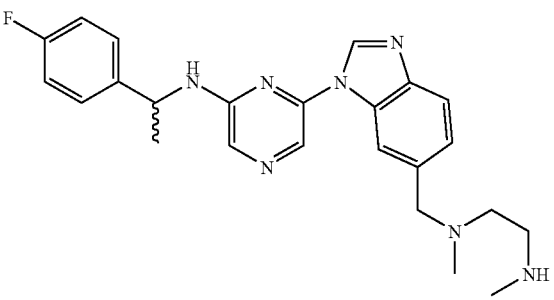 Chemistry 501 | + | − | − | + | + |

What is claimed is:

1. A compound of the formula:

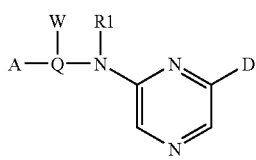

I or pharmaceutically acceptable salts, crystal forms or diastereomers thereof, wherein:

D is:

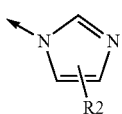

where $X_1, X_2, X_3, X_4$ are optionally substituted carbon, or one of $X_1, X_2, X_3, X_4$ is N;

$R^2$ is 0-4 substituents independently chosen from H, halogen, $C_{1-4}$ alkyl, $CH_2F$, $CHF_2$, $CF_3$, $OCF_3$, aryl, hetaryl, $C_{1-4}$ alkyl$OC_{1-4}$ alkyl, $C_{1-4}$ alkylOaryl, $C_{1-4}$ alkylNR$^3$R$^4$, $CO_2R^3$, CONR$^3$R$^4$, CONR$^3$SO$_2$R$^4$, NR$^3$R$^4$, $C_{1-4}$ alkylNR$^3$R$^4$, nitro, NR$^3$COR$^4$, NR$^5$CONR$^3$R$^4$, NR$^3$SO$_2$R$^4$, $C_{1-4}$ alkylNR$^3$COR$^4$, $C_{1-4}$ alkylNR$^5$CONR$^3$R$^4$, or $C_{1-4}$ alkylNR$^3$SO$_2$R$^4$;

$R^3$ and $R^4$ are each independently H, halogen, $CH_2F$, $CHF_2$, $CF_3$, $C_{1-4}$ alkyl, $C_{1-4}$ alkyl cycloalkyl, $C_{1-4}$ cyclohetalkyl, aryl, $C_{1-4}$ alkyl aryl, hetaryl, $C_{1-4}$ alkyl hetaryl, or may be joined to form an optionally substituted 3-8 membered (saturated or unsaturated) ring optionally containing an atom selected from O, S, NR$^6$;

$R^5$ is H, $C_{1-4}$ alkyl, halogen, $CH_2F$, $CHF_2$, $CF_3$, aryl or hetaryl;

$R^6$ is H, $C_{1-4}$ alkyl, aryl, $C_{1-4}$ alkyl aryl, or $C_{1-4}$ alkyl hetaryl;

$R^1$ is H, $C_{1-4}$ alkyl, $C_{1-6}$ cycloalkyl;

Q is a bond, $CH_2$, $C_{1-4}$ alkyl;

A is aryl, hetaryl optionally substituted with 0-3 substituents independently chosen from halogen, $C_{1-4}$ alkyl, $CH_2F$, $CHF_2$, $CF_3$, $OCF_3$, CN, NR$^8$R$^9$, aryl, hetaryl, $C_{1-4}$ aryl, $C_{1-4}$ hetaryl, $C_{1-4}$ alkylNR$^8$R$^9$, $OC_{1-4}$ alkylNR$^8$R$^9$, nitro, NR$^{10}$C$_{1-4}$NR$^8$R$^9$, NR$^8$COR$^9$, NR$^{10}$CONR$^8$R$^9$, NR$^8$SO$_2$R$^9$, CONR$^8$R$^9$, or CO$_2$R$^8$, where R$^8$ and R$^9$ are each independently H, $C_{1-4}$ alkyl, aryl or which together form an optionally substituted 4-8 membered ring which may contain a heteroatom selected from O, S, NR$^{11}$, where R$^{11}$ is $C_{1-4}$ alkyl, and R$^{10}$ is selected from H, $C_{1-4}$ alkyl; and W is H, $C_{1-4}$ alkyl, or $C_{2-6}$ alkenyl, where $C_{1-4}$ alkyl or $C_{2-6}$ alkenyl may be optionally substituted with $C_{1-4}$ alkyl, OH, $OC_{1-4}$ alkyl, NR$^{12}$R$^{13}$; and R$^{12}$, and R$^{13}$ are each independently H, $C_{1-4}$ alkyl, or may be joined to form an optionally substituted 3-8 membered ring optionally containing an atom selected from O, S, and NR$^{14}$ where R$^{14}$ is H or $C_{1-4}$ alkyl.

2. The compound of claim 1 of the formula II

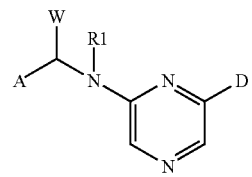

II or pharmaceutically acceptable salts, crystal forms or diastereomers thereof, wherein:

D is:

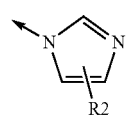

where $X_1, X_2, X_3, X_4$ are optionally substituted carbon, or one of $X_1, X_2, X_3, X_4$ is N;

$R^2$ is 0-4 substituents independently chosen from H, halogen, $C_{1-4}$ alkyl, $CH_2F$, $CHF_2$, $CF_3$, $OCF_3$, aryl, hetaryl, $C_{1-4}$ alkyl$OC_{1-4}$ alkyl, $C_{1-4}$ alkylOaryl, $C_{1-4}$ alkylNR$^3$R$^4$, $CO_2R^3$, CONR$^3$R$^4$, CONR$^3$SO$_2$R$^4$, nitro, NR$^3$R$^4$, $C_{1-4}$ alkylNR$^3$R$^4$, NR$^3$COR$^4$, NR$^5$CONR$^3$R$^4$, $NR^3SO_2R^4$, $C_{1-4}$ alkyl$NR^3COR^4$, $C_{1-4}$ alkyl$NR^5CONR^3R^4$, or $C_{1-4}$ alkyl$NR^3SO_2R^4$;

$R^3$ and $R^4$ are each independently H, halogen, $CH_2F$, $CHF_2$, $CF_3$, $C_{1-4}$ alkyl, $C_{1-4}$ alkyl cycloalkyl, $C_{1-4}$ cyclohetalkyl, aryl, $C_{1-4}$ alkyl aryl, hetaryl, $C_{1-4}$ alkyl hetaryl, or may be joined to form an optionally substituted 3-8 membered (saturated or unsaturated) ring optionally containing an atom selected from O, S, $NR^6$;

$R^5$ is H, $C_{1-4}$ alkyl, halogen, $CH_2F$, $CHF_2$, $CF_3$, aryl or hetaryl;

$R^6$ is H, $C_{1-4}$ alkyl, aryl, hetaryl, $C_{1-4}$ alkyl aryl, or $C_{1-4}$ alkyl hetaryl;

$R^1$ is H, $C_{1-4}$ alkyl, or $C_{1-6}$ cycloalkyl;

W is H or $C_{1-4}$ alkyl; and

A is aryl, hetaryl optionally substituted with 0-3 substituents independently chosen from halogen, $C_{1-4}$ alkyl, $CH_2F$, $CHF_2$, $CF_3$, $OCF_3$, CN, nitro, $NR^8R^9$, aryl, hetaryl, $C_{1-4}$ aryl, $C_{1-4}$ hetaryl, $C_{1-4}$ alkyl$NR^8R^9$, $OC_{1-4}$ alkyl$NR^8R^9$, $NR^{10}C_{1-4}NR^8R^9$, $NR^8COR^9$, $NR^{10}CONR^8R^9$, $NR^8SO_2R^9$, $CONR^8R^9$, or $CO_2R^8$, where $R^8$ and $R^9$ are each independently H, $C_{1-4}$ alkyl, aryl or which together form an optionally substituted 4-8 membered ring which may contain a heteroatom selected from O, S, and $NR^{11}$, where $R^{11}$ is $C_{1-4}$ alkyl, and $R^{10}$ is H or $C_{1-4}$ alkyl.

3. The compound of claim 1, where W is $C_{1-4}$ alkyl wherein the compound possesses S chirality at the chiral carbon bearing W.

4. The compound of claim 3, wherein the compound is a mixture of R and S isomers and the mixture comprises at least 70% of the S isomer.

5. The compound of claim 4, wherein the compound comprises at least 80% of the S isomer.

6. The compound of claim 5, wherein the compound comprises at least 90% of the S isomer.

7. The compound of claim 6, wherein the compound comprises at least 95% of the S isomer.

8. The compound of claim 7, wherein the compound comprises at least 99% of the S isomer.

9. The compound of claim 1, wherein the compound is selected from the group consisting of:
N-benzyl-6-(1H-imidazol-1-yl)pyrazin-2-amine,
N-(4-Fluorobenzyl)-6-(1H-imidazol-1-yl)pyrazin-2-amine,
6-(1H-Imidazol-1-yl)-N-[(1R)-1-phenylethyl]pyrazin-2-amine,
6-(1H-imidazol-1-yl)-N-(4-morpholin-4-ylphenyl)pyrazin-2-amine,
N-[(1R)-1-Phenylethyl]-6-(4-phenyl-1H-imidazol-1-yl)pyrazin-2-amine, and
6-(1H-Imidazol-1-yl)-N-[(1S)-1-phenylethyl]pyrazin-2-amine.

10. The compound of claim 1, wherein the compound is selected from the group consisting of:

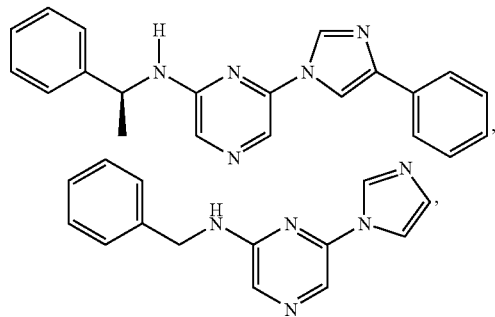

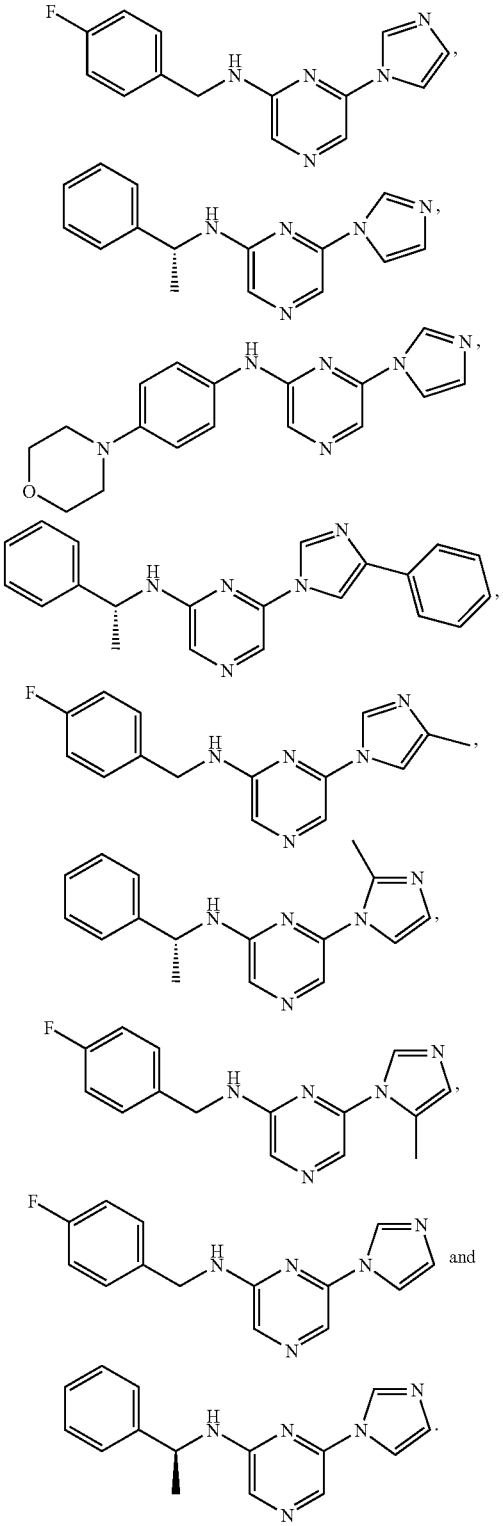

11. A pharmaceutical composition comprising a pharmaceutically acceptable carrier and at least one compound of claim 1.